US010130700B2

(12) United States Patent
Taubenberger

(10) Patent No.: US 10,130,700 B2
(45) Date of Patent: Nov. 20, 2018

(54) POLYVALENT INFLUENZA VIRUS-LIKE PARTICLES (VLPS) AND USE AS VACCINES

(71) Applicant: The United States of America, as represented by the Secretary, Department of Health and Human Services, Washington, DC (US)

(72) Inventor: Jeffery K. Taubenberger, Springfield, VA (US)

(73) Assignee: The United States of America, as represented by the Secretary, DHHS, Washington, DC (US)

( * ) Notice: Subject to any disclaimer, the term of this patent is extended or adjusted under 35 U.S.C. 154(b) by 0 days.

(21) Appl. No.: 15/317,593

(22) PCT Filed: May 8, 2015

(86) PCT No.: PCT/US2015/029843
§ 371 (c)(1),
(2) Date: Dec. 9, 2016

(87) PCT Pub. No.: WO2015/195218
PCT Pub. Date: Dec. 23, 2015

(65) Prior Publication Data
US 2017/0128562 A1 May 11, 2017

Related U.S. Application Data

(60) Provisional application No. 62/014,821, filed on Jun. 20, 2014.

(51) Int. Cl.
*A61K 39/145* (2006.01)
*A61K 39/00* (2006.01)
*C07K 14/005* (2006.01)
*A61K 39/12* (2006.01)
*C12N 7/00* (2006.01)

(52) U.S. Cl.
CPC ............ *A61K 39/145* (2013.01); *A61K 39/12* (2013.01); *A61K 2039/5258* (2013.01); *A61K 2039/543* (2013.01); *A61K 2039/55572* (2013.01); *A61K 2039/70* (2013.01); *C12N 2760/16123* (2013.01); *C12N 2760/16134* (2013.01); *C12N 2760/16223* (2013.01); *C12N 2760/16234* (2013.01)

(58) Field of Classification Search
CPC .................. A61K 39/12; A61K 39/145; A61K 2039/5258; C12N 2760/16134; C07K 14/005
See application file for complete search history.

(56) References Cited

FOREIGN PATENT DOCUMENTS

| WO | WO 2007/130330 A2 | 11/2007 |
| WO | WO2007130330 * | 11/2007 |
| WO | WO 2010/125461 A1 | 11/2010 |
| WO | WO 2011/102900 A1 | 8/2011 |
| WO | WO 2013/068593 A1 | 5/2013 |

OTHER PUBLICATIONS

Cottey et al., "Influenza Virus," *Curr Proto Immunol.* 42:19.11:19.11.1-19.11.32, 2001.
Dugan et al., "The Evolutionary Genetics and Emergence of Avian Influenza Viruses in Wild Birds," *PLoS Pathog* 4:e1000076, 2008.
Easterbrook et al., "Protection against a lethal H5N1 influenza challenge by intranasal immunization with virus-like particles containing 2009 pandemic H1N1 neuraminidase in mice," *Virology* 432:39-44, 2012.
Kang et al., "Influenza virus-like particles as pandemic vaccines," *Curr Top Microbiol Immunol.* 333:269-289, 2009.
Perrone et al., "Intranasal vaccination with 1918 influenza virus-like particles protects mice and ferrets from lethal 1918 and H5N1 influenza virus challenge," *J Virol.* 83:5726-5734, 2009.
Quan et al., "Virus-like particle vaccine protects against 2009 H1N1 pandemic influenza virus in mice," *PLoS One* 5:e9161, 2010.
Smith et al., "Development of influenza H7N9 virus like particle (VLP) vaccine: Homologous A/Anhui/1/2013 (H7N9) protection and heterologous A/chicken/Jalisco/CPA1/2012 (H7N3) cross-protection in vaccinated mice challenged with H7N9 virus," *Vaccine* 31:4305-4313, 2013.
Taubenberger et al., "Evaluation of Heterosubtypic Immunity Following Vaccination with Influenza A Hemagglutinin Viral-Like Particles," abstract presented at American Society of Virology meeting on Jun. 23, 2014 (abstract submitted Feb. 3, 2014).
Taubenberger, "Development of a broadly reactive polyvalent viral-like particle (VLP) universal influenza vaccine for pandemic prevention," presented to the TEAC committee at the NIH in a non-public meeting on May 28, 2014.
Tretyakova et al., "Intranasal vaccination with H5, H7 and H9 hemagglutinins co-localized in a virus-like particle protects ferrets from multiple avian influenza viruses," *Virology* 442:67-73, 2013.
Wu et al., "A VLP vaccine induces broad-spectrum cross-protective antibody immunity against H5N1 and H1N1 subtypes of influenza A virus," *PLoS One* 7:e42363, 2012.

(Continued)

*Primary Examiner* — Barry A Chestnut
(74) *Attorney, Agent, or Firm* — Klarquist Sparkman, LLP

(57) ABSTRACT

This disclosure provides compositions that include a mixture of viral like particles (VLPs), expressing different individual influenza hemagglutinin (HA) proteins that elicit broadly reactive immune responses to a wide variety of influenza viruses. For example, the composition can include at least two different influenza VLPs, a first VLP comprising a first HA polypeptide and a second VLP comprising a second influenza HA polypeptide, wherein the first and the second HA polypeptide are different subtypes and/or are from different influenza viruses, and a pharmaceutically acceptable carrier and/or an adjuvant. Methods of using the disclosed polymeric influenza VLP compositions to stimulate an immune response against influenza viruses, for example as a pre-pandemic or a seasonal vaccine, are provided.

29 Claims, 7 Drawing Sheets
Specification includes a Sequence Listing.

(56) References Cited

OTHER PUBLICATIONS

PCT/US2015/029843 International Search Report and Written Opinion dated Jul. 23, 2015 (8 pages).

* cited by examiner

FIG. 2A FIG. 2B
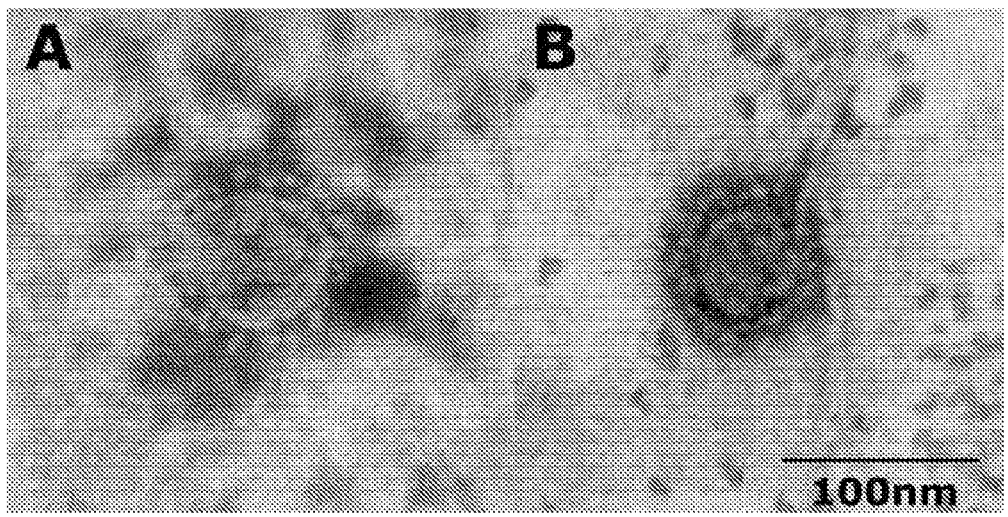
NA expressing VLP
FIG. 2C
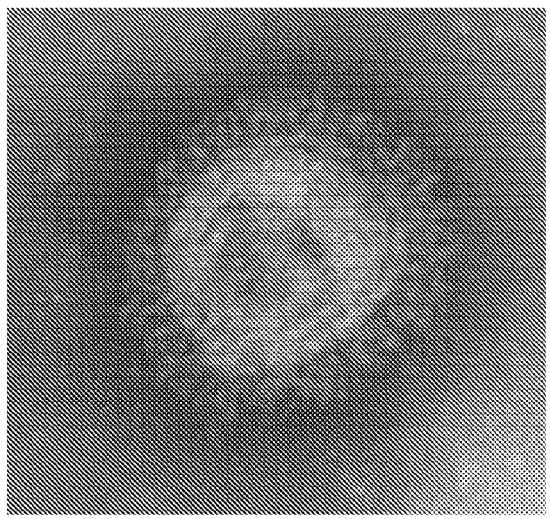
HA expressing VLP

FIG. 3

Survival of H5N1 virus challenge

- mock
- VN/1203 NA
- CA/09 NA

FIG. 4

Survival of lethal 1918 virus challenge

- mock
- H2+H5/H3+H7
- H3+H7/H2+H5

FIG. 5

Survival of lethal avian H6N1 virus challenge

- mock
- H1+H3/H2+H7
- H5+H3/H1+H7

Homologous Challenge FIG. 8A
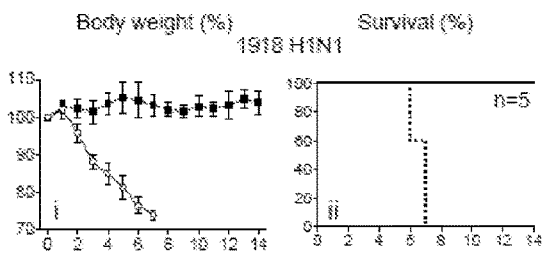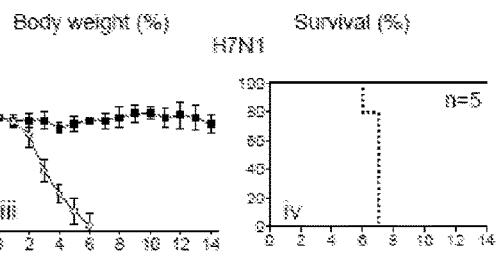
Intrasubtypic Challenge FIG. 8B
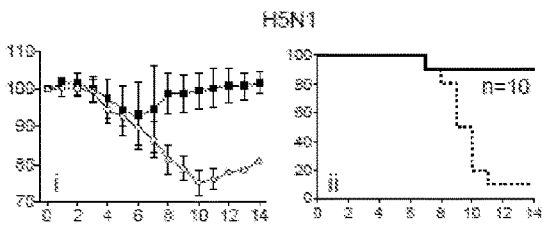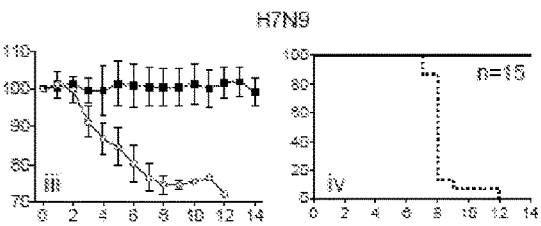
Heterosubtypic Challenge FIG. 8C
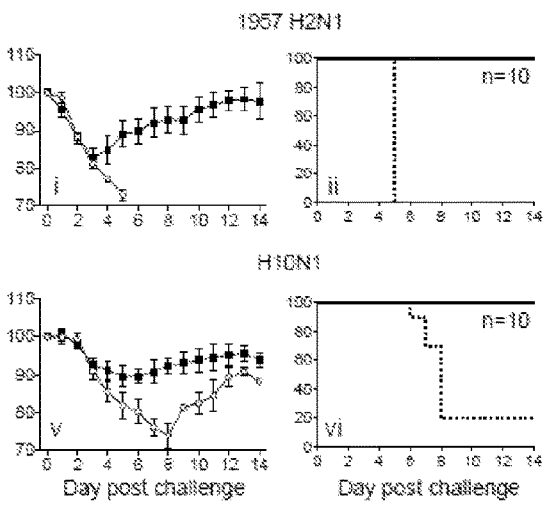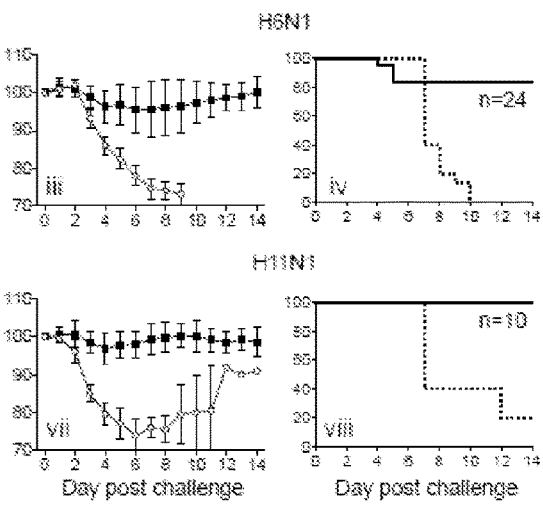
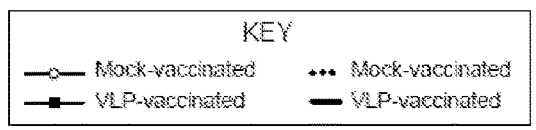

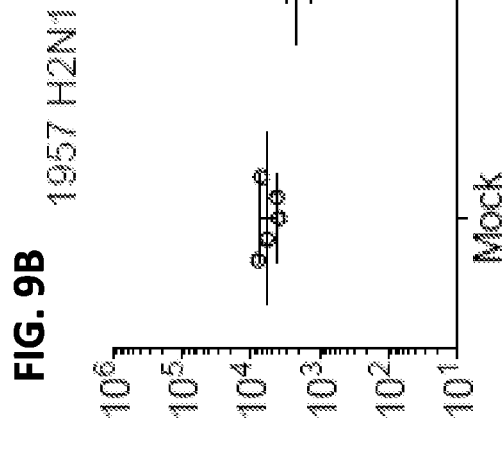
FIG. 9B 1957 H2N1
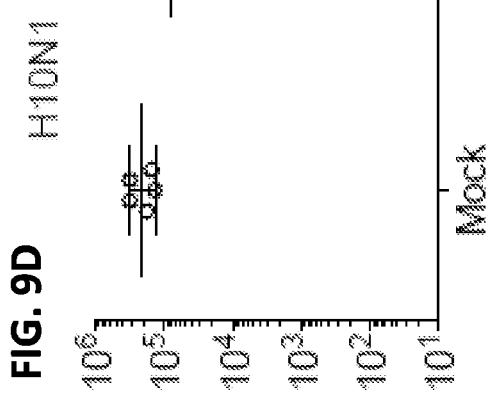
FIG. 9D H10N1
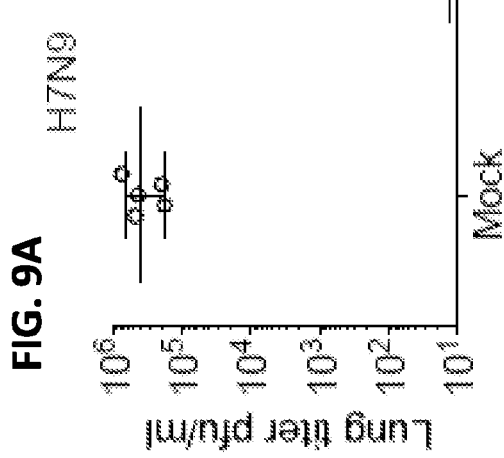
FIG. 9A H7N9
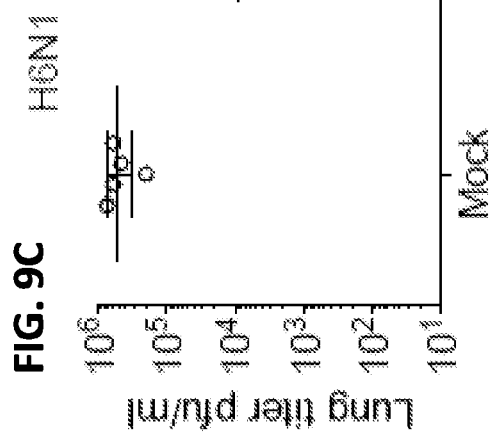
FIG. 9C H8N1

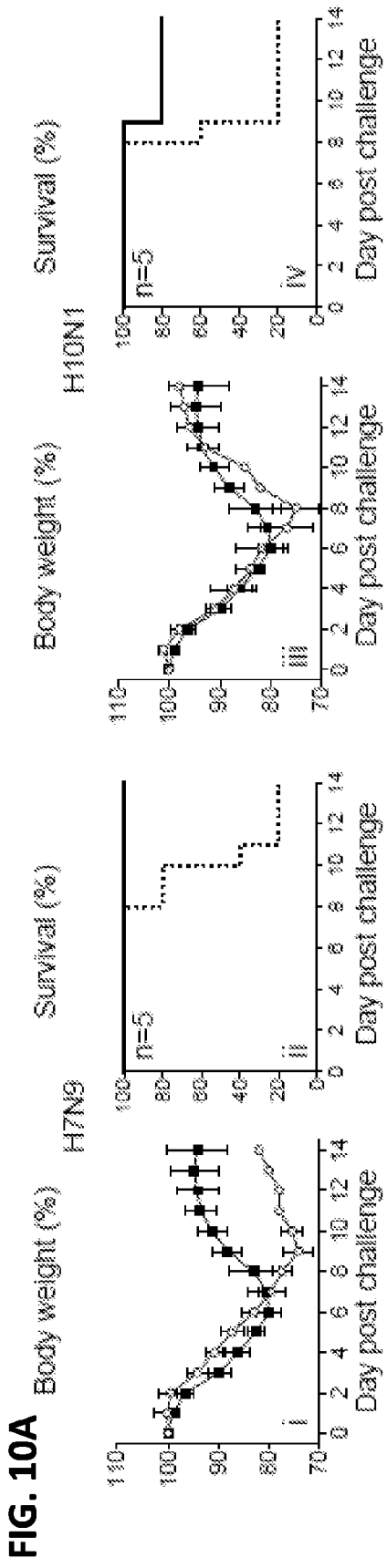
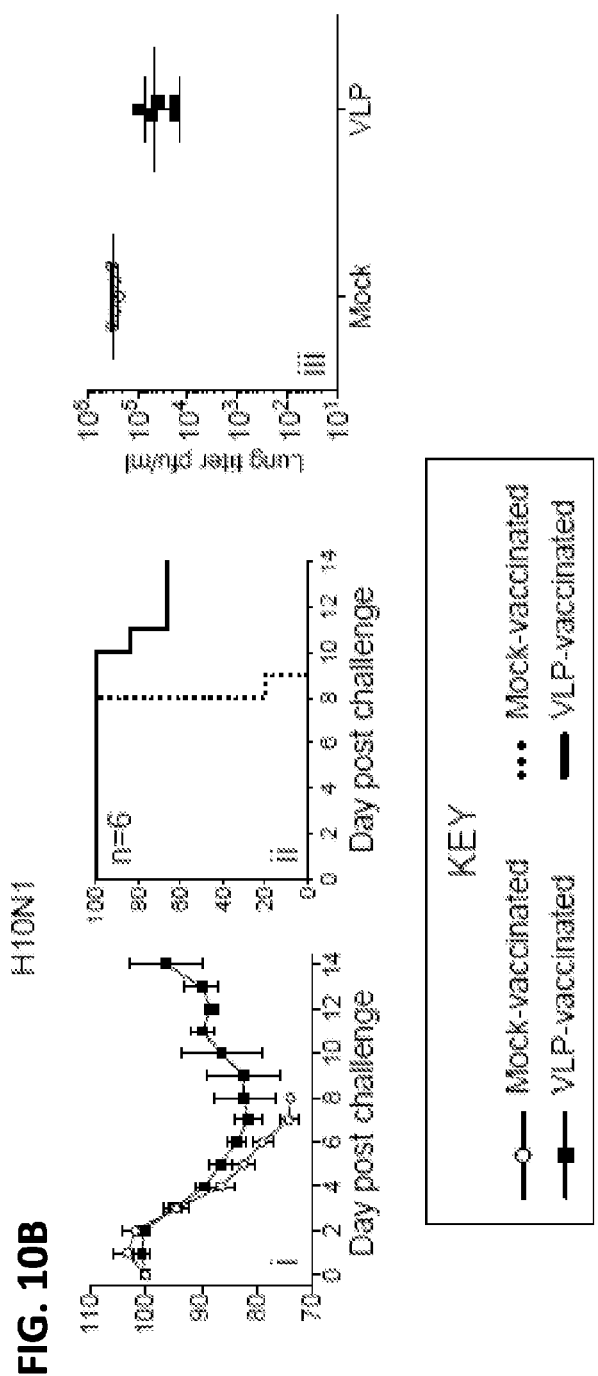
FIG. 10A
FIG. 10B

POLYVALENT INFLUENZA VIRUS-LIKE PARTICLES (VLPS) AND USE AS VACCINES

CROSS REFERENCE TO RELATED APPLICATION

This is the U.S. National Stage of International Application No. PCT/US2015/029843, filed May 8, 2015, which was published in English under PCT Article 21(2), which in turn claims the benefit of U.S. provisional application No. 62/014,821 filed Jun. 20, 2014, herein incorporated by reference.

FIELD

This disclosure concerns compositions that include a mixture of viral like particles (VLPs) expressing individual influenza hemagglutinin (HA) proteins that elicit broadly reactive immune responses to a wide variety of influenza viruses, and their use to stimulate an immune response, for example as a vaccine.

BACKGROUND

Influenza virus is a member of the Orthomyxoviridae family. There are three types of influenza viruses, designated influenza A, influenza B, and influenza C. Influenza A viruses infect not only humans but also many species of birds and mammals and are classified by subtype of their surface proteins, hemagglutinin (HA) and neuraminidase (NA). The influenza A virion contains a segmented negative-sense RNA genome, which encodes the following proteins: hemagglutinin (HA), neuraminidase (NA), matrix (M1), proton ion-channel protein (M2), nucleoprotein (NP), polymerase basic protein 1 (PB1), PB1-F2, polymerase basic protein 2 (PB2), polymerase acidic protein (PA), PA-X, nonstructural protein 1 (NS1), and nonstructural protein 2 (NS2). The HA, NA, M1, and M2 are membrane associated, whereas NP, PB1, PB2, PA, are nucleocapsid associated proteins, and the PB1-F2, NS2, and PA-X proteins are nonstructural proteins. The HA and NA proteins are envelope glycoproteins, with HA responsible for virus attachment and penetration of the viral particles into the cell and NA responsible for viral release, and are the sources of the major immunodominant epitopes for virus neutralization and protective immunity.

The public health burden of influenza is great, with an average of >200,000 hospitalizations per year in the U.S., and resulting mortality of seasonal influenza ranging from 3,000 to 49,000 per year in the U.S. In pandemic years these totals can increase dramatically. In 1918, the worst influenza pandemic on record, 675,000 people died in the U.S. and up to 50 million people globally. Additionally, novel strains of influenza with HA and NA subtypes for which most people do not have any immunity can emerge in animals (e.g., birds and swine) and be transmitted to people. Zoonotically derived outbreaks can ensue which might lead to a pandemic. In the last few years, a swine H1N1 virus adapted to people to cause a pandemic in 2009. Bird-adapted strains of H5N1, H9N2, H7N9, H10N8, and H6N1 have all caused human infections, often with significant mortality.

Since the 2009 pandemic, zoonotic infections with H5N1, H7N9, H3N2v, and recently H6N1 and H10N8 have been observed, stressing the need for a broadly reactive or universal vaccine approach that extends beyond protection against defined circulating seasonal variants, which could help prevent or mitigate a future pandemic by serving as a pre-pandemic vaccine. Inactivated vaccines delivered intramuscularly do not generate a robust mucosal immune response, and live attenuated influenza vaccines are problematic because they are over-attenuated, have restricted usage guidelines, and also because live viruses expressing hemagglutinin (HA) and/or neuraminidase (NA) subtypes not present in seasonal strains cannot be used because of the risk of reassortment with wild type viruses. Thus there is a need for a broadly reactive vaccine that can generate a protective immune response without the requirement of employing a live attenuated virus. The major difficulty faced by universal influenza vaccine approaches is the antigenic variability of different HA and NA subtypes. A universal vaccine could serve as a pre-pandemic vaccine, providing protection against zoonotic influenza infections as well as providing protection against seasonal influenza virus strains, or both.

SUMMARY

Provided herein is a safe, broadly reactive vaccine that can elicit both mucosal and systemic immunity using an intranasal delivery of a mixture of viral like particles (VLPs) expressing individual influenza hemagglutinin (HA) peptides, such as HA peptides from influenza A or B. In some examples, the mixture of VLPs, referred to herein as polyvalent VLPs, includes VLPs or populations of VLPs each expressing a different HA subtype (such as two VLP populations, each expressing a different HA subtype), and can further include a VLP or VLP population expressing a neuraminidase (NA) subtype (such as two VLP populations, each expressing a different NA subtype). Without wishing to be bound to a particular theory, it is proposed that conserved epitopes in the HA head and stalk domains allow cross-reactive vaccines to be produced. Expression of different HA (and in some examples NA) subtypes on individual VLPs in a polyvalent composition boosts responses to stalk antigens and HA receptor binding domain antigens conserved between HA subtypes, and in some examples stimulates immunogenicity of NA antigens since they are expressed on VLPs independently of immunodominant HA. The immune responses generated using these polyvalent VLPs can provide broad protective immunity against a wide variety of influenza viruses. In one example, polyvalent VLPs include one or more VLP populations each expressing a different HA peptide from influenza A, and in some examples also one or more VLP populations each expressing a different NA peptide from influenza A, wherein the VLPs may or may not express influenza A matrix proteins (e.g., M1 and/or M2). Such a polyvalent VLP population can be used to provide a broadly protective 'universal' pre-pandemic vaccine. In another example, polyvalent VLPs include two or more VLP populations, wherein one VLP population expresses an HA peptide from influenza A (such as one of any of the 16 HA proteins), and a second VLP population expresses an HA peptide from influenza B, and in some examples also a VLP population expressing a NA peptide from influenza A (such as one of any of the 9 NA proteins), and a second VLP population expresses an HA peptide from influenza B, wherein the VLPs may or may not express influenza A and/or B matrix proteins. Such a polyvalent VLP population (which includes influenza A and B VLPs) can be used to provide a broadly protective seasonal vaccine. Thus, the disclosure provides broadly protective 'universal' pre-pandemic vaccines and more broadly reactive seasonal vaccines with the addition of influenza B HA VLPs.

Provided herein are compositions that include at least two different influenza A VLPs, a first VLP having a first influenza A HA polypeptide and a second VLP having a second influenza A HA polypeptide, wherein the first and the second HA polypeptide are different subtypes. In some examples the first influenza A HA polypeptide is HA subtype H1, H2, H5, H6, H8, H9, H11, H12, H13, or H16 and the second influenza A HA polypeptide is HA subtype H3, H4, H7, H10, H14, or H15. One skilled in the art will appreciate that additional VLPs or VLP populations can be included in the composition. For example, the composition can include 2, 3, 4, 5, 6, 7, 8, 9, 10, 11, 12, 13, 14, 15, 16, 17, or 18 different VLPs or VLP populations, with each having or expressing a different HA subtype. Such compositions can also include a pharmaceutically acceptable carrier, an adjuvant, or both. In some examples, the disclosed compositions are formulated for mucosal immunization, such as intranasal administration. Also provided are syringes or containers that include the disclosed compositions. In some examples, such a composition that includes influenza A VLPs can be used as a pre-pandemic vaccine.

Also provided herein are compositions that include at least two different influenza B VLPs, a first VLP having a first influenza B HA polypeptide and a second VLP having a second influenza B HA polypeptide, wherein the first and the second HA polypeptide are different antigenic lineages of influenza B HA. In some examples the first influenza B HA polypeptide is from the Yamagata-like HA lineage and the second influenza B HA polypeptide is from the Victoria-like HA lineage. One skilled in the art will appreciate that additional VLPs or VLP populations can be included in the composition. For example, the composition can include 2, 3, 4, 5, 6, 7, 8, 9, 10, 11, 12, 13, 14, 15, 16, 17, or 18 different VLPs or VLP populations, with each having or expressing a different influenza A HA subtype or influenza B HA lineage. Such compositions can also include a pharmaceutically acceptable carrier, an adjuvant, or both. In some examples, the disclosed compositions are formulated for mucosal immunization, such as intranasal administration. Also provided are syringes or containers that include the disclosed compositions. In some examples, such a composition that includes both influenza A and influenza B VLPs and can be used as a seasonal vaccine.

Provided herein are compositions that include at least two different influenza VLPs, a first VLP having a first influenza A HA polypeptide and a second VLP having a first influenza B HA polypeptide. In some examples the first influenza A HA polypeptide is HA subtype H1, H2, H5, H6, H8, H9, H11, H12, H13, or H16 and the second influenza B HA polypeptide is Victoria-like or Yamagata like influenza B HA. One skilled in the art will appreciate that additional VLPs or VLP populations can be included in the composition. For example, the composition can include at least 2, at least 3, at least 4, at least 5, at least 6, at least 7, at least 8, at least 9, or at least 10, such as 2, 3, 4, 5, 6, 7, 8, 9, 10, 11, 12, 13, 14, 15, 16, 17 or 18 different VLPs or VLP populations, with each having or expressing a different influenza A virus HA subtype or influenza B virus HA type. Such compositions can also include a pharmaceutically acceptable carrier, an adjuvant, or both. In some examples, the disclosed compositions are formulated for mucosal immunization, such as intranasal administration. Also provided are syringes or containers that include the disclosed compositions. In some examples, such a composition that includes influenza A and B VLPs can be used as a seasonal vaccine.

In some examples, the disclosed compositions further include a VLP having or expressing an influenza A or B neuraminidase (NA) polypeptide, or can include a first VLP population having or expressing an influenza A NA polypeptide an a second VLP population having or expressing an influenza B NA polypeptide. Thus, in some examples, the disclosed compositions further include two or more different VLPs or VLP populations, each having or expressing a different NA polypeptide, for example, influenza A NA subtype or an influenza B virus Victoria- and/or Yamagata-like NA polypeptide.

In some examples, the HA- or NA-expressing VLPs include other proteins, such as an influenza matrix protein, for example influenza A M1, influenza M2, or both (e.g., in a VLP that includes influenza A HA or NA), or influenza B matrix protein (for example M1, BM2, or both) (e.g., in a VLP that includes influenza B HA or NA).

In some examples, the VLPs in the composition are produced by a method using transfection of mammalian cells or infection of insect cells. For example, the VLP can be produced by transfecting a mammalian host cell (or infecting an insect cell) with a vector or virus encoding an HA polypeptide or a vector encoding an NA polypeptide. Optionally, the cell is also transfected/infected with a vector or virus encoding an influenza matrix protein (such as influenza A M1 protein, M2 protein, or both; or influenza B M1, BM2, or both). However, in some examples the matrix protein is expressed from the same vector or virus as the HA or NA protein. The cells are incubated under conditions sufficient to allow for expression of the HA, NA, and/or matrix proteins.

Methods of using the disclosed polyvalent VLP compositions are provided. In one example, the compositions are used to elicit an immune response to influenza virus in a subject. In one example, the VLPs includes populations of VLPs expressing HA (and in some example also populations of VLPs expressing NA) from influenza A, and such vaccines can be used as a pre-pandemic vaccine. In another example, the VLPs includes populations of VLPs expressing HA (and in some example also VLP populations of expressing NA) from influenza A and influenza B (that is, one VLP population expressing influenza A HA, and another VLP population expressing influenza B HA), and such vaccines can be used as a seasonal vaccine.

Such methods can include administering a therapeutically effective amount of the disclosed compositions to a subject, thereby eliciting an immune response to influenza virus in a subject. In some examples, the immune response is elicited against influenza A, influenza B, or both, such as one or more of H1N1 (such as 1918 H1N1 or 2009 H1N1), H2N1, H2N2 (such as 1957 H2N2), H3N2 (such as 1968 H3N2), H5N1, H6N1, H7N9, H9N2, H10N8, H10N1, and a major influenza B virus antigenic lineage(s) (e.g., Yamagata-like and/or Victoria-like). In one example, the compositions are used to immunize a subject against influenza virus, such as influenza A, influenza B or both. Such methods can include administering a therapeutically effective amount of the disclosed compositions to a subject, thereby immunizing a subject against influenza virus. In some examples, the subject is immunized against one or more of H1N1 (such as 1918 H1N1 or 2009 H1N1), H2N2 (such as 1957 H2N2), H2N1, H3N2 (such as 1968 H3N2), H5N1, H6N1, H7N9, H9N2, H10N8, H10N1, and a major influenza B virus antigenic lineage(s) (e.g., Yamagata-like and/or Victoria-like). In some examples, the composition is administered intranasally. In some examples, the composition administered includes about 1 µg to about 25 µg of each of the at least two different VLPs in the composition. In some examples, the subject is one who may become (or is) infected with influenza A, such as a mammal or bird, such as a human, chicken, waterfowl, turkey, pig, horse, dog, or cat, or influenza B, such as a human or seal.

The foregoing and other objects and features of the disclosure will become more apparent from the following detailed description, which proceeds with reference to the accompanying figures.

BRIEF DESCRIPTION OF THE DRAWINGS

FIGS. 2A-2C are digital images showing electron microscopy images of VLPs expressing M1 and M2 along with (A) and (B) NA or (C) HA.

FIG. 3 is a survival curve showing 100% survival of NA VLP vaccinated animals, either with the homologous NA or with a heterologous N1, with no survival in the mock vaccinated group. Mice were vaccinated intranasally with NA-only VLPs expressing either the homologous N1 NA of the highly pathogenic avian influenza challenge virus, A/Vietnam/1203/2004 (H5N1) [VN/1203], or the NA of the 2009 pandemic virus, A/California/04/2009 (H1N1) [CA/09], boosted at 3 weeks, and then challenged with a 10× mouse 50% lethal dose ($MLD_{50}$) of VN/1203. From, Easterbrook et al. *Virology*. 432:39-44, 2012.

FIG. 4 is a survival curve showing 100% survival of polyvalent HA VLP vaccinated animals from both vaccinated groups. Mice were vaccinated intranasally with a polyvalent mixture of HA-only VLPs expressing 4 different HA subtypes (H2, H3, H5, and H7). The mice were vaccinated such that one group received H2 and H5 VLPs initially and were boosted at 3 weeks with a mixture of H3 and H7 VLPs. The second group was initially vaccinated with H3 and H7 VLPs followed by a H2 and H5 VLP boost. A third group was mock vaccinated. At six weeks, all animals were challenged with a lethal dose (10×$MLD_{50}$) of the 1918 H1N1 influenza A virus. Note the complete heterosubtypic protection observed from a lethal challenge with an H1 subtype virus with a polyvalent vaccine mixture that did not contain HA VLPs of H1 subtype.

FIG. 5 is a survival curve showing 100% survival of polyvalent HA VLP vaccinated animals from both vaccinated groups. Mice were vaccinated intranasally with a polyvalent mixture of HA-only VLPs expressing 4 different HA subtypes in 2 groups (group 1: H1, H2, H3, and H7; group 2: H1, H3, H5, and H7). The mice were vaccinated such that group one received H1 and H3 VLPs initially and were boosted at 3 weeks with a mixture of H2 and H7 VLPs. The second group was initially vaccinated with H3 and H5 VLPs followed by a H1 and H7 VLP boost. A third group was mock vaccinated. At six weeks, all animals were challenged with a lethal dose (10×$MLD_{50}$) of an avian H6N1 influenza A virus. Note the complete heterosubtypic protection observed from a lethal challenge with an H6 subtype virus with a polyvalent vaccine mixture that did not contain HA VLPs of H6 subtype.

FIGS. 8A-8C are graphs showing that VLP vaccination protects mice from lethal influenza challenge across HA subtypes. (A) Polyvalent vaccination completely protected against challenge with influenza viruses expressing identical (homologous) HA proteins. Mice were challenged with 1918 H1N1 (i, ii; n=5) or H7N1 (iii, iv; n=5). (B) Vaccinated mice were protected from intrasubtypic (heterologous) challenge with H5N1 (i, ii; n=10) or H7N9 (iii, iv; n=15) virus. (C) Vaccinated mice were challenged with heterosubtypic influenza A viruses (H2N1 (i, ii; n=10), H6N1 (iii, iv; VLP n=24, mock n=15), H10N1 (v, vi; n=10), or H11N1 (vii, viii; VLP n=10; mock n=5).

FIGS. 9A-9D are plots showing that viral replication is reduced in the lungs of VLP vaccinated mice. Mice were vaccinated and challenged with (A) H7N9, (B) H2N1, (C) H6N1, or (D) H10N1. At 3 days post-infection, lungs were harvested and titer was determined by plaque assay.

FIGS. 10A-10B are graphs showing the protective efficacy of VLP vaccination. (A) VLP vaccination protects mice from lethal challenge 6 months post-vaccination. Eight-week old mice were VLP-vaccinated (filled square; solid line) or mock-vaccinated (open circle; dotted line). At 6 months post-initial vaccination, mice were challenged with H7N9 (i, ii; n=5) or H10N1 (iii, iv; n=5) and weights were recorded for 14 days following challenge. (B) Vaccination protects aged mice from lethal challenge. Eight-month old mice were vaccinated. Mice were challenged with H10N1 chimeric influenza virus 50 days post-vaccination. Weight loss (i) and survival (ii) was monitored for 14 days following infection (n=5). Lungs were harvested at 3 days post-challenge (iii) and titer was determined by plaque assay (n=5). Weight loss (Ai; Aiii; Bi) and lung titers (Biii) were significantly reduced in vaccinated mice compared to mock (p<0.05).

SEQUENCE LISTING

Figure 1A:
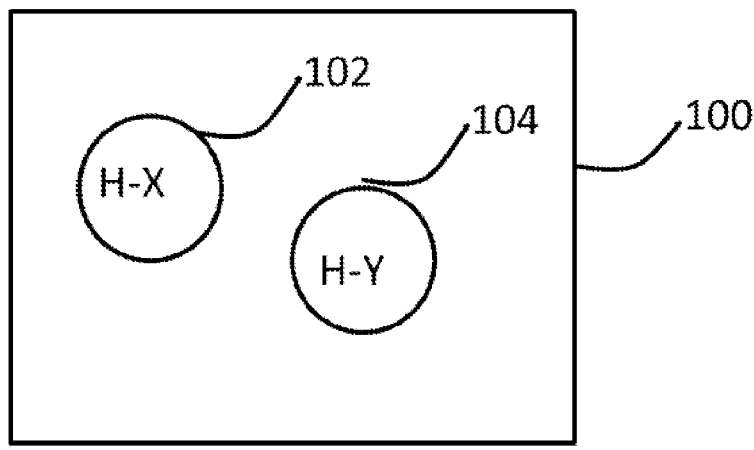
FIGS. 1A-1C provide schematic diagrams of exemplary influenza polyvalent VLP compositions provided herein.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 6, 2016, 216 KB, entitled "Sequence Listing.txt." is part of the disclosure and is incorporated by reference.

SEQ ID NOS: 1 and 2 are exemplary influenza A HA subtype 1 (H1) nucleic acid and protein sequences, respectively (GenBank Accession Nos: CY017275.1 and ABK40634.1 respectively). Coding sequence is nt 19-1719 of SEQ ID NO: 1. Signal peptide is aa 1-17, domain HA1 is aa 18-344 and domain HA2 is aa 345-566.

SEQ ID NOS: 3 and 4 are exemplary influenza A HA subtype 1 (H1) nucleic acid and protein sequences, respectively (GenBank Accession Nos: AF117241.1 and AAD17229.1 respectively). Coding sequence is nt 1-1701 of SEQ ID NO: 3. Signal peptide is aa 1-19, domains HA1 and HA2 are aa 20-566.

SEQ ID NOS: 5 and 6 are exemplary influenza A HA subtype 2 (H2) nucleic acid and protein sequences, respectively (GenBank Accession Nos: CY018877.1 and ABM21949.1 respectively). Coding sequence is nt 29-1717 of SEQ ID NO: 5. Signal peptide is aa 1-15, domain HA1 is aa 16-340 and domain HA2 is aa 341-562.

SEQ ID NOS: 7 and 8 are exemplary influenza A HA subtype 2 (H2) nucleic acid and protein sequences, respectively (GenBank Accession Nos: J02127.1 and AAA43185.1 respectively). Coding sequence is nt 47-88 (signal peptide), CDS nt 89-1060 and nt 1064-1729 of SEQ ID NO: 7. Signal peptide is aa 2-15, domain HA1 is aa 16-339 and domain HA2 is aa 341-562.

SEQ ID NOS: 9 and 10 are exemplary influenza A HA subtype 3 (H3) nucleic acid and protein sequences, respectively (GenBank Accession Nos: CY019197.1 and ABM66853.1 respectively). CDS of signal peptide nt 9-56, HA1 nt 57-1043 and HA2 nt 1044-1706 of SEQ ID NO: 9. Signal peptide is aa 1-16, domain HA1 is aa 17-345 and domain HA2 is aa 346-566.

SEQ ID NOS: 11 and 12 are exemplary influenza A HA subtype 5 (H5) nucleic acid and protein sequences, respectively (GenBank Accession Nos: CY053877.1 and ADA82200.1 respectively). Signal peptide nt 8-54, CDS HA1 nt 44-1032 and HA2 nt 1033-1698. Signal peptide aa 1-16, HA1 17-342 and HA2 343-564.

SEQ ID NOS: 13 and 14 are exemplary influenza A HA subtype 7 (H7) nucleic acid and protein sequences, respectively (GenBank Accession Nos: CY022749.1 and ABR37495.1 respectively). Coding sequence signal peptide nt 6-59, CDS HA1 nt 60-1022 and HA2 nt 1023-1685. Signal peptide is aa 1-18, domain HA1 is aa 19-339 and domain HA2 is aa 340-560.

SEQ ID NOS: 15 and 16 are exemplary influenza A NA subtype 1 (N1) nucleic acid and protein sequences, respectively (GenBank Accession Nos: FJ966084.1 and ACP41107.1 respectively).

SEQ ID NOS: 17 and 18 are exemplary influenza A NA subtype 1 (N1) nucleic acid and protein sequences, respectively (GenBank Accession Nos: HM006761.1 and ADD97097.1 respectively). CDS is nt 21-1370 of SEQ ID NO: 17.

SEQ ID NO: 19 is an exemplary influenza A matrix (M1 and M2) nucleic acid sequence (GenBank Accession No: CY002697.1). Coding sequence of M1 is nt 22-780 and coding sequence of M2 is join nt (22 . . . 47, 736 . . . 1003).

SEQ ID NO: 20 is an exemplary influenza A matrix (M1) protein sequence (GenBank Accession No: ABA12718.1).

SEQ ID NO: 21 is an exemplary influenza A matrix (M2) protein sequence (GenBank Accession No: ABA12719.1).

SEQ ID NOS: 22 and 23 are exemplary influenza B HA nucleic acid and protein sequences, respectively (GenBank Accession Nos: CY018765.1 and ABL77255.1 respectively) from B/Yamagata. Coding sequence is nt 18-1769 of SEQ ID NO: 1. Domain HA is aa 18-583.

SEQ ID NOS: 24 and 25 are exemplary influenza B HA nucleic acid and protein sequences, respectively (GenBank Accession Nos: CY152650.1 and AGX19007.1 respectively), from B/Victoria. Coding sequence is nt 16-1773 of SEQ ID NO: 1. Domain HA is aa 18-585.

SEQ ID NOS: 26 and 27 are exemplary influenza B HA nucleic acid and protein sequences, respectively (GenBank Accession Nos: CY187812.1 and AIC73926.1 respectively), from B/Wyoming. Coding sequence is nt 1-1755 of SEQ ID NO: 1. Domain HA is aa 18-584.

SEQ ID NOS: 28 and 29 are exemplary influenza B NA nucleic acid and protein sequences, respectively (GenBank Accession Nos: AB036870.1 and BAB32609.1 respectively) from B/Victoria. The NA sequence is coded by nt 8-1408.

SEQ ID NOS: 30 and 31 are exemplary influenza B NA nucleic acid and protein sequences, respectively (GenBank Accession Nos: NC_002209.1 and NP_056663.1 respectively). The NA sequence is coded by nt 8-1408.

SEQ ID NOS: 32 and 33 are exemplary influenza B NA nucleic acid and protein sequences, respectively (GenBank Accession Nos: D14855.1 and BAA03583.1 respectively) from B/Kanagawa. The NA sequence is coded by nt 8-1408.

SEQ ID NOS: 34 and 35 are exemplary influenza B matrix nucleic acid and protein sequences, respectively (GenBank Accession Nos: AY044171.1 and AAK95902.1 respectively) from B/Shangdong. The matrix sequence is coded by nt 1-747.

SEQ ID NOS: 36 and 37 are exemplary influenza B matrix nucleic acid and protein sequences, respectively (GenBank Accession Nos: AY504605.1 and AAT69429.1 respectively) from B/Victoria. The matrix sequence is coded by nt 25-771.

SEQ ID NOS: 38 and 39 are exemplary influenza B matrix nucleic acid and protein sequences, respectively (GenBank Accession Nos: AB120274.1 and BAD29821.1 respectively) from B/Yamagata. The matrix sequence is coded by nt 1-747.

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, GenBank® Accession Nos., and other references mentioned herein are incorporated by reference in their entirety. In case of conflict, the present specification, including explanations of terms, will control. In addition, the materials, methods, and examples are illustrative only and not intended to be limiting.

In order to facilitate review of the various embodiments of the disclosure, the following explanations of specific terms are provided:

Adjuvant: A substance or vehicle that non-specifically enhances the immune response to an antigen (e.g., influenza HA and/or NA). Adjuvants can be used with the VLPs disclosed herein, for example a part of a pharmaceutical influenza polyvalent VLP composition provided herein. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL. In one example the adjuvant is one or more a toll-like receptor (TLR) agonists, such as an agonist of TLR1/2 (which can be a synthetic ligand) (e.g., Pam3Cys), TLR2 (e.g., CFA, Pam2Cys), TLR3 (e.g., polyI:C, poly A:U), TLR4 (e.g., MPLA, Lipid A, and LPS), TLR5 (e.g., flagellin), TLR7 (e.g., gardiquimod, imiquimod, loxoribine, Resiquimod®), TLR7/8 (e.g., R0848), TLR8 (e.g., imidazoquionolines, ssPolyU, 3M-012), TLR9 (e.g., ODN 1826 (type B), ODN 2216 (type A), CpG oligonucleotides) and/or TLR11/12 (e.g., profilin). In one example the adjuvant is lipid A, such as lipid A monophosphoryl (MPL) from *Salmonella enterica* serotype Minnesota Re 595 (e.g., Sigma Aldrich Catalog # L6895).

Administer: As used herein, administering a composition (such as one containing VLPs) to a subject means to give, apply or bring the composition into contact with the subject. Administration can be accomplished by any of a number of routes, such as, for example, topical, oral, subcutaneous, intramuscular, intraperitoneal, intravenous, intrathecal and intradermal. In one example, administration is mucosal, such as oral, intranasal, pulmonary, rectal or vaginal.

Antibody: An immunoglobulin molecule produced by B lymphoid cells with a specific amino acid sequence. Antibodies are evoked in humans or other animals by a specific antigen (immunogen, such as HA and NA). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen or immunogen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. In some embodiments of the disclosed compositions and methods, the antigen is an influenza HA protein, an influenza NA protein, or both. As used herein, an "immunogenic composition" is a composition comprising an antigen (such as a plurality of VLPs having different influenza HA proteins).

Hemagglutinin (HA): An influenza virus surface glycoprotein. HA mediates binding of the virus particle to a host cells and subsequent entry of the virus into the host cell. HA also causes red blood cells to agglutinate. The nucleotide and amino acid sequences of numerous influenza HA proteins are known in the art and are publically available, such as those deposited with the GenBank® database. HA (along with NA) is one of the two major influenza virus antigenic determinants.

Exemplary HA sequences for 16 HA subtypes from influenza A and examples of HA from influenza B available from the GenBank® database are provided in Table 1 (GenBank® accession numbers are provided).

TABLE 1

Exemplary HA sequences that can be used in the disclosed VLPs

| Antigen | Exemplary Nucleic Acid Sequences | Exemplary Protein Sequences |
|---|---|---|
| H1 | CY017275.1 (SEQ ID NO: 1) | ABK40634.1 (SEQ ID NO: 2) |
| | AF117241.1 (SEQ ID NO: 3) | AAD17229.1 (SEQ ID NO: 4) |

TABLE 1-continued

Exemplary HA sequences that can be used in the disclosed VLPs

| Antigen | Exemplary Nucleic Acid Sequences | Exemplary Protein Sequences |
|---|---|---|
| H2 | CY018877.1 (SEQ ID NO: 5) | ABM21949.1 ((SEQ ID NO: 6) |
| | J02127.1 (SEQ ID NO: 7) | AAA43185.1 (SEQ ID NO: 8) |
| H3 | CY019197.1 (SEQ ID NO: 9) | ABM66853.1 (SEQ ID NO: 10) |
| | AY531037.1 | AAT08004.1 |
| | AB537477.1 | BAJ09300.1 |
| H4 | M25289.1 | AAA43222.1 |
| | M25284.1 | AAA43217.1 |
| | M25283.1 | AAA43216.1 |
| H5 | CY053877.1 (SEQ ID NO: 11) | ADA82200.1 (SEQ ID NO: 12) |
| | AY075033.1 | AAL75847.1 |
| | AY075027.1 | AAL75839.1 |
| H6 | AF474035.1 | AAO33485.1 |
| | AF474029.1 | AAO33479.1 |
| H7 | CY022749.1 (SEQ ID NO: 13) | ABR37495.1 (SEQ ID NO: 14) |
| | AJ584647.1 | CAE48276.1 |
| | JN966905.1 | AET50899.1 |
| H8 | CY166784.1 | AHL82381.1 |
| | CY017749.1 | ABL67099.1 |
| H9 | AF203008.1 | AAF69255.1 |
| | JQ609664.1 | AFC18325.1 |
| | JX273570.1 | AFO83303.1 |
| H10 | GQ176120.1 | ACS89022.1 |
| | GQ176128.1 | ACS89011.1 |
| | GQ176136.1 | ACS89000.1 |
| H11 | DQ435281.1 | ABD66294.1 |
| | DQ424858.1 | ABD91532.1 |
| | DQ435284.1 | ABD66297.1 |
| H12 | CY021301.1 | ABO52621.1 |
| | EU557489.1 | ACE73380.1 |
| H13 | EU293862.1 | ACA48473.1 |
| | EU293859.1 | ACA48470.1 |
| | EU293858.1 | ACA48469.1 |
| H14 | JN696316.2 | AEP68849.2 |
| | JN696314.2 | AEP68847.2 |
| | KJ195668.1 | AHI57322.1 |
| H15 | L43916.1 | AAA92247.1 |
| | L43917.1 | AAA96134.1 |
| H16 | EU293864.1 | ACA48475.1 |
| | CY177441.1 | AHM98288.1 |
| | CY176997.1 | AHM97554.1 |
| HA from IBV | CY018765.1 (SEQ ID NO: 22) | ABL77255.1 (SEQ ID NO: 23) |
| | CY152650.1 (SEQ ID NO: 24) | AGX19007.1 (SEQ ID NO: 25) |
| | CY187812.1 (SEQ ID NO: 26) | AIC73926.1 (SEQ ID NO: 27) |
| | DQ508913.1 | ABF21279.1 |
| | CY156394.1 | P03463.1 |
| | EU515950.1 | AHW46756.1 |

Immune response: A response of a cell of the immune system, such as a B-cell, T-cell, macrophage or polymorphonucleocyte, to a stimulus such as an antigen or vaccine (such as an influenza A or B HA and/or NA protein). An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like. Other examples are known in the art and provided herein.

Immunize: To render a subject (such as a mammal) protected from an infectious disease (e.g., influenza), such as by vaccination.

Influenza virus: A segmented negative-strand RNA virus that belongs to the Orthomyxoviridae family. There are three types of Influenza viruses, A, B and C.

Influenza A virus (IAV): A negative-sense, single-stranded, segmented RNA virus, which has eight RNA segments (PB2, PB1, PA, NP, M, NS, HA and NA) that code for 11 proteins, including RNA-directed RNA polymerase proteins (PB2, PB1 and PA), nucleoprotein (NP), neuraminidase (NA), hemagglutinin (subunits HA1 and HA2), the matrix proteins (M1 and M2) and the non-structural proteins (NS1 and NS2). This virus is prone to rapid evolution by error-protein polymerase and by segment reassortment. The host range of influenza A is quite diverse, and includes humans, birds (e.g., chickens and aquatic birds), horses, marine mammals, pigs, bats, mice, ferrets, cats, tigers, leopards, and dogs. In animals, most influenza A viruses cause mild localized infections of the respiratory and intestinal tract. However, highly pathogenic influenza A strains, such as H5N1, cause systemic infections in poultry in which mortality may reach 100%. Animals infected with influenza A often act as a reservoir for the influenza viruses and certain subtypes have been shown to cross the species barrier to humans.

Influenza A viruses can be classified into subtypes based on allelic variations in antigenic regions of two genes that encode surface glycoproteins, namely, hemagglutinin (HA) and neuraminidase (NA) which are required for viral attachment and cellular release. There are currently 18 different influenza A virus HA antigenic subtypes (H1 to H18) and 11 different influenza A virus NA antigenic subtypes (N1 to N11). 1-H16 and N1-N9 are found in wild bird hosts and may be a pandemic threat to humans. H17-H18 and N10-N11 have been described in bat hosts and are not currently thought to be a pandemic threat to humans.

Specific examples of influenza A include, but are not limited to: H1N1 (such as 1918 H1N1), H1N2, H1N7, H2N2 (such as 1957 H2N2), H2N1, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6, and H14N5. In one example, influenza A includes those known to circulate in humans such as H1N1, H1N2, H3N2, H7N9, and H5N1.

In animals, most influenza A viruses cause self-limited localized infections of the respiratory tract in mammals and/or the intestinal tract in birds. However, highly pathogenic influenza A strains, such as H5N1, cause systemic infections in poultry in which mortality may reach 100%. In 2009, H1N1 influenza was the most common cause of human influenza. A new strain of swine-origin H1N1 emerged in 2009 and was declared pandemic by the World Health Organization. This strain was referred to as "swine flu." H1N1 influenza A viruses were also responsible for the Spanish flu pandemic in 1918, the Fort Dix outbreak in 1976, and the Russian flu epidemic in 1977-1978.

Influenza B virus (IBV): A negative-sense, single-stranded, RNA virus, which has eight RNA segments. The capsid of IBV is enveloped while its virion includes an envelope, matrix protein, nucleoprotein complex, a nucleocapsid, and a polymerase complex. The surface projection are made of neuraminidase (NA) and hemagglutinin. This virus is less prone to evolution than influenza A, but it mutates enough such that lasting immunity has not been achieved. The host range of influenza B is narrower than influenza A, and is only known to infect humans and seals.

Influenza B viruses are not divided into subtypes, but can be further broken down into lineages and strains. Specific examples of influenza B include, but are not limited to: B/Yamagata, B/Victoria, B/Shanghai/361/2002 and B/Hong Kong/330/2001.

Isolated: An "isolated" biological component (such as a nucleic acid, protein, VLP, or virus) has been substantially separated or purified away from other biological components (such as cell debris, or other proteins or nucleic acids). Biological components that have been "isolated" include those components purified by standard purification methods. The term also embraces recombinant nucleic acids, proteins, viruses and VLPs, as well as chemically synthesized nucleic acids or peptides.

Matrix protein: Influenza A virus has two matrix proteins, M1 and M2. M1 is a structural protein found within the viral envelope. M1 is a bifunctional membrane/RNA-binding protein that mediates the encapsidation of RNA-nucleoprotein cores into the membrane envelope. M1 consists of two domains connected by a linker sequence. The M2 protein is a single-spanning transmembrane protein that forms tetramers having H+ ion channel activity, and when activated by the low pH in endosomes, acidify the inside of the virion, facilitating its uncoating. Homologous proteins in influenza B virus, M1 and BM2, have been described.

The nucleotide and amino acid sequences of numerous influenza A M1 and M2 proteins, as well as influenza B matrix proteins, are known in the art and are publically available, such as those deposited with GenBank®. Exemplary sequences available from GenBank® are provided in Table 2 below (GenBank® accession numbers are provided).

TABLE 2

Exemplary M1 and M2 sequences that can be used in the disclosed VLPs

| Exemplary Nucleic Acid Sequences | Exemplary Protein Sequences |
|---|---|
| CY002697.1 (SEQ ID NO: 19; M1 and M2) | ABA12718.1 (SEQ ID NO: 20; M1) |
| AB189064.1 (M1 and M2) | ABA12719.1 (SEQ ID NO: 21; M2) |
| DQ870897.1 (M1 and M2) | ABS52607.1 (M2) |
| AF231361.1 (M1 and M2) | AAD49068.1 (M2) |
| AY044171.1 (IBV matrix) (SEQ ID NO: 34) | ABQ12378.1 (M2) |
| AY504605.1 (IBV matrix) (SEQ ID NO: 36) | ABS52606.1 (M1) |
| AB120274.1 (IBV matrix) (SEQ ID NO: 38) | ABV53560.1 (M1) |
| AF100382.1 (IBV matrix) | AAD49091.1 (M1) |
| DQ508916.1 (IBV matrix) | AAK95902.1 (IBV matrix) (SEQ ID NO: 35) |
| | AAT69429.1 (IBV matrix) (SEQ ID NO: 37) |
| | BAD29821.1 (IBV matrix) (SEQ ID NO: 39) |
| | ABF21318.1 (IBV matrix) |
| | AHW46771.1 (IBV matrix) |

Neuraminidase (NA): An influenza virus membrane glycoprotein. NA is involved in the destruction of the cellular receptor for the viral HA by cleaving terminal sialic acid residues from carbohydrate moieties on the surfaces of infected cells. NA also cleaves sialic acid residues from viral proteins, preventing aggregation of viruses. NA (along with HA) is one of the two major influenza virus antigenic determinants. The nucleotide and amino acid sequences of numerous influenza NA proteins are known in the art and are publically available, such as those deposited with the GenBank® database.

Exemplary NA sequences (such as IVA NA found in birds) that are available from the GenBank® database are provided in Table 3 below (GenBank® accession numbers are provided).

TABLE 3

Exemplary NA sequences from IAV (N1-N9) or IBV
that can be used to generate the disclosed VLPs

| Antigen | Exemplary Nucleic Acid Sequences | Exemplary Protein Sequences |
|---|---|---|
| N1 | FJ966084.1 (SEQ ID NO: 15) | ACP41107.1 (SEQ ID NO: 16) |
|  | HM006761.1 (SEQ ID NO: 17) | ADD97097.1 (SEQ ID NO: 18) |
| N2 | AF474048.1 | AAO33498.1 |
|  | AY254145.1 | AAP21476.1 |
|  | AY254139.1 | AAP21470.1 |
| N3 | CY187031.1 | AHZ43937.1 |
|  | CY020887.1 | ABO52063.1 |
| N4 | AY207531.1 | AAO62045.1 |
|  | AY207533.1 | AAO62047.1 |
|  | AY207528.1 | AAO62042.1 |
| N5 | M24740.1 | AAA43672.1 |
|  |  | P03478.2 |
|  |  | NMIVAA |
| N6 | AY207557.1 | AAO62071.1 |
|  | AY207556.1 | AAO62070.1 |
|  | AY207553.1 | AAO62067.1 |
| N7 | M38330.1 | AAA43425.1 |
|  |  | P18881.1 |
| N8 | L06575.1 | AAA43404.1 |
|  | AY531038.1 | AAT08005.1 |
|  | CY020903.1 | ABO52085.1 |
| N9 | M17812.1 | AAA43575.1 |
|  | M17813.1 | AAA43574.1 |
|  | AB472040.1 | BAH69263.1 |
| NA from IBV | AB036870.1 (SEQ ID NO: 28) | BAB32609.1 (SEQ ID NO: 29) |
|  | NC_002209.1 (SEQ ID NO: 30) | NP_056663.1 (SEQ ID NO: 31) |
|  | D14855.1 (SEQ ID NO: 32) | BAA03583.1 (SEQ ID NO: 33) |
|  | AJ419110.1 | ACT85965.1 |
|  | AJ784104.1 | AGA18957.1 |
|  | AJ419111.1 | AAO38872.1 |

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Outbreak: As used herein, an influenza virus "outbreak" refers to a collection of virus isolates from within a single country or region in a given year.

Pharmaceutically acceptable vehicles: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compositions, such as one or more influenza VLP compositions disclosed herein, and additional pharmaceutical agents.

Polypeptide or Protein: A polymer in which the monomers are amino acid residues which are joined together through amide bonds. When the amino acids are alpha-amino acids, either the L-optical isomer or the D-optical isomer can be used. The terms "polypeptide" or "protein" encompass any amino acid sequence and include modified sequences such as glycoproteins. The term "residue" or "amino acid residue" includes reference to an amino acid that is incorporated into a protein.

Conservative amino acid substitutions are those substitutions that, when made, least interfere with the properties of the original protein, that is, the structure and especially the function of the protein is conserved and not significantly changed by such substitutions. Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Be for Met; Met, Leu or Tyr for Phe; Thr for Ser; Ser for Thr; Tyr for Trp; Trp or Phe for Tyr; and Ile or Leu for Val.

More substantial changes can be made by using substitutions that are less conservative, e.g., selecting residues that differ more significantly in their effect on maintaining: (a) the structure of the polypeptide backbone in the area of the substitution, for example, as a sheet or helical conformation; (b) the charge or hydrophobicity of the polypeptide at the target site; or (c) the bulk of the side chain. The substitutions that in general are expected to produce the greatest changes in polypeptide function are those in which: (a) a hydrophilic residue, e.g., serine or threonine, is substituted for (or by) a hydrophobic residue, e.g., leucine, isoleucine, phenylalanine, valine or alanine; (b) a cysteine or proline is substituted for (or by) any other residue; (c) a residue having an electropositive side chain, e.g., lysine, arginine, or histidine, is substituted for (or by) an electronegative residue, e.g., glutamic acid or aspartic acid; or (d) a residue having a bulky side chain, e.g., phenylalanine, is substituted for (or by) one not having a side chain, e.g., glycine. The effects of these amino acid substitutions (or other deletions or additions) can be assessed by analyzing the function of the mutant protein, such as a mutant HA or NA protein, by analyzing the ability of the variant protein to stimulate an immune response.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Promoter: A promoter is an array of nucleic acid control sequences which direct transcription of a nucleic acid, such as a nucleic acid encoding an influenza HA, NA, or matrix (e.g., M1, or M2) protein. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor). In some examples, the promoter is a CMV promoter or an SV40 promoter.

Purified: The term "purified" does not require absolute purity; rather, it is intended as a relative term. Thus, for example, a purified protein, virus, VLP or other compound is one that is isolated in whole or in part from naturally associated proteins and other contaminants. In certain embodiments, the term "substantially purified" refers to a protein, virus, VLP or other active compound that has been isolated from a cell, cell culture medium, or other crude preparation and subjected to fractionation to remove various components of the initial preparation, such as proteins, cellular debris, and other components.

Recombinant: A recombinant nucleic acid, protein, virus or VLP is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a given gene or protein will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237-244, 1988; Higgins and Sharp, *CABIOS* 5:151-153, 1989; Corpet et al., *Nucleic Acids Research* 16:10881-10890, 1988; and Pearson and Lipman, *Proc. Natl. Acad. Sci. U.S.A.* 85:2444, 1988. Altschul et al., *Nature Genet.* 6:119-129, 1994.

The NCBI Basic Local Alignment Search Tool (BLAST™) (Altschul et al., *J. Mol. Biol.* 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx.

Variants of the disclosed influenza HA, NA, M1 and M2 proteins and coding sequences disclosed herein are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided. Thus, a variant influenza HA, NA, or matrix protein (or coding sequence) can have at least 80%, at least 85%, at least 90%, at least 91%, at least 92%, at least 95%, at least 96%, at least 97%, at least 98% or at least 99% sequence identity to any of SEQ ID NOS: 1-39 (as well as such sequence identity to any GenBank® Accession No. provided in Tables 1-3), and can be used in the methods and compositions provided herein.

Subject: Living multi-cellular vertebrate organisms, a category that includes both human and non-human mammals, such as non-human primates. In one example a subject is one that can be infected with influenza A or B, such as humans, birds (e.g., chickens, turkeys), horses, pigs, bats, mice, ferrets, cats, tigers, leopards, seals, and dogs.

Therapeutically effective amount: A quantity of a specified agent sufficient to achieve a desired effect in a subject being treated with that agent. For example, this may be the amount of a polyvalent VLP composition useful for eliciting an immune response in a subject and/or for preventing infection or disease caused by influenza virus. In one example, a therapeutically effective amount of a polyvalent VLP composition is an amount sufficient to increase resistance to, prevent, ameliorate, and/or treat infection caused by influenza virus (such as influenza A, influenza B, or both) in a subject without causing a substantial cytotoxic effect in the subject. The effective amount of a polyvalent VLP composition useful for increasing resistance to, preventing, ameliorating, and/or treating infection in a subject will be dependent on, for example, the subject being treated, the manner of administration of the therapeutic composition and other factors.

Transformed: A transformed cell is a cell into which has been introduced a nucleic acid molecule by, for example, molecular biology techniques. As used herein, the term transformation encompasses all techniques by which a nucleic acid molecule might be introduced into such a cell, including transfection with viral vectors (such as baculovirus), transformation with plasmid vectors, and introduction of naked DNA by electroporation, lipofection, and particle gun acceleration.

Vaccine: A preparation of immunogenic material capable of stimulating an immune response, administered for the prevention, amelioration, or treatment of disease, such as an infectious disease. The immunogenic material may include a polyvalent VLP composition disclosed herein. Vaccines may elicit both prophylactic (preventative) and therapeutic responses. Methods of administration vary according to the vaccine, but can include inoculation, ingestion, intranasal or other forms of administration. Vaccines may be administered with an adjuvant to enhance the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of an inserted gene or genes. In some embodiments of the present disclosure, the vector encodes an influenza HA, NA, M1 or M2 protein. In some embodiments, the vector is the pCAGGS expression vector or the pFastBacl baculovirus transfer vector plasmid.

Virus-like particle (VLP): Enveloped structures resembling viruses made up of one of more viral structural proteins, but which lack the viral genome. Because VLPs lack a viral genome, they are non-infectious. In addition, VLPs can be produced by heterologous expression and purified. The VLPs provided herein express or include HA or NA proteins, and can further include a viral core protein that drives budding and release of particles from a host cell (such as influenza M1, M2 or both). When referring to a VLP that expresses an HA or NA protein, this indicates that the VLPs present properly folded, functional, multimerized versions of HA (or NA). For example, VLPs expressing HA can bind receptors on epithelial cells or red blood cells, and VLPs expressing NA have enzymatic activity to cleave sialic acids. Exemplary images of VLPs are provided in FIGS. 2A-2C.

In some embodiments herein, an influenza VLP expresses or includes an influenza A HA or influenza A NA protein, in combination with influenza A M1, influenza A M2, or both influenza A M1 and influenza A M2 proteins. In other embodiments herein, an influenza VLP expresses or includes an influenza B HA or influenza B NA protein, in combination with influenza B matrix protein M1 or both influenza B M1 and BM2 proteins. Influenza VLPs can be produced by transfection of host cells with plasmids encoding the HA or NA protein, and optionally the matrix protein (e.g., M1, M2 or M1 and M2 proteins). After incubation of the transfected cells for an appropriate time to allow for protein expression (such as for approximately 72 hours), VLPs can be isolated from cell culture supernatants.

Overview

Influenza A is responsible for up to half a million deaths worldwide each year. Although several subtypes commonly circulate in humans, new subtypes can be introduced at any time through zoonotic infection, such as H5N1 or H7N9. Even though the seasonal vaccine is updated every year, these zoonotic transmissions are unpredictable and not accounted for in the vaccine. Currently available vaccines are not sufficient because (1) inactivated IM vaccines do not generate a robust mucosal immune response, and (2) live attenuated influenza vaccines (LAIV) are problematic because they are over-attenuated, have restricted usage guidelines, and LAIV with HA and NA subtypes not present in seasonal strains cannot be used because of the risk of reassortment with wild type viruses. Currently available vaccines are designed to be protective against specific strains and reformulated every year and do not provide universal protection. Specific pre-pandemic vaccines, both inactivated and LAIV, against avian influenza viruses have not been very immunogenic. A universal vaccine aimed to stem zoonotic influenza infections from becoming pandemics could supplement the current seasonal vaccine and would be beneficial to public health. In some examples, a universal vaccine protects against all 16 avian HA subtypes (H1 to H16) and can be manufactured quickly in the event of a pandemic.

The current disclosure provides a polyvalent VLP vaccine strategy that can be delivered intranasally to elicit broadly reactive immunity to conserved epitopes on the influenza virus HA head and stalk as well as to NA epitopes and thus to confer protection to a wide range of influenza A viruses. Although HA is antigenically diverse, conserved epitopes in the HA receptor binding and stalk domains can allow cross-reactive vaccines to be produced. In one example, the disclosed compositions (e.g., vaccines) include a polyvalent mixture of influenza VLPs each containing a single influenza A HA subtype (or a single NA subtype) to avoid problem of immunodominance of HA over NA. In some examples the compositions further include VLPs containing influenza A NA proteins (e.g., additional VLPs or VLP populations express a single NA subtype). In some examples, the VLPs also contain influenza A matrix proteins, such as M1, M2, or both. Intranasal delivery or administration is used to induce mucosal and systemic immunity. These polyvalent VLPs are non-infectious, safe, and easy to manufacture and use. These polyvalent VLPs can be used to provide a broadly protective 'universal' pre-pandemic vaccine and a more broadly reactive seasonal vaccine.

In another example, the disclosed compositions (e.g., vaccines) include a polyvalent mixture of influenza VLPs each containing a single HA subtype from influenza A or B. In some examples the compositions further include VLPs containing influenza A or B NA proteins (e.g., additional VLP populations each expressing an influenza A NA subtype or influenza B NA). In some examples, the VLPs also contain influenza A or B matrix proteins (e.g., VLPs expressing influenza A NA or HA can further express influenza A M1, M2 or both, while VLPs expressing influenza B NA or HA can further express an influenza B matrix protein, such as influenza B M1, BM2, or both). Intranasal delivery or administration is used to induce mucosal and systemic immunity. These polyvalent VLPs are non-infectious, safe, and easy to manufacture and use. These polyvalent VLPs (which include mixtures of VLP populations expressing influenza A or B HA), can be used to provide a broadly reactive seasonal vaccine.

It is shown herein that mice vaccinated intranasally (to induce mucosal and systemic immunity) with monovalent HA VLPs were protected from heterologous lethal challenge. Additionally, mice that were vaccinated with a TLR agonist as an adjuvant exhibited reduced morbidity compared to those that received vaccine alone. Polyvalent VLP mixtures can thus be used for protection against lethal influenza A viruses such as 1918 H1N1, 1957 H2, 2004 H5N1, and 2013 H7N9.

Polyvalent VLP Compositions

Provided herein are compositions that contain two or more different influenza virus-like particles (VLPs), such as two or more different VLP populations. Such compositions are referred to as influenza polyvalent VLPs (or polyvalent VLP-containing compositions). For example, the compositions can include VLPs expressing different influenza hemagglutinin (HA) polypeptides, such as a first VLP that contains (or expresses) a first HA polypeptide, and a second VLP that contains (or expresses) a second HA polypeptide, wherein the first and second HA polypeptides are different subtypes (or are from different influenza viruses, such as influenza A and B). Thus, the composition can contain a plurality of different VLPs, each expressing or containing a different HA subtype or HA from a different influenza (e.g., A and B). Such compositions, in addition to the VLPs, can include other reagents, such as a pharmaceutically acceptable carrier and/or an adjuvant.

In one example, the composition includes at least two different VLPs, such as at least two different populations of VLPs, each VLP or VLP population containing one HA subtype (or containing an HA from one influenza virus, such as influenza A and B). For example, as shown in FIG. 1A, composition 100 can include a first VLP 102 that contains a first HA subtype (H-X) and a second VLP 104 that contains a different HA subtype (H-Y). Thus, in one example, the first VLP 102 can contain a first HA from influenza B (H-X) and the second VLP 104 can contain a second but different HA from influenza B (H-Y), or the first VLP 102 can contain a first HA from influenza A (H-X) and the second VLP 104 can contain a second but different HA from influenza A (H-Y). Alternatively, the first VLP 102 can contain a first HA from influenza A (H-X) and the second VLP 104 can contain a second HA from influenza B (H-Y). Each VLP 102 and 104 can contain a plurality of VLPs, each population 102, 104 containing a different HA subtype (or HA from a different influenza virus).

One skilled in the art will appreciate that more than two different VLPs can be included in the composition 100. Thus, the composition can include at least 2, at least 3, at least 4, at least 5, at least 6, at least 7, at least 8, at least 9, or at least 10, such as 2, 3, 4, 5, 6, 7, 8, 9, 10, 11, 12, 13, 14, 15, 16, 17, or 18 different VLPs or VLP populations, each expressing a different influenza HA subtype and/or from a different influenza virus, such as 2-8, 2-6, 5-6, or 4-6 different VLPs or VLP populations (wherein each VLP or VLP population has a different HA protein subtype and/or HA from a different virus). For example, a first VLP can express a first influenza A HA polypeptide selected from the group consisting of HA subtype H1, H2, H3, H4, H5, H6, H7, H8, H9, H10, H11, H12, H13, H14, H15 and H16; while a second VLP can express a second influenza A HA polypeptide selected from the group consisting of HA subtype H1, H2, H3, H4, H5, H6, H7, H8, H9, H10, H11, H12, H13, H14, H15 and H16, wherein the first and the second HA polypeptide are different subtypes. Thus, if the composition included a third VLP, such as a third VLP population, the third influenza A HA polypeptide would be selected from the group consisting of HA subtype H1, H2, H3, H4, H5, H6, H7, H8, H9, H10, H11, H12, H13, H14, H15 and H16, wherein the third HA polypeptide subtype is different from the first and the second HA polypeptide subtypes.

In another example, a first VLP can express a first influenza A HA polypeptide selected from the group consisting of HA subtype H1, H2, H3, H4, H5, H6, H7, H8, H9, H10, H11, H12, H13, H14, H15 and H16; while a second VLP can express a first influenza B HA polypeptide such as Yamagata-like or Victoria-like antigens. If the composition included a third VLP, such as a third VLP population containing a second influenza A HA polypeptide, it would be selected from the group consisting of HA subtype H1, H2, H3, H4, H5, H6, H7, H8, H9, H10, H11, H12, H13, H14, H15 and H16, wherein the second influenza A HA polypeptide subtype is different from the first influenza A HA polypeptide subtype. If the composition included a third VLP, such as a third VLP population containing a second influenza B HA polypeptide, the second influenza B HA would be different from the first influenza B HA. In a specific example, the composition includes at least two, at least three, at least four, at least five, such as 2, 3, 4, 5, 6, 7, 8, 9 or 10 different VLPs (or VLP populations), wherein at least one VLP population includes an influenza A HA subtype, at least one VLP population includes an influenza B HA, and optionally at least one VLP population includes an influenza A NA subtype.

In one example, the composition includes separate VLPs (or VLP populations), wherein a first VLP population expresses influenza A H1, a second VLP population expresses influenza A H3, a third VLP population expresses influenza A H5, a fourth VLP population expresses influenza A H7, a fifth VLP population expresses influenza A N1, a sixth VLP population expresses influenza A N2, a seventh VLP population expresses influenza B Yamagata-like or Victoria-like antigen, and optionally an eighth VLP population expresses influenza B Yamagata-like or Victoria-like antigen (that is different from the seventh VLP population. Such a composition can be used as a seasonal vaccine or as a prepandemic vaccine.

Phylogenetically, there are two major groups of influenza A virus HAs: group 1 contains H1, H2, H5, H6, H8, H9, H11, H12, H13, and H16, and group 2 contains H3, H4, H7, H10, H14, and H15 subtypes. Thus, in one example, the composition includes a first VLP or first population of VLPs expressing at least one HA polypeptide of Group 1 (i.e., H1, H2, H5, H6, H8, H9, H11, H12, H13, or H16), and a second VLP or second population of VLPs expressing at least one HA polypeptide of Group 2 (i.e., H3, H4, H7, H10, H14, or H15). In another example, the composition includes at least two different VLPs or different populations of VLPs, each expressing a different HA polypeptide of Group 1 (i.e., H1, H2, H5, H6, H8, H9, H11, H12, H13, or H16). In another example, the composition includes at least two different VLPs or different populations of VLPs, each expressing a different HA polypeptide of Group 2 (i.e., H3, H4, H7, H10, H14, or H15). Similarly, while influenza B virus HA does not have distinct subtypes, there are two major antigenic lineages, Victoria-like and Yamagata-like that are also phylogenetically distinct.

In a specific example, the composition includes at least two, at least three, at least four, at least five, such as 2, 3, 4, 5, 6, 7, 8, 9 or 10 different VLPs (or VLP populations), each containing a different influenza A HA polypeptide of Group 1 (i.e., H1, H2, H5, H6, H8, H9, H11, H12, H13, or H16). In a specific example, the composition includes at least two, at least three, at least four, at least five, at least six, such as 2, 3, 4, 5, or 6, different VLPs (or VLP populations), each containing a different influenza A HA polypeptide of Group 2 (i.e., H3, H4, H7, H10, H14, or H15).

In a specific example, the first influenza A HA polypeptide is HA subtype H1, H2 or H5 and the second influenza A HA polypeptide is HA subtype H3, H7 or H9. In another specific example, the first influenza A HA polypeptide is HA subtype H1, H2, H3, H5, H7 or H9 and the second influenza A HA polypeptide is HA subtype H1, H2, H3, H5, H7 or H9, wherein the first and the second HA polypeptide are different subtypes. In yet other specific examples, (i) the first influenza A HA polypeptide is HA subtype H2 and the second influenza A HA polypeptide is HA subtype H5; (ii) the first influenza A HA polypeptide is HA subtype H3 and the second influenza A HA polypeptide is HA subtype H7; (iii) the first influenza A HA polypeptide is HA subtype H1 and the second influenza A HA polypeptide is HA subtype H3; (iv) the first influenza A HA polypeptide is HA subtype H2 and the second influenza A HA polypeptide is HA subtype H7; (v) the first influenza A HA polypeptide is HA subtype H5 and the second influenza A HA polypeptide is HA subtype H3; or (vi) the first influenza A HA polypeptide is HA subtype H1 and the second influenza A HA polypeptide is HA subtype H7.

In a specific example, the composition includes at least four different populations of VLPs, wherein the first population of VLPs comprises influenza A HA subtype H1, the second population of VLPs comprises influenza A HA subtype H3, the third population of VLPs comprises influenza A HA subtype H5, and the fourth population of VLPs comprises influenza A HA subtype H7. In some examples, the composition further includes a fifth population of VLPs comprising influenza A HA subtype H9. In some examples, the composition further includes a sixth population of VLPs comprising an influenza A NA, such as N1 or N2. In some examples, the composition further includes a seventh and eighth population of VLPs comprising influenza A NA N1 (seventh population) and N2 (eighth population). Such VLPs in some examples also include M1 and M2.

Figure 1B:
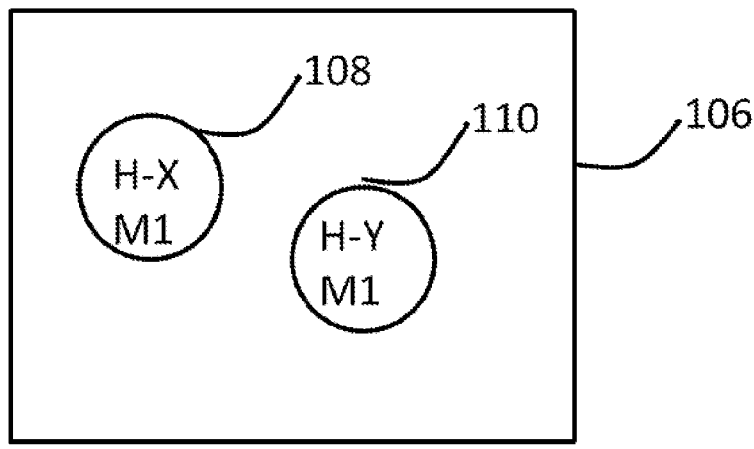

The VLPs of the disclosure in addition to having an HA protein, can also express an influenza matrix protein (e.g., influenza A M1, influenza A M2, or both). As shown in FIG. 1B, the composition 106 can include a VLP or VLP population 108 having a first HA subtype H-X and matrix protein M1 and VLP or VLP population 110 having a second HA subtype H-Y and matrix protein M1. M2 can also be present in VLP 108 and/or VLP 110. Alternatively, the VLP or VLP population 108 can contain a first HA from influenza A (H-X) and an influenza A matrix protein M1 (M2 can also be present) and the second VLP or VLP population 110 can contain a second HA from influenza B (H-Y) and an influenza B matrix protein M1.

Figure 1C:
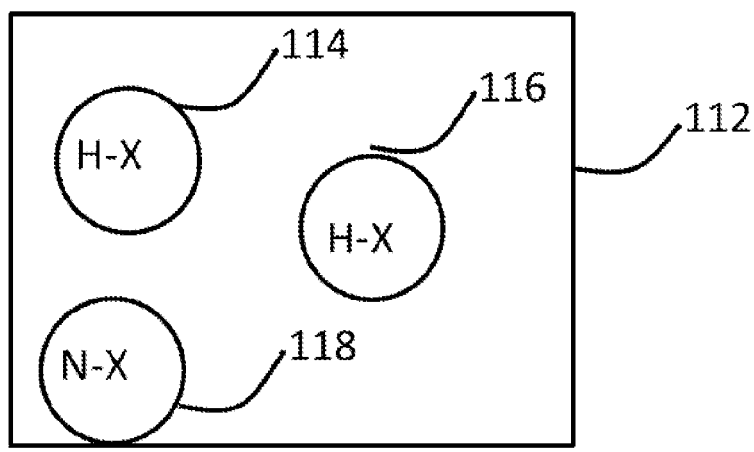

The disclosed compositions, in addition to including VLPs expressing HA, can include a VLP (or population of VLPs) that expresses an influenza neuraminidase (NA) polypeptide. In some examples, the composition includes two or more different VLPs or VLP populations, each having a different influenza NA polypeptide. Thus, the composition can further include a first VLP comprising a first influenza NA polypeptide, a second VLP comprising a second influenza NA polypeptide, or both, wherein the first and the second NA polypeptide are different subtypes or are from different influenza viruses. For example, as shown in FIG. 1C, composition 112 includes VLP or VLP populations 114 and 116, each having a different HA subtype (or NA from a different influenza virus), and further includes VLP or VLP population 118 having NA subtype N-X. The VLPs 114, 116, 118 can also include an influenza matrix protein (i.e., M1, M2, or both).

Phylogenetically, there are two groups of influenza A virus NAs that form two groups: group 1 contains N1, N4, N5, and N8, and group 2 contains N2, N3, N6, N7, and N9. Thus, in one example, the polyvalent VLP-containing composition further includes a first VLP or first population of VLPs containing at least one NA polypeptide of Group 1 (i.e., N1, N4, N5, or N8), and a second VLP or second population of VLPs containing at least one NA polypeptide of Group 2 (i.e., N2, N3, N6, N7, or N9). In another example, the polyvalent VLP-containing composition further includes at least two different VLPs or different populations of VLPs, each containing a different NA polypeptide of Group 1 (i.e., N1, N4, N5, or N8). In another example, the polyvalent VLP-containing composition further includes at least two different VLPs or different populations of VLPs, each containing a different NA polypeptide of Group 2 (i.e., N2, N3, N6, N7, or N9).

In a specific example, the polyvalent VLP-containing composition further includes 1, 2, 3, or 4 different VLPs (or VLP populations), each containing a different NA polypeptide of Group 1 (i.e., N1, N4, N5, and N8). In a specific example, the composition includes 1, 2, 3, 4, or 5, different VLPs (or VLP populations), each containing a different NA polypeptide of Group 2 (i.e., N2, N3, N6, N7, or N9).

Similarly, while influenza B virus NA does not have distinct subtypes, there are two major antigenic lineages, Victoria-like and Yamagata-like that are also phylogenetically distinct. Thus, in one example, the polyvalent VLP-containing composition further includes a first VLP or first population of VLPs containing at least one influenza B NA polypeptide (e.g., Victoria-like), and a second VLP or second population of VLPs containing at least one influenza B NA polypeptide (e.g., Yamagata-like).

The NA-VLPs of the disclosure in addition to having an NA protein, can also include an influenza matrix protein (e.g., influenza A M1, influenza A M2, or both; or influenza B M1, influenza B BM2, or both).

The disclosed compositions can, in addition to the VLPs, further include one or more adjuvants, such as lipid A monophosphoryl (MPL), Flt3 ligand, immunostimulatory oligonucleotides (such as CpG oligonucleotides), or combinations thereof.

In some examples, the disclosed compositions are formulated for intranasal administration, for example for mucosal immunization.

Also provided are vials or syringes (such as one having an atomizer) containing the polyvalent VLPs provided herein. In some examples, the disclosed VLP-containing compositions are freeze-dried or lyophilized.

The disclosed polyvalent VLP-containing compositions can also be part of a kit. For example, the kit can include containers or vials, which in some examples each contain a different VLP. The VLPs in the containers can be in a suspension, such as with PBS or other pharmaceutically acceptable carrier. Alternatively, the VLPs can be in a dried or powered form, such as lyophilized or freeze dried, which can then be reconstituted by an end user (for example with PBS or other pharmaceutically acceptable carrier). For example a first container can include VLPs that have a first HA subtype (or HA from a first influenza virus), and a second container can include VLPs with a second HA subtype (or HA from a second influenza virus). In some example, a third container can include VLPs with a first NA subtype, and so forth. In some examples, the containers include a mixture of VLPs provided herein. The containers in the kit can include an adjuvant, or the adjuvant can be in a separate container in the kit. In some examples the containers can include a pharmaceutically acceptable carrier, such as PBS, or the pharmaceutically acceptable carrier, such as PBS, can be in a separate container (for example if the VLPs are freeze-dried or lyophilized). In some examples, the containers in the kit further include one or more stabilizers. In some examples, the kits also include a device that permits administration of the VLPs to a subject. Examples of such devices include a syringe or syringe atomizer (for example an MAD® nasal drug delivery device, such as those from Life Medicals Supplier, Sunrise, Fla.).

In one example, the kit includes a first population of VLPs comprising influenza A HA subtype H1, a second population of VLPs comprising influenza A HA subtype H3, a third population of VLPs comprising influenza A HA subtype H5, and a fourth population of VLPs comprising influenza A HA subtype H7. In some examples, the kit further or optionally includes a fifth population of VLPs comprising influenza A HA subtype H9. In some examples, the kit further includes a sixth population of VLPs comprising an influenza A NA, such as N1 or N2. In some examples, the kit further includes a sixth and seventh population of VLPs comprising influenza A NA N1 (sixth population) and N2 (seventh population). In some examples, the kit further includes a eighth VLP population that expresses influenza B Yamagata-like or Victoria-like antigen, and optionally a ninth VLP population expresses influenza B Yamagata-like or Victoria-like antigen (that is different from the eighth VLP population). Such a composition can be used as a seasonal vaccine or as a prepandemic vaccine.

Such VLPs in some examples also include M1 and M2. Such VLP populations in the kit in some examples are in separate containers, or can be combined in a single container (such as in a vial or syringe).

1. Hemagglutinin (HA)

HA is a viral surface glycoprotein, expressed as a homotrimer, generally representing about 25% of the total virus protein. It is responsible for adhesion of the viral particle to, and its penetration into, a host cell in the early stages of infection. Cleavage of the virus HA0 precursor into the HA1 and HA2 sub-fragments is required for the virus to infect a cell. Thus, cleavage is required to convert new virus particles in a host cell into virions capable of infecting new cells. Cleavage occurs during transport of the integral HA0 membrane protein from the endoplasmic reticulum of the infected cell to the plasma membrane. In the course of transport, HA undergoes a series of co- and post-translational modifications including proteolytic cleavage of the precursor HA into the amino-terminal fragment HA1 and the carboxy terminal HA2.

The HA peptide sequence present in a VLP provided herein can be an influenza A HA sequence, such as an avian HA sequence, or an influenza B HA sequence. In specific examples, the influenza A HA peptide sequence present in a VLP provided herein has at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 2, SEQ ID NO: 4, SEQ ID NO: 6, SEQ ID NO; 8, SEQ ID NO: 10, SEQ ID NO: 12, or SEQ ID NO: 14, or to any of the amino acid sequences provided in Table 1 by its GenBank® Accession No. In specific examples, the influenza B HA peptide sequence present in a VLP provided herein has at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 23, SEQ ID NO: 25, or SEQ ID NO: 27, or to any of the amino acid sequences provided in Table 1 by its GenBank® Accession No. In some examples, the HA peptide in the VLP does not include the signal sequence (that is about amino acids 1-15, 1-16, 1-17, 1-18, or 1-19 of the pre-processed HA protein sequence). Thus, in some examples, the HA peptide sequence present in a VLP provided herein can be an amino acid sequence having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to the mature form of SEQ ID NO: 2, SEQ ID NO: 4, SEQ ID NO: 6, SEQ ID NO; 8, SEQ ID NO: 10, SEQ ID NO: 12, SEQ ID NO: 14, SEQ ID NO: 23, SEQ ID NO: 25, or SEQ ID NO: 27 or the mature form of any of the amino acid sequences provided in Table 1 by its GenBank® Accession No. (that is, without the signal sequence).

In one example, the HA polypeptide is H1. In some examples H1 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 2; or at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 4. In some examples H1 present in a VLP has an amino acid sequence that includes SEQ ID NO: 2, consists of SEQ ID NO: 2, includes SEQ ID NO: 4, or consists of SEQ ID NO: 4. In some examples H1 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 18-566 of SEQ ID NO: 2; or at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 20-566 of SEQ ID NO: 4.

In one example, the HA polypeptide is H2. In some examples H2 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 6; at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 8. In some examples H2 present in a VLP has an amino acid sequence that includes SEQ ID NO: 6, consists of SEQ ID NO: 6, includes SEQ ID NO: 8, or consists of SEQ ID NO: 8. In some examples H2 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 16-562 of SEQ ID NO: 6; or at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 16-562 of SEQ ID NO: 8.

In one example, the HA polypeptide is H3. In some examples H3 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 10. In some examples H3 present in a VLP has an amino acid sequence that includes SEQ ID NO: 10, or consists of SEQ ID NO: 10. In some examples H3 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 17-566 of SEQ ID NO: 10.

In one example, the HA polypeptide is H5. In some examples H5 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 12. In some examples H5 present in a VLP has an amino acid sequence that includes SEQ ID NO: 12, or consists of SEQ ID NO: 12. In some examples H5 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 17-564 of SEQ ID NO: 12.

In one example, the HA polypeptide is H7. In some examples H7 present in a VLP has an amino acid sequence that is or at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 14. In some examples H7 present in a VLP has an amino acid sequence that includes SEQ ID NO: 14, or consists of SEQ ID NO: 14. In some examples H7 present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 19-560 of SEQ ID NO: 14.

In one example, the HA polypeptide is from influenza B. In some examples the HA present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 23; at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 25; or at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 27. In some examples HA present in a VLP has an amino acid sequence that includes SEQ ID NO: 23, consists of SEQ ID NO: 23, includes SEQ ID NO: 25, consists of SEQ ID NO: 25, includes SEQ ID NO: 27, or consists of SEQ ID NO: 27. In some examples HA present in a VLP has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 18-583 of SEQ ID NO: 23; at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 18-585 of SEQ ID NO: 25; or at least 80%, at least 85%, at least 90%, at least 92%, at least 95%, at least 96%, at least 96.5%, at least 97%, at least 97.5%, at least 98%, at least 98.5%, at least 99% or at least 99.5% identical to residues 18-584 of SEQ ID NO: 27.

In other embodiments, the HA amino acid sequence in the VLP has no more than 2, no more than 3, no more than 4, no more than 5, no more than 6, no more than 7, no more than 8, no more than 9, no more than 10, no more than 15, no more than 20, no more than 40, or no more than 50 amino acid substitutions (such as conservative amino acid substitutions) relative to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 23, SEQ ID NO: 25, SEQ ID NO: 27, or to any of the amino acid sequences provided in Table 1 by its GenBank® Accession No. For example, the amino acid sequence of the HA polypeptide present in a VLP can in some examples have 2 to 20, 2 to 15, 1 to 10, 2 to 20, 5 to 40, 5 to 50, 5 to 15, or 5 to 10 amino acid substitutions (such as conservative amino acid substitutions) relative to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 23, SEQ ID NO: 25, SEQ ID NO: 27, or to any of the amino acid sequences provided in Table 1 by its GenBank® Accession No.

In other embodiments, the amino acid sequence of the HA polypeptide comprises (i) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 2; (ii) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 4; (iii) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 6; (iv) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 8; (v) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 10; (vi) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 12; (vii) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 14; (viii) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 23; (ix) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 25; (x) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 27; or (x) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to any of the amino acid sequences provided in Table 1 by its GenBank® Accession No.

Such variant HA sequences (for example when part of a VLP) retain their ability to induce an immune response when administered to a subject, such as a mammal or bird.

In some examples, the influenza HA polypeptide in the VLP comprises or consists of the amino acid sequence of residues 18-566 of SEQ ID NO: 2, residues 20-566 of SEQ ID NO: 4, residues 16-562 of SEQ ID NO: 6, residues 16-562 of SEQ ID NO: 8 residues 17-566 of SEQ ID NO: 10, residues 17-564 of SEQ ID NO: 12, residues 19-560 of SEQ ID NO: 14, residues 18-583 of SEQ ID NO: 23, residues 18-585 of SEQ ID NO: 25, residues 18-584 of SEQ ID NO: 27, or the amino acid sequences provided in Table 1 by its GenBank® Accession No. without the signal peptide sequence.

In other examples, the HA polypeptide in the VLP comprises or consists of the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 23, SEQ ID NO: 25, SEQ ID NO: 27, or any of the amino acid sequences provided in Table 1 by its GenBank® Accession No.

Further provided are isolated nucleic acid molecules encoding the recombinant HA polypeptides disclosed herein. In some embodiments, the nucleic acid molecule is codon-optimized for expression in mammalian or insect cells. The nucleic acid molecule can be further optimized for RNA stability. Based on the HA protein sequences provided, using routine skill nucleic acid molecules can be designed. Furthermore, exemplary HA coding sequences are provided herein. In one example, an HA coding sequence used to generate a VLP provided herein can be a nucleic acid sequence having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 22, SEQ ID NO: 24, SEQ ID NO: 26, or to any of the nucleic acid sequences provided in Table 1 by its GenBank® Accession No. In some examples, the HA coding sequence used to generate a VLP provided herein can be a nucleic acid encoding an HA protein with no more than 2, no more than 3, no more than 4, no more than 5, no more than 6, no more than 7, no more than 8, no more than 9, no more than 10, no more than 15, no more than 20, no more than 40, or no more than 50 amino acid substitutions (such as conservative amino acid substitutions) relative to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 22, SEQ ID NO: 24, SEQ ID NO: 26, or to any of the amino acid sequences provided in Table 1 by its GenBank® Accession No. For example, the HA coding sequence used to generate a VLP provided herein can be a nucleic acid encoding an HA protein having 2 to 20, 2 to 15, 1 to 10, 2 to 20, 5 to 40, 5 to 50, 5 to 15, or 5 to 10 amino acid substitutions (such as conservative amino acid substitutions) relative to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 22, SEQ ID NO: 24, SEQ ID NO: 26, or to any of the amino acid sequences provided in Table 1 by its GenBank® Accession No.

Vectors that include these nucleic acid molecules encoding recombinant HA polypeptides are also provided by the present disclosure. The vector can be any suitable vector for expression of the HA polypeptide, such as a mammalian expression vector or a baculovirus vector. In particular examples, the vector the pCAGGS expression vector or the pFastBacl baculovirus transfer vector plasmid. One skilled in the art will appreciate that any expression vector used for transfection or baculovirus expression can be used.

In some examples, the vector includes a promoter operably linked to the nucleic acid sequence encoding the HA polypeptide. In particular examples, the promoter is a CMV or SV40 promoter.

Also provided are isolated cells that include the disclosed HA-expressing. In some cases, the cell is any suitable cell type for production and expression of VLPs, such as a mammalian cell or insect cell.

2. Neuraminidase (NA)

Neuraminidase (NA) is a second membrane glycoprotein of the influenza viruses, expressed as a homotetramer. Nine different NA subtypes have been identified in influenza viruses from birds (N1, N2, N3, N4, N5, N6, N7, N8 and N9), and while no distinct NA subtypes exist in influenza B viruses, two major antigenic lineages circulate in humans (Yamagata-like and Victoria-like). NA is involved in the destruction of the cellular receptor for the viral HA by cleaving terminal neuraminic acid (also called sialic acid) residues from carbohydrate moieties on the surfaces of infected cells. NA also cleaves sialic acid residues from viral proteins, preventing aggregation of viruses. Using this mechanism, it is hypothesized that NA facilitates release of viral progeny by preventing newly formed viral particles from accumulating along the cell membrane, as well as by promoting transportation of the virus through the mucus present on the mucosal surface.

The NA peptide sequence present in a VLP provided herein can be an influenza A NA sequence, such as an avian NA sequence, or an influenza B sequence. In specific examples, the NA peptide sequence present in a VLP provided herein has at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 16, SEQ ID NO: 18, SEQ ID NO: 29, SEQ ID NO: 31, SEQ ID NO: 33, or to any of the amino acid sequences provided in Table 3 by its GenBank® Accession No.

In particular embodiments, the influenza NA polypeptide is an N1 polypeptide. In some examples, an N1 polypeptide has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 16; is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 18; includes SEQ ID NO: 16, consists of SEQ ID NO: 16, includes SEQ ID NO: 18, or consists of SEQ ID NO: 18.

In particular embodiments, the influenza NA polypeptide is an N2, N3, N4, N5, N6, N7, N8, or N9 polypeptide, and has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to any of the sequences associated with the GenBank Accession Nos. shown in Table 3, includes any of the sequences associated with the GenBank Accession Nos. shown in Table 3, or consists of any of the sequences associated with the GenBank Accession Nos. shown in Table 3.

In particular embodiments, the influenza NA polypeptide is an influenza B NA polypeptide. In some examples, an influenza B NA polypeptide has an amino acid sequence that is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 29; is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 31; is at least 80%, at least 85%, at least 90%, at least 92%, at least 95%, at least 96%, at least 96.5%, at least 97%, at least 97.5%, at least 98%, at least 98.5%, at least 99% or at least 99.5% identical to SEQ ID NO: 33; includes SEQ ID NO: 29, consists of SEQ ID NO: 29, includes SEQ ID NO: 31, consists of SEQ ID NO: 31, includes SEQ ID NO: 33, or consists of SEQ ID NO: 33.

In other embodiments, the amino acid sequence of the NA polypeptide present in a VLP has no more than 2, no more than 3, no more than 4, no more than 5, no more than 6, no more than 7, no more than 8, no more than 9, no more than 10, no more than 20, or no more than 40 amino acid substitutions (such as conservative amino acid substitutions) relative to SEQ ID NO: 16 or SEQ ID NO: 18 or to any of the amino acid sequences provided in Table 3 by its GenBank® Accession No. For example, the amino acid sequence of the NA polypeptide present in a VLP can in some examples have 2 to 20, 2 to 15, 1 to 10, 2 to 20, 5 to 40, 5 to 50, 5 to 15, or 5 to 10 amino acid substitutions (such as conservative a amino acid substitutions) relative to SEQ ID NO: 16 or SEQ ID NO: 18 or to any of the amino acid sequences provided in Table 3 by its GenBank® Accession No. In other embodiments, the amino acid sequence of the NA polypeptide comprises (i) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 16; (ii) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 18; (iii) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 29; (iv) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 31; (v) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 33; or (vi) no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to any of the amino acid sequences provided in Table 3 by its GenBank® Accession No.

Such variant NA sequences (for example when part of a VLP) retain their ability to induce an immune response when administered to a subject, such as a mammal or bird.

In some examples, the influenza NA polypeptide comprises or consists of SEQ ID NO: 16, SEQ ID NO: 18, SEQ ID NO: 29, SEQ ID NO: 31, SEQ ID NO: 33.

Further provided are isolated nucleic acid molecules encoding the NA polypeptides disclosed herein. In some embodiments, the nucleic acid molecule is codon-optimized for expression in mammalian or insect cells. The nucleic acid molecule can be further optimized for RNA stability. Based on the NA protein sequences provided, using routine skill nucleic acid molecules can be designed. Furthermore, exemplary NA coding sequences are provided herein. In one example, an NA coding sequence used to generate a VLP provided herein can be a nucleic acid sequence having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 15, SEQ ID NO: 17, SEQ ID NO: 28, SEQ ID NO: 30, SEQ ID NO: 32, or to any of the nucleic acid sequences provided in Table 3 by its GenBank® Accession No. In some examples, the NA coding sequence used to generate a VLP provided herein can be a nucleic acid encoding an NA protein with no more than 2, no more than 3, no more than 4, no more than 5, no more than 6, no more than 7, no more than 8, no more than 9, no more than 10, no more than 15, no more than 20, no more than 40, or no more than 50 amino acid substitutions (such as conservative amino acid substitutions) relative to SEQ ID NO: 16, SEQ ID NO: 18, SEQ ID NO: 29, SEQ ID NO: 31, SEQ ID NO: 33, or to any of the amino acid sequences provided in Table 3 by its GenBank® Accession No. For example, the NA coding sequence used to generate a VLP provided herein can be a nucleic acid encoding an NA protein having 2 to 20, 2 to 15, 1 to 10, 2 to 20, 5 to 40, 5 to 50, 5 to 15, or 5 to 10 amino acid substitutions (such as conservative amino acid substitutions) relative to SEQ ID NO: 16, SEQ ID NO: 18, SEQ ID NO: 29, SEQ ID NO: 31, SEQ ID NO: 33, or to any of the amino acid sequences provided in Table 3 by its GenBank® Accession No.

Vectors that include these nucleic acid molecules encoding recombinant NA polypeptides are also provided by the present disclosure. The vector can be any suitable vector for expression of the NA polypeptide, such as a mammalian expression vector. In particular examples, the vector is the pCAGGS expression vector or the pFastBacI baculovirus transfer vector plasmid. One skilled in the art will appreciate that any expression vector used for transfection or baculovirus expression can be used.

In some examples, the vector includes a promoter operably linked to the nucleic acid sequence encoding the NA polypeptide. In particular examples, the promoter is a CMV or SV40 promoter.

Also provided are isolated cells that include the disclosed NA-expressing vectors. In some cases, the cell is any suitable cell type for production and expression of VLPs, such as a mammalian cell or insect cell.

3. Matrix Proteins

The VLPs disclosed herein, in addition to having or expressing an HA subtype or an NA subtype, can also include an influenza matrix protein, such as M1, M2, or both (e.g., FIG. 1B). The influenza matrix protein is from the same influenza type as the HA or HA (e.g., if the HA or NA in the VLP is from influenza A, then the matrix protein is from influenza A, but if the HA or NA in the VLP is from influenza B, then the matrix protein is from influenza B). The matrix peptide sequence present in a VLP provided herein can be an influenza A M1, M2, or M1 and M2 sequence, such as an avian M1, M2, or M1 and M2 sequence, or an influenza B matrix peptide (such as M1, BM2, or both M1 and BM2). In one example, the VLP includes an influenza A M1 protein (e.g., see FIG. 1B) (for example if the VLP includes an influenza A NA or HA protein). In another example, the VLP includes both an influenza A M1 and an influenza A M2 protein (for example if the VLP includes an influenza A NA or HA protein). In another example, the VLP includes an influenza B matrix peptide (for example if the VLP includes an influenza B NA or HA protein). In another example, the VLP includes both an influenza B M1 and an influenza B BM2 protein (for example if the VLP includes an influenza B NA or HA protein).

In specific examples, a VLP provided herein includes an M1 protein, such as one having at least 80%, at least 85%, at least 90%, at least 92%, at least 95%, at least 96%, 96.5%, at least 97%, at least 97.5%, at least 98%, at least 98.5%, at least 99% or at least 99.5% sequence identity to SEQ ID NO: 20 or to any of the M1 amino acid sequences provided in Table 2 by its GenBank® Accession No. In some examples M1 present in a VLP has an amino acid sequence that includes SEQ ID NO: 20 or consists of SEQ ID NO: 20. In other examples, the M1 polypeptide in the VLP comprises or consists of the amino acid sequence of any M1 amino acid sequence provided in Table 2 by its GenBank® Accession No.

In one example, a VLP provided herein includes an M2 protein, such as one having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 21 or to any of the M2 amino acid sequences provided in Table 2 by its GenBank® Accession No. In some examples M2 present in a VLP has an amino acid sequence that includes SEQ ID NO: 21 or consists of SEQ ID NO: 21. In other examples, the M2 polypeptide in the VLP comprises or consists of the amino acid sequence of any M2 amino acid sequence provided in Table 2 by its GenBank® Accession No.

In specific examples, a VLP provided herein includes an influenza B matrix protein, such as one having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 35, SEQ ID NO: 37 or SEQ ID NO: 39 or to any of the influenza B matrix protein amino acid sequences provided in Table 2 by its GenBank® Accession No. In some examples the influenza B matrix protein present in a VLP has an amino acid sequence that includes SEQ ID NO: 35, consists of SEQ ID NO: 35, includes SEQ ID NO: 37, consists of SEQ ID NO: 37, includes SEQ ID NO: 39, or consists of SEQ ID NO: 39. In other examples, the influenza B matrix protein in the VLP comprises or consists of the amino acid sequence of any influenza B matrix protein sequence provided in Table 2 by its GenBank® Accession No.

In other embodiments, a matrix protein amino acid sequence in the VLP has no more than 2, no more than 3, no more than 4, no more than 5, no more than 6, no more than 7, no more than 8, no more than 9, no more than 10, no more than 15, no more than 20, no more than 40, or no more than 50 amino acid substitutions (such as conservative amino acid substitutions) relative to SEQ ID NO: 20, SEQ ID NO: 21, SEQ ID NO: 35, SEQ ID NO: 37, SEQ ID NO: 39, or to any of the amino acid sequences provided in Table 2 by its GenBank® Accession No. For example, the amino acid sequence of the matrix polypeptide present in a VLP can in some examples have 2 to 20, 2 to 15, 1 to 10, 2 to 20, 5 to 40, 5 to 50, 5 to 15, or 5 to 10 amino acid substitutions (such as conservative amino acid substitutions) relative to SEQ ID NO: 20, SEQ ID NO: 21, SEQ ID NO: 35, SEQ ID NO: 37, SEQ ID NO: 39, or to any of the amino acid sequences provided in Table 2 by its GenBank® Accession No. In other embodiments, the amino acid sequence of the M1 polypeptide includes no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 20. In other embodiments, the amino acid sequence of the M2 polypeptide includes no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 21. In some examples, the amino acid sequence of the M1 and/or the M2 polypeptide includes no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to any of the amino acid sequences provided in Table 2 by its GenBank® Accession No. In other embodiments, the amino acid sequence of the influenza B matrix protein includes no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to SEQ ID NO: 35, SEQ ID NO: 37, SEQ ID NO: 39. In some examples, the amino acid sequence of the influenza B matrix protein includes no more than 50, no more than 40, no more than 20, no more than 10, no more than 9, no more than 8, no more than 7, no more than 6, no more than 5, no more than 4, no more than 3, no more than 2 or no more than 1 amino acid substitution(s) (such as conservative amino acid substitutions) relative to any of the amino acid sequences provided in Table 2 by its GenBank® Accession No.

Further provided are isolated nucleic acid molecules encoding the matrix polypeptides disclosed herein. In some embodiments, the nucleic acid molecule is codon-optimized for expression in mammalian or insect cells. The nucleic acid molecule can be further optimized for RNA stability. Based on the matrix protein sequences provided, using routine skill nucleic acid molecules can be designed. Furthermore, exemplary matrix protein coding sequences are provided herein. In one example, an M1 coding sequence used to generate a VLP provided herein can be a nucleic acid sequence having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 20 or to any of the nucleic acid sequences provided in Table 2 by its GenBank® Accession No. In one example, an M2 coding sequence used to generate a VLP provided herein can be a nucleic acid sequence having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 21 or to any of the nucleic acid sequences provided in Table 2 by its GenBank® Accession No. In one example, an influenza B matrix protein coding sequence used to generate a VLP provided herein can be a nucleic acid sequence having at least 80%, at least 85%, at least 90%, at least 92%, at least 95%, at least 96%, at least 96.5%, at least 97%, at least 97.5%, at least 98%, at least 98.5%, at least 99% or at least 99.5% sequence identity to SEQ ID NO: 34, SEQ ID NO: 36, SEQ ID NO: 38, or to any of the nucleic acid sequences provided in Table 2 by its GenBank® Accession No.

In some examples, the matrix protein coding sequence used to generate a VLP provided herein can be a nucleic acid encoding a matrix protein with no more than 2, no more than 3, no more than 4, no more than 5, no more than 6, no more than 7, no more than 8, no more than 9, no more than 10, no more than 15, no more than 20, no more than 40, or no more than 50 amino acid substitutions (such as conservative amino acid substitutions) relative to SEQ ID NO: 20, SEQ ID NO: 21, SEQ ID NO: 34, SEQ ID NO: 36, SEQ ID NO:

38, or to any of the amino acid sequences provided in Table 2 by its GenBank® Accession No. For example, the matrix protein coding sequence used to generate a VLP provided herein can be a nucleic acid encoding a matrix protein having 2 to 20, 2 to 15, 1 to 10, 2 to 20, 5 to 40, 5 to 50, 5 to 15, or 5 to 10 amino acid substitutions (such as conservative amino acid substitutions) relative to SEQ ID NO: 20, SEQ ID NO: 21, SEQ ID NO: 34, SEQ ID NO: 36, SEQ ID NO: 38, or to any of the amino acid sequences provided in Table 2 by its GenBank® Accession No.

Vectors that include these nucleic acid molecules encoding matrix proteins are also provided by the present disclosure. The vector can be any suitable vector for expression of the matrix polypeptide, such as a mammalian expression vector. In particular examples, the vector is the pCAGGS expression vector or the pFastBacl baculovirus transfer vector plasmid. One skilled in the art will appreciate that any expression vector used for transfection or baculovirus expression can be used.

In some examples, the vector includes a promoter operably linked to the nucleic acid sequence encoding the matrix polypeptide. In particular examples, the promoter is a CMV or SV40 promoter.

Also provided are isolated cells that include the disclosed matrix protein-expressing. In some cases, the cell is any suitable cell type for production and expression of VLPs, such as a mammalian cell or insect cell.

4. Other Exemplary Components of the Composition

The influenza polyvalent VLP-containing compositions provided herein can include other agents. In some examples, the VLPs are present in a pharmaceutically acceptable carrier such as saline, buffered saline, dextrose, water, glycerol, sesame oil, ethanol, and combinations thereof. The carrier and composition can be sterile. The composition can also contain minor amounts of wetting or emulsifying agents, or pH buffering agents. The composition can also contain conventional pharmaceutical adjunct materials such as, for example, pharmaceutically acceptable salts to adjust the osmotic pressure, buffers, preservatives and the like. The composition can be a liquid solution, suspension, emulsion, tablet, pill, capsule, sustained release formulation, or powder. In one example, the composition is a liquid, or a lyophilized or freeze-dried powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate.

In some examples, the polyvalent VLP-containing compositions include a pharmaceutically acceptable carrier and an adjuvant, such as a mucosal adjuvant, for example as one or more of CpG oligodeoxynucleotides, Flt3 ligand, and monophosphoryl lipid A (MLA). In one example, the adjuvant includes MLA, such as a clinical grade formulation, for example MPL® (3-O-desacyl-4'-monophosphoryl lipid A) adjuvant.

5. Formulations for Mucosal Administration

The influenza polyvalent VLP-containing compositions provided herein can be formulated for mucosal vaccination, such as intranasal administration. Mucosal vaccination can be achieved by a number of routes including oral, intranasal, pulmonary, rectal and vaginal. In a specific example, this is achieved by intranasal administration. Thus, in some examples the disclosed compositions are formulated for intranasal administration.

For example, the disclosed compositions can include one or more biodegradable, mucoadhesive polymeric carriers. Polymers such as polylactide-co-glycolide (PLGA), chitosan, alginate and carbopol can be included. Hydrophilic polymers, like sodium alginate and carbopol, absorb to the mucus by forming hydrogen bonds, consequently enhancing nasal residence time, and thus can be included in the disclosed compositions.

In one example, the composition includes sodium alginate, which is a linear copolymer and consists of 1-4-linked β-d-mannuronic acid and 1-4-linked α-1-guluronic acid residues. In some examples, the composition includes alginate microspheres. In one example, the composition includes carbopol (a cross-linked polyacrylic acid polymer), for example in combination with starch. In some examples, the composition includes chitosan, a non-toxic linear polysaccharide that can be produced by chitin deacetylation. In one example the chitosan is in the form of chitosan nanoparticles, such as N-trimethyl chitosan (TMC)-based nanoparticles.

In one example, the composition is formulated as a particulate delivery system used for nasal administration. In one example the VLP-containing composition can include liposomes, immune-stimulating complexes (ISCOMs) and/or polymeric particles, such as virosomes. In one example, the liposome is surface-modified (e.g., glycol chitosan or oligomannose coated). In one example, the liposome is fusogenic or cationic-fusogenic.

The VLP-containing compositions can also include one or more lipopeptides of bacterial origin, or their synthetic derivatives. Examples of lipid moieties include tri-palmitoyl-S-glyceryl cysteine (Pam3Cys), di-palmitoyl-S-glyceryl cysteine (Pam2Cys), single/multiple-chain palmitic acids and lipoamino acids (LAAs).

The VLP-containing compositions can also include one or more adjuvants, for example a mucosal adjuvant, such as one or more of CpG oligodeoxynucleotides (CpG ODN), Flt3 ligand, and monophosphoryl lipid A (MLA). In one example, the adjuvant includes a clinical grade MLA formulation, such as MPL® (3-O-desacyl-4'-monophosphoryl lipid A) adjuvant.

Methods of Making VLPs

The VLPs present in the disclosed compositions can be made by expressing the desired influenza HA or NA protein, and in some examples also a desired influenza matrix protein (such as influenza M1, M2, or both), in a host cell. The host cell, such as a mammalian or insect cell, is transfected or infected with (1) a vector or virus encoding an influenza HA polypeptide or a vector or a virus encoding an influenza NA polypeptide, and in some examples also with (2) a vector or virus encoding an influenza matrix protein (such as influenza M1, M2, or both), under conditions sufficient to allow for expression of the HA polypeptide or NA polypeptide, and in some examples also the matrix protein (such as influenza M1, M2, or both) in the cell. In some examples, instead of being expressed by separate vectors, the NA or HA is expressed from the same vector as the matrix protein(s). VLPs in the supernatant are harvested or collected (for example by centrifugation of the supernatant), and can be further purified and/or concentrated (for example using a discontinuous sucrose gradient or other method known in the art).

In one example, VLPs are produced in a recombinant cell by expressing an HA or NA polypeptide. In some examples, VLPs are produced in a recombinant cell by expressing an HA or NA polypeptide in combination with an influenza matrix protein (such as influenza M1, M2, or both). The HA or NA polypeptide, as well as the matrix protein(s), can be expressed by a vector or virus that has been transfected or infected into a cell, such as a mammalian (e.g., 293 cell) or insect cell (e.g., Sf9 cell). In some examples, the method includes cloning the HA or NA sequence into a vector or virus. Similarly, the matrix protein sequence(s) is expressed from a vector or virus (which can be the same or a different vector/virus as the HA or NA containing vector/virus). In some examples, the method includes cloning the matrix protein sequence into a vector or virus. Other methods of producing influenza VLPs are known (see, for example, U.S. Patent Application Publication Nos. 2006/0263804; 2008/0031895; 2010/0166769; and 2010/0239610).

1. VLP Generation in Mammalian Cells

Methods of generating VLPs in mammalian cells are known (e.g., see Easterbrook et al., *Virology* 432:39-44, 2012, herein incorporated by reference). Briefly, a nucleic acid molecule encoding a desired HA protein or a desired NA protein, in some examples along with a nucleic acid molecule encoding an influenza matrix protein(s), are each cloned into an expression plasmid (e.g., pCAGGS). Exemplary HA, NA, M1, and M2 sequences are provided herein (e.g., see Tables 1-3), and the disclosure is not limited to the use of specific HA, NA, M1 or M2 sequences. In some examples, the M1, M2, NA and/or HA coding sequences can be codon-optimized for expression in mammalian cells. The resulting HA- or NA-containing vector is transfected into cells, in some examples along with the matrix protein(s) containing vector. In some examples, the matrix protein(s) are expressed from the same vector as HA or NA. In one example, the transfection is a transient transfection. Examples of cells that can be used include 293 cells, Vero cells, A549 cells, and the like.

The cells are incubated under conditions that allow the HA or NA (and in some examples also M1, M2, or both) to be expressed by the cell. For example, the mammalian cells can be incubated for about 72 hours at 37° C. Supernatant from the recombinant cells is harvested, for example after about 72 hours of culture, and debris can be removed by low speed centrifugation (e.g., at 2000 g for 10 minutes), filtration (e.g., using a 0.2 μm sterile filter), or both.

VLPs are concentrated using ultracentrifugation (e.g., at 100,000 g for 2 to 4 hours). The VLPs can be further purified using a 20-60% discontinuous sucrose gradient at 130,000 g for 16 hours. In some examples, the method includes determining which fractions are positive for HA or NA activity, wherein the positive fractions are collected and concentrated by ultracentrifugation at 100,000 g for 2 h. The resulting VLP-containing pellets can be resuspended in PBS pH 7.2 and stored (e.g., refrigerated at 2 to 8° C. or frozen at −20 to −80° C.). Total protein can be quantified using the Bradford BCA assay (Pierce, Rockford, Ill.) and the proportion of HA or NA of the total protein measured by Coomassie blue staining and semiquantitative densitometry analysis. The amounts of proteins incorporated into the VLP can be determined by western blot or other immunoassay.

2. VLP Generation in Insect Cells

Methods of generating VLPs in insect cells are known (e.g., see Smith et al., *Vaccine* 31:4305-13, 2013, herein incorporated by reference).

Briefly, a nucleic acid molecule encoding an HA protein or a NA protein, in some examples along with a nucleic acid molecule encoding an influenza matrix protein(s), are each cloned into a baculovirus transfer vector plasmid (e.g., pFastBacl, Invitrogen, Carlsbad, Calif.). In some examples, the matrix protein(s) are expressed from the same baculovirus transfer vector as HA or NA. In some examples, expression of HA, NA, M1 and/or M2 is under the transcriptional control of the *Autographa californica* multiple nuclear polyhedrosis virus (AcMNPV) polyhedrin promoter. Exemplary influenza HA, NA, M1 and M2 sequences are provided herein (e.g., see Tables 1-3), and the disclosure is not limited to the use of specific sequences. In some examples, the M1, M2, NA and/or HA coding sequences can be codon-optimized for expression in insect cells. Each recombinant baculovirus construct can be plaque purified and master seed stocks prepared, characterized for identity, and used to prepare working virus stocks. The titers of baculovirus master and working stocks can be determined by using a rapid titration kit (e.g., BacPak Baculovirus Rapid Titer Kit; Clontech, Mountain View, Calif.).

Insect cells, such as *S. frugiperda* Sf9 insect cells (ATCC CRL-1711), are maintained as suspension cultures in insect serum free medium (e.g., HyQ-SFX HyClone, Logan, Utah) at 27±2° C. Recombinant baculovirus stocks can be prepared by infecting cells at a low multiplicity of infection (MOI) of <0.01 plaque forming units (pfu) per cell and harvested at 68-72 h post infection (hpi).

The resulting HA- or NA-containing baculovirus vector (which may also include matrix protein(s) coding sequences) is used to infect cells, in some examples along with the matrix protein(s) containing baculovirus vector. In one example, about $2-3\times10^6$ cells/ml are infected with the HA- or NA-containing baculovirus vector (in some examples along with the matrix protein(s)-containing baculovirus vector). The resulting infected cells are incubated with continuous agitation at 27±2° C. and harvested about 68-72 hpi, for example by centrifugation (e.g., 4000×g for 15 minutes). VLPs can be purified from the infected cell media. For example, the media can be concentration and dialyzed against buffer using hollow fiber tangential flow filtration. Separation of VLP from baculovirus and other contaminants can be performed using anion exchange followed by gel filtration chromatography. Purified VLP in PBS can be filtered (e.g., 0.2 μm sterile filter) and stored (e.g., refrigerated at 2 to 8° C. or frozen at −20 to −80° C.).

Methods of Stimulating an Immune Response

Methods of using the disclosed polyvalent VLPs and VLP-containing compositions are provided herein. In one example, the methods include eliciting a broadly reactive immune response to influenza virus (such as influenza A, influenza B, or both) in a subject. In another example, the methods include immunizing or vaccinating a subject against influenza virus (such as influenza A, influenza B, or both) in a subject.

For example, the disclosed polyvalent influenza VLPs can stimulate a broadly-reactive immune response such that the subject administered the polyvalent VLPs animal is protected from serious illness or death from a wide variety of influenza A viruses without the need for a match between the challenge strain and the composition of the vaccine. It is shown herein that broad cross protection was achieved where the polyvalent VLPs did not contain the same HA subtype as the challenge strain (e.g., challenge strain as H1N1, but the VLPs did not express H1 or N1). Thus, the disclosed polyvalent influenza VLPs can be used as a pre-pandemic vaccine (e.g., when the VLPs include a mixture of VLPs containing influenza HA or NA).

Thus, in some examples, the immune response is to one or more of (such as at least 2, at least 3, at least 4, or at least 5 of) H1N1, H1N2, H1N7, H2N1, H2N2, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6, and H14N5. In some examples, the immune response is to one or more of H1N1, H1N2, H3N2, H7N9, and H5N1. In some examples, such immunization provides protection (e.g., prevents infection or prevents the development of disease associated with infection) against challenge by to one or more of (such as at least 2, at least 3, at least 4, or at least 5 of) H1N1, H1N2, H1N7, H2N1, H2N2, H3N1, H3N2, H3N8, H4N8, H5N1, H5N2, H5N8, H5N9, H6N1, H6N2, H6N5, H7N1, H7N2, H7N3, H7N4, H7N7, H7N9, H8N4, H9N2, H10N1, H10N7, H10N8, H11N1, H11N6, H12N5, H13N6, and H14N5. In some examples, such immunization provides protection (e.g., prevents infection or prevents the development of disease associated with infection) against challenge by one or more of H1N1, H1N2, H3N2, H7N9, and H5N1. In one example, the influenza VLPs disclosed herein can be used as influenza vaccines to elicit a protective immune response against H1N1 and/or H6N1 influenza viruses.

In some examples, the immune response or immunization is with a population of VLPs expressing different HA or NA subtypes than for which at least one immune response or protection is achieved. For example, if the subject is administered with a mixture of VLPs expressing H2, H3, H5 and H7, at least one of the immune responses or immunization is achieved with an H1 influenza virus, such as H1N1.

In one example, the disclosed polyvalent influenza VLPs (which include at least one population of VLPs expressing influenza A HA, and at least one population of VLPs having influenza B HA) can stimulate a broadly-reactive immune response such that the subject administered the polyvalent VLPs animal is protected from serious illness or death from a wide variety of pre-pandemic, pandemicinfluenza A viruses or seasonal influenza A and B viruses without the need for a match between the challenge strain and the composition of the vaccine. Thus, the disclosed polyvalent influenza VLPs can be used as a seasonal vaccine (e.g., when the composition includes a mixture of VLPs with influenza A and influenza B HA or NA proteins (such as influenza A H1, H3, H7, H7, N1 and N2, and influenza B Yamagata-like and/or Victoria-like).

In some embodiments, the disclosed polyvalent VLPs or VLP-containing composition is administered using any suitable route of administration, such as, intranasal. In some embodiments, the VLP-containing composition includes a pharmaceutically acceptable carrier and/or an adjuvant. For example, the pharmaceutically acceptable carrier can be saline, such as sterile PBS pH 7.2-pH 7.4. For example, the adjuvant can be one or more of immunostimulatory oligonucleotides (such as CpG oligonucleotides), Flt3 ligand, and monophosphoryl lipid A (MLA).

The disclosed compositions containing VLPs can be used to stimulate or elicit an immune response to influenza virus (such as influenza A, B or both) in a subject. In some examples the method includes administering a therapeutically effective amount of a composition containing the polyvalent VLPs provided herein to a subject, thereby eliciting an immune response to influenza virus in a subject. Methods of determining whether an immune response has been stimulated or elicited are known, and some examples are provided herein. In some examples, a positive immune response or immunization is achieved if there is an observed reduction in illness (e.g., less weight loss, reduction in symptoms, reduction in lung pathology), reduction in viral titers, and/or protection from death. Thus, in some examples, the disclosed methods and/or compositions reduce weight loss by at least 10%, at least 20%, at least 30%, at least 40%, or at least 50% (for example within 6 to 15 days post challenge), for example as compared to an equivalent subject not receiving the VLPs. In some examples, the disclosed methods and/or compositions reduce symptoms of influenza infection by at least 10%, at least 20%, at least 30%, at least 40%, or at least 50%, for example as compared to an equivalent subject not receiving the VLPs. In some examples, the disclosed methods and/or compositions reduce lung pathology due to influenza infection by at least 10%, at least 20%, at least 30%, at least 40%, or at least 50%, for example as compared to an equivalent subject not receiving the VLPs. In some examples, the disclosed methods and/or compositions reduce lung viral titer by at least 50%, at least 100%, at least 2-fold, at least 3-fold, at least 4-fold, or at least 5-fold, for example as compared to an equivalent subject not receiving the VLPs. In some examples, the disclosed methods and/or compositions increase survival following subsequent viral challenge by at least 10%, at least 20%, at least 30%, at least 40%, at least 50%, at least 75%, at least 80%, at least 90%, or at least 94%, for example as compared to an equivalent subject not receiving the VLPs.

The disclosed compositions containing VLPs can be used to immunize or vaccinate a subject against influenza virus, such as a mammalian subject or an avian subject. In some examples the method includes administering a therapeutically effective amount of a composition containing the polyvalent VLPs provided herein to a subject, thereby immunizing the subject against influenza virus. In some examples, a positive immune response or immunization is achieved if there is an observed reduction in illness (e.g., less weight loss, reduction in symptoms, reduction in lung pathology), reduction in viral titers, and/or protection from death.

Examples of subjects that can be administered the disclosed polymeric influenza VLP compositions include subjects that can be (or are) infected with influenza. Examples of such subjects include but are not limited to, mammalian and avian subjects, such as humans, pigs, chickens, turkeys, horses, dogs and cats.

In some embodiments of the methods of eliciting an immune response or immunizing a subject, the subject is administered (e.g., intransaly) about 1 to about 25 μg of each of the at least two different VLPs in the composition. In particular examples, the subject is administered (e.g., intransaly) about 1 to about 5 μg of each of the at least two different VLPs in the composition, about 5 to about 20 μg of each of the at least two different VLPs in the composition, or about 10 to about 15 μg of each of the at least two different VLPs in the composition. In one specific non-limiting example, the subject is administered (e.g., intransaly) about 1.5 μg or 15 μg of each of the at least two different VLPs in the composition. However, one of skill in the art is capable of determining a therapeutically effective amount (for example an amount that provides protection against H1N1 influenza virus infection) of VLPs to administer to a subject.

1. Methods of Administration

The disclosed polyvalent VLPs and VLP-containing compositions can be administered to a subject by any of the routes normally used for introducing VLPs into a subject. Methods of administration include, but are not limited to, intradermal, intramuscular, intraperitoneal, parenteral, intravenous, subcutaneous, mucosal, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, tablets, and the like. Administration can be systemic or local.

The polyvalent influenza VLP-containing compositions administered to a subject are administered with at least one pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present disclosure. Pharmaceutically acceptable carriers include, but are not limited to, saline, buffered saline, dextrose, water, glycerol, sesame oil, ethanol, and combinations thereof. The composition can also contain conventional pharmaceutical adjunct materials such as, pharmaceutically acceptable salts to adjust the osmotic pressure, buffers, preservatives and the like. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In particular examples, the compositions provided herein are formulated for mucosal vaccination, such as oral, intranasal, pulmonary, rectal and vaginal. In a specific example, this is achieved by intranasal administration. For example, the disclosed compositions can include one or more biodegradable, mucoadhesive polymeric carriers. Polymers such as polylactide-co-glycolide (PLGA), chitosan (for example in the form of chitosan nanoparticles, such as N-trimethyl chitosan (TMC)-based nanoparticles), alginate (such as sodium alginate) and carbopol can be included. In one example the composition includes one or more hydrophilic polymers, such as sodium alginate or carbopol. In one example, the composition includes carbopol, for example in combination with starch. In one example, the composition is formulated as a particulate delivery system used for nasal administration. Thus, the VLP-containing composition can include liposomes, immune-stimulating complexes (ISCOMs) and/or polymeric particles, such as virosomes. The VLP-containing compositions can also include one or more lipopeptides of bacterial origin, or their synthetic derivatives, such as Pam3Cys, (Pam2Cys, single/multiple-chain palmitic acids and lipoamino acids (LAAs). The VLP-containing compositions can also include one or more adjuvants, such as one or more of CpG oligodeoxynucleotides (CpG ODN), Flt3 ligand, and monophosphoryl lipid A (MLA). In one example, the adjuvant includes a clinical grade MLA formulation, such as MPL® (3-O-desacyl-4'-monophosphoryl lipid A) adjuvant.

2. Timing of Administration

The disclosed compositions containing two or more VLPs are administered as a single or as multiple doses (e.g., boosters). In some examples, the first administration is followed by a second administration. For example, the second administration can be with the same, or with a different VLP-containing composition than the first VLP-containing composition administered. In a specific example, the second administration is with the same VLP-containing composition as the first VLP-containing composition administered. In another specific example, the second administration is with a different VLP-containing composition than the first VLP-containing composition administered. For example, if the first VLP-containing composition included a first HA subtype and a second HA subtype, the second VLP-containing composition can include a third HA subtype and a fourth HA subtype, wherein all four subtypes are different (such as four of H1, H2, H3, H5, H7, and H9).

In some examples, the compositions containing two or more VLPs are administered as multiple doses, such as 2, 3, 4, 5, 6, 7, 8, 9, or 10 doses (such as 2-3 doses). In such examples, the timing between the doses can be at least 1 week, at least 2 weeks, at least 3 weeks, at least 4 weeks, at least 6 weeks, at least 8 weeks, at least 12 weeks, at least 2 months, at least 3 months, at least 4 months, at least 5 months, at least 6 months, at least 1 year, at least 2 years, or at least 5 years, such as 1-4 weeks, 2-3 weeks, 1-6 months, 2-4 months, 1 week, 2 weeks, 3 weeks, 4 weeks, 5 weeks, 6 weeks, 7 weeks, 8 weeks, 9 weeks, 10 weeks, 12 weeks, 1 month, 2 months, 3, months, 4, months, 5 months, 6 months, 1 year, 2 years, 5 years, or 10 years, or combinations thereof (such as where there are at least three administrations, wherein the timing between the first and second, and second and third doses, can be the same or different).

3. Dosages

The dose administered to a subject in the context of the present disclosure should be sufficient to induce a beneficial therapeutic response in a subject over time, or to inhibit or prevent influenza virus infection. The dose required can vary from subject to subject depending on the species, age, weight and general condition of the subject, the severity of the infection being treated, the particular composition being used and its mode of administration. An appropriate dose can be determined by one of ordinary skill in the art using only routine experimentation.

In some embodiments, the subject is administered (e.g., intranasally) about 1 to about 100 μg of each of the at least two different VLPs in the composition, such as about 1 μg to about 50 μs, 1 μs to about 25 μg, 1 μs to about 5 μs, about 5 μs to about 20 μs, or about 10 μs to about 15 μg of each of the at least two different VLPs in the composition. In one specific non-limiting example, the subject is administered (e.g., intranasally) about 15 μs of each of the at least two different VLPs in the composition. In another specific non-limiting example, the subject is administered (e.g., intranasally) about 10 μs of each of the at least two different VLPs in the composition. In one specific non-limiting example, the subject is administered (e.g., intranasally) about 20 μs of each of the at least two different VLPs in the composition. In one specific non-limiting example, the subject is administered (e.g., intranasally) about 1 μg or 2 μg of each of the at least two different VLPs in the composition.

4. Methods for Measuring Immune Response

Methods for determining whether a VLP-containing composition disclosed herein can or did elicit or stimulate an immune response, such as achieve a successful immunization, are known in the art. For example, see Cottey et al., in *Current Contents in Immunology* 19.11.1-19.11.32, 2001 (herein incorporated by reference). Although exemplary assays are provided herein, the disclosure is not limited to the use of specific assays.

Following administration of a polyvalent influenza VLP composition provided herein, one or more assays can be performed to assess the resulting immune response. In some example, the assays are also performed prior to administration of the VLPs, to serve as a baseline or control. Samples are collected from the subject following administration of the VLP composition, such as a blood or serum sample. In some examples, the sample is collected at least 1 week, at least 2 weeks, at least 3 weeks, at least 4 weeks, at least 5 weeks, at least 6 weeks, or at least 8 weeks (such as 1, 2, 3, 4, 5, 6, 7, 8, 9, 10, 11, or 12 weeks) after the first VLP administration. Subsequent samples can be obtained as well, for example following subsequent VLP administrations.

a. Hemagglutination Titer Assay

In one example, following production and purification of a VLP-containing composition provided herein, a hemagglutination titer assay is performed. Such assays can be performed to measure or evaluate hemagglutinating units (HAU). This is used to evaluate that the VLP expresses functional HA trimers, and can be used to quantify HA protein in the VLP preparation. Hemagglutination titers are also used to quantify the amount of influenza virus used a challenge virus, or for example to quantify amount of virus (titering) present in the lungs or respiratory tract of challenged animals. Vaccinated subjects may show a reduction in viral titers as compared to mock-vaccinated subjects.

This assay can be used to quantify the amount of VLP or also to quantify virus in a sample, such as a lung sample from a virus challenged subject previously administered the VLP-containing compositions provided herein. VLP or virus stocks are serially diluted (e.g., 2-fold from 1:4 to 1:4096) and then added to wells containing red blood cells (RBCs). RBC solution (such as 0.75% to 1% RBC) is added to the wells. The mixture is then incubated for 30 min at room temperature, which allows the RBC to settle. The samples are then analyzed for their resulting agglutination pattern, for example by examining microtiter wells in which the sample was placed. For example, in a microtiter plate placed on its edge, the RBC in the RBC control wells will flow into a characteristic teardrop shape (no influenza virus is present so there is no agglutination). Wells that contain influenza virus will agglutinate the RBC to varying degrees. The wells with the greatest amount of virus will appear cloudy, because the virus has cross-linked all the red blood cells, preventing their pelleting. Lesser amounts of virus in succeeding wells may result in partial agglutination, but the pellet will not stream into a teardrop shape similar to the pellets in the RBC control wells. The endpoint is typically determined as the greatest dilution of the VLP or virus sample resulting in complete agglutination of the RBC.

The number of hemagglutinating units (HAU) in the sample being titered can be determined. The HA titer is the reciprocal of the dilution of the last well of a series showing complete agglutination of the RBC (e.g., if the last dilution was 1:640, the titer of the sample is 640 HA units/5 μl sample).

b. Hemagglutination Inhibition (HA1) Assay

In one example, following administration of a VLP-containing composition provided herein, a hemagglutination inhibition (HA1), assay is performed. Influenza viruses can agglutinate red blood cells, a process called hemagglutination, as described above. In the presence of specific antibody to the surface hemagglutinin, hemagglutination is blocked. This phenomenon provides the basis for the HA1 assay, which is used to detect and quantitate specific antiviral antibodies in serum. Thus, HA1 measures the presence of antibodies that block HA receptor binding (as assessed by hemagglutination of RBC).

In one example, sera to be evaluated for the presence of antibodies against the head of hemagglutinin is treated with receptor destroying enzyme (RDE) at 37° C. overnight. The following day, RDE is inactivated by incubation at 56° C. for 1 hour. Assay plates used are 96-well, nonsterile, nontissue culture-treated, round-bottom microtiter plates. Two-fold serial dilutions are carried out on each sample down the plate from row B through row G. 50 μl of working dilution of viral antigen (a set number of HAU) is added to all wells of the microtiter plates except for row H (the RBC control wells) and the antigen control wells. The plates are incubated for 30 min at room temperature. 50 μl 1% RBC suspension in PBS is added to all wells and the plates incubated for 30 to 45 min at room temperature. The microtiter plate is analyzed to read the agglutination patterns. The negative control wells (those containing normal serum without anti-influenza antibodies) will appear cloudy, because the influenza virus has completely agglutinated the RBC. The positive control wells (those containing known anti-influenza antiserum) will have RBC pellets similar in appearance to the row H control pellets as long as there is sufficient anti-influenza antibody to inhibit agglutination. With increasing serum dilution, the amount of antibody will decrease so that increasing amounts of RBC agglutination will become apparent. The hemagglutination inhibition (HA1) titer for each serum sample is the reciprocal of the greatest dilution which completely inhibits the agglutination of the RBC (i.e., the last well in a dilution series forming a RBC pellet). The HA1 titer for each sample is the mean of the endpoint titers of its duplicate dilution series. If the titer of the duplicates differs by more than one two-fold dilution, the HA1 titer can be repeated for that sample.

c. Influenza Virus Neutralization Assay

In one example, following administration of a VLP-containing composition provided herein, a neutralization assay is performed. In this assay, serum samples from subjects who received a VLP-containing composition provided herein are diluted, influenza virus is added, and the amount of serum necessary to prevent virus growth determined. Neutralization assesses the presence of antibodies that inhibit viral replication. Antibodies to the stalk of HA for example can neutralize viral replication but not affect hemagglutination because the epitope is not around the receptor binding domain. Antibodies that bind to the head and inhibit hemagglutination are usually neutralizing.

In some examples, the serum samples are incubated in tissue culture medium (such as DMEM/5% FBS containing antibiotics), for example in 96-well, round-bottom, tissue culture-treated microtiter plate. The serum samples are serially diluted, for example in duplicate adjacent wells of a microwell plate (for example initially diluted 1:10 to a dilution of the sample of 1:640). Previously titered influenza virus (of any subtype) can be diluted to contain 1 $TCID_{50}/50$ μl. Equal amounts of the working stock virus (such as about 50 $TCID_{50}$) are added to each serum sample (including the serial dilutions), and incubate at 37° C. for 1 hr. With this protocol, the same neutralization titer is obtained if the final amount of virus is between 10 to 100 $TCID_{50}$. Following the incubation, tissue culture medium (such as DMEM/5% FBS with antibiotics) containing $2.5 \times 10^5$ MDCK cells/ml (or other cells) are added to the serum samples (e.g., to all wells of the microtiter plate). This is incubated overnight in a humidified 37° C., 5% $CO_2$ incubator. Note that some influenza viruses will grow better at temperatures of 34° to 35° C., and thus in some examples those temperatures are used. The media is removed, and replaced with tissue culture medium (such as DMEM with antibiotics) containing trypsin (such as 0.0002%), and the mixture incubated in a humidified 37° C., 5% $CO_2$ incubator for 4 days. Subsequently, sterile 0.5% RBC/PBS solution is added, and the mixture incubated at 4° C. for 1 hr, and the wells checked for the presence of agglutination. The virus neutralization titer of a particular serum sample is defined as the reciprocal of the highest dilution of serum where both wells show no agglutination of the RBC.

Samples (e.g., in a microwell) containing influenza virus neutralizing antibodies at sufficient concentration will prevent the virus from infecting the cells so that viral multiplication will not take place. The addition of RBCs to these wells will result in the formation of a pellet of RBC. In contrast, samples (e.g., in a microwell) that had none or less than neutralizing concentrations of anti-influenza antibody will have influenza virus present at the end of the 4-day incubation. The RBC added to these samples will agglutinate. Influenza virus cross-links the red blood cells, inhibiting their settling in the microwell, and the wells therefore appear cloudy.

d. Neuraminidase Inhibiting (NI) Antibody Titer Assay

Neuraminidase inhibiting (NI) antibody titers can be determined if a VLP in the composition contains an NA protein. To measure NI antibody titers, reassortant viruses containing the appropriate NA can be generated, for example by using plasmid-based reverse genetics (e.g., see Sandbulte et al., *Influenza Other Respir Viruses* 3:233-40, 2009). The appropriate NA will be the same one(s) present in the VLP administered to the subject. The NI assay can be performed using fetuin as a NA substrate (e.g., see Cate et al., *Vaccine* 28:2076-9, 2010, herein incorporated by reference). An exemplary method is provided below.

The NI titer is the inverse of the greatest dilution of sera that provides at least 50% inhibition of NA activity. It is expected that use of the VLPs disclosed herein will decrease or even eliminate challenge virus titers in subjects who received the polyvalent VLP compositions. For example, subjects who receive the polyvalent VLP compositions are expected to have at least 10-fold, at least 20-fold, at least 50-fold, or even 100-fold less virus in the lungs than subjects who did not receive the polyvalent VLP compositions (e.g., are mock vaccinated).

NI antibody titers can be determined in an enzyme-linked lectin assay using peroxidase-labeled peanut agglutinin (PNA-PO) to bind to desialylated fetuin. NA activity can be determined by incubating serial dilutions of purified, full length NA on fetuin coated microtiter plates. After 30 min incubation at RT, plates are washed and PNA-PO added. After 1 h incubation at RT, plates are again washed and the peroxidase substrate 3,3',5,5'-tetramethylbenzidine added and color development allowed to proceed for 10 min. Color development is stopped and the plates the OD450 measured. Dilution corresponding to 95% NA activity is determined.

NI titers against an NA subtype can be measured beginning at a 1:20 dilution of sera followed by 2-fold serial dilutions in 96-well U-bottomed tissue culture plates. NAs corresponding to 95% maximum activity are added to diluted sera and incubated for 30 min at RT after which sera/NA samples were transferred to fetuin coated microtiter plates. Plates are incubated for 2 h at 37° C., washed and PNA-PO added. The plates are incubated at RT an additional hour, washed and peroxidase substrate TMB added. Color development is stopped after 10 min and the OD450 of the plates measured. The NI titers are the reciprocal dilution at which 50% NA activity was inhibited. The lower limit of quantitation for the assay is 20; titers lower than 20 are considered to be negative and assigned a value of 10. In some examples a good or positive response produces a value of >30, while a poor or no response produces a value <20.

e. Viral Lung Titers and Pathology

Viral lung titers and pathology can be determined. Tissue samples, such as lung samples (e.g., inflated lung samples) are fixed (e.g., 24 h fixation in 10% formaldehyde), embedded (e.g., in paraffin), cut into sections (e.g., 1 to 10 μm, such as 5 μm), and mounted.

Influenza virus antigen distribution can be evaluated by immunohistochemistry using an appropriate antibody (e.g., a polyclonal or monoclonal antibody that is either specific for the virus used to challenge the subject or one that is cross-reactive to different influenza virus strains can be used). It is expected that use of the VLPs disclosed herein will decrease or even eliminate virus titers in subjects who received the polyvalent VLP compositions. For example, subjects who receive the polyvalent VLP compositions are expected to have at least 10-fold, at least 20-fold, at least 50-fold, or even 100-fold less virus in the lungs than subjects who did not receive the polyvalent VLP compositions (e.g., are mock vaccinated). In another example, it is expected that use of the VLPs disclosed herein will decrease or even eliminate symptoms of influenza infection, such as bronchitis, bronchiolitis, alveolitis, and/or pulmonary edema, in subjects who received the polyvalent VLP compositions. For example, subjects who receive the polyvalent VLP compositions are expected to have at least 20%, at least 50%, at least 75%, or at least 90% less bronchitis, bronchiolitis, alveolitis, and/or pulmonary edema (or such reductions in severity of these symptoms) as compared subjects who did not receive the polyvalent VLP compositions (e.g., are mock vaccinated).

f. Other Exemplary Assays

In some examples, subjects are assessed for respiratory IgA and systemic IgG, T-cell responses. Such methods are routine (e.g., see Gauger et al., *Methods Mol Biol.* 1161: 303-12, 2014; Larsen et al., *Vet Microbiol.* 74(1-2):117-31, 2000; Steitz et al., *PLoS One.* 5(5):e10492, 2010).

In some examples, immune responses are analyzed by transcriptomics and cytokine ELISAs or other cytokine immunoassays. Such methods are routine.

In some examples, immune responses are analyzed by microneutralization. Such methods are routine (e.g., see Gauger et al., *Methods Mol Biol.* 1161:313-24, 2014).

In some examples, immune responses are analyzed by anti-HA stalk assays. Such methods are routine (e.g., Wu et al., *PLoS One* 7(8):e42363, 2012).

Example 1

Generation of HA VLPs

This example describes methods used to generate VLPs containing different HA subtypes. However, one skilled in the art will appreciate that other HA sequences can be used (e.g., other H1 sequences can be used), and that NA sequences (such as those provided herein) can be used instead of HA sequences. In addition, one will appreciate that the VLPs could be generated using baculovirus/insect cell system, as an alternative to the vector/mammalian system described below.

The general method of Easterbrook et al. (Virology 423: 39-44, 2012, herein incorporated by reference) was used to make VLPs, except that HA was used instead of NA. The following VLPs were generated (1) H1+M1+M2 (2) H2+M1+M2, (3) H3+M1+M2, (4) H5+M1+M2, and (5) H7+M1+M2.

Briefly, the HA gene segments of (1) H1: A/mallard/Ohio/265/1987 (H1N9) Acc. No. CY017275.1 (SEQ ID NO: 1), or H1: A/South Carolina/1/1918 (H1N1) Acc. No. AF117241.1 (SEQ ID NO: 3); (2) H2: A/green-winged teal/Ohio/175/1986 (H2N1) Acc No. CY018877.1 (SEQ ID NO: 5), or H2: A/Japan/305/1957 (H2N2) Acc. No. J02127.1 (SEQ ID NO: 7); (3) H3 A/pintail/Ohio/339/1987 (H3N8) Acc. No. CY019197.1 (SEQ ID NO: 9); (4) H5 A/mallard/Maryland/802/2007 (H5N1) Acc. No. CY017781.1 (SEQ ID NO: 11); and (5) H7: A/Environment/Maryland/261/2006 (H7N3) CY022749.1 (SEQ ID NO: 13) were each separately cloned into a pCAGGS expression plasmid and transfected into 293T cells along with the A/New York/312/2001 (H1N1) M gene segment (GenBank Accession No. CY002697.1, SEQ ID NO: 19) in pCAGGS using Polyjet DNA transfection reagent (SignaGen, Rockville, Md., USA). In some examples, the segments of HA and M were cloned into the pFasBac expression vector immediately downstream of the polyhedron promoter and VLPs produced using standard Baculovirus expression systems (e.g., two separate bacmids containing HA and M1 genes were used to produce an H1 VLP or single bacmids containing flanking HA/M1 genes were used to produce the H3, H5 and H7 VLPs). Cell culture supernatant was harvested after 72 h and debris was removed by centrifugation at 2000 g for 10 min.

VLPs were concentrated by ultracentrifugation at 100,000 g for 2 h and purified using a 20-60% discontinuous sucrose gradient at 130,000 g for 16 h. The fractions that were positive for HA activity were collected and concentrated by ultracentrifugation at 100,000 g for 2 h. Total protein was quantified using the Bradford BCA assay (Pierce, Rockford, Ill.) and the proportion of NA of the total protein was measured by Coomassie blue staining and semiquantitative densitometry analysis. The amounts of M and other cellular proteins incorporated into the VLP were determined to be approximately <25%; by western blot, no M2 was detectable.

HA activity of the VLPs was measured using the hemagglutination assay.

The structure and shape of the HA and NA VLPs were confirmed by negative staining transmission electron microscopy (TEM) (FIGS. 2A-2C).

Example 2

Stimulation of Protective Immune Response in Mice Against H1N1 and H6N1

This example describes methods used to immunize mice using the VLPs described in Example 1. However, one skilled in the art will appreciate that other VLPs can be used (e.g., other HA-VLPs and/or NA-VLPs can be used), and that other animals can be similarly immunized (e.g., ferrets, humans, birds, etc.) as is described for mice.

In published experiments, NA-only VLP vaccinated mice, in the absence of HA antigen, were fully protected from a lethal H5N1 challenge (FIG. 3; Easterbrook et al. *Virology.* 432:39, 2012). This demonstrates the importance of NA immunity in mitigating viral infection and protecting animals from a lethal infection.

Groups of 7-8 week old female BALB/c mice (Jackson Laboratories, Bar Harbor, Me.; n=10 per treatment group) were lightly anesthetized with isofluorane supplemented with $O_2$ (1.5 L/min) before immunization or virus challenge. Mice (n=10 per group) were immunized intranasally (i.n.) with 1.5 μg of each HA subtype (H1, H2, H3, H5, and/or H7) in 50 μl, to elicit mucosal, as well as serum, antibody responses. "Mock" mice were treated with PBS.

Three weeks after the initial vaccination, mice were boosted with the same amount of VLP via the same route. Six weeks after the initial vaccination (3 weeks after boost) or infection, mice were anesthetized and challenged i.n. with 10×$MLD_{50}$ of 1918 H1N1 or avian H6N1 in 50 μl DMEM. Survival and body weight were monitored for 14 days and mice were euthanized if more than 25% of initial body weight was lost.

In one experiment, mice were vaccinated intranasally with a polyvalent mixture of HA-only VLPs expressing 4 different HA subtypes (H2, H3, H5, and H7). The mice were vaccinated such that one group received H2 and H5 VLPs initially and were boosted at 3 weeks with a mixture of H3 and H7 VLPs. The second group was initially vaccinated with H3 and H7 VLPs followed by a H2 and H5 VLP boost. A third group was mock vaccinated. At six weeks, all animals were challenged with a lethal dose (10×$MLD_{50}$) of the 1918 H1N1 influenza A virus. As shown in FIG. 4, 100% survival was achieved following 10×MLD50 lethal challenge with 1918 H1N1 virus in mice vaccinated with H2+H3+H5+H7, but no H1. The complete heterosubtypic protection observed from a lethal challenge with an H1 subtype virus with a polyvalent vaccine mixture that did not contain HA VLPs of H1 subtype.

In another experiment, mice were vaccinated intranasally with a polyvalent mixture of HA-only VLPs expressing 4 different HA subtypes in 2 groups (group 1: H1, H2, H3, and H7; group 2: H1, H3, H5, and H7). The mice were vaccinated such that group one received H1 and H3 VLPs initially and were boosted at 3 weeks with a mixture of H2 and H7 VLPs. The second group was initially vaccinated with H3 and H5 VLPs followed by a H1 and H7 VLP boost. A third group was mock vaccinated. At six weeks, all animals were challenged with a lethal dose (10×$MLD_{50}$) of an avian H6N1 influenza A virus. As shown in FIG. 5, 100% survival was achieved following 10×LD50 lethal challenge with avian H6N1 virus in mice vaccinated with H1+H2+H3+H5 or H7 but no H6. The complete heterosubtypic protection observed from a lethal challenge with an H6 subtype virus with a polyvalent vaccine mixture that did not contain HA VLPs of H6 subtype.

Thus, polyvalent mixtures of different HA VLPs can fully protect against heterologous lethal challenges with 1918 H1N1 (FIG. 4) or avian H6N1 (FIG. 5) influenza viruses. Cross-protective immunity is elicited by the VLPs since the polyvalent vaccines used did not contain the HA subtype of the subsequent lethal challenge viruses.

Example 3

Stimulation of Protective Immune Response in Mice Against H1N1 and H6N1

VLPs were generated as described in Example 1, and administered as described in Example 2.

Briefly, mice were vaccinated intranasally with a polyvalent mixture of HA-only VLPs (1.5 µg each HA) expressing 4 different HA subtypes (H1, H3, H5, H7). Mice were boosted at 3 weeks with the same mixture. A second group of mice were mock vaccinated. At six weeks, animals were challenged with a lethal dose ($10 \times MLD_{50}$) of 1918 H1N1 virus, high path H5N1, H7N9, 1957 pandemic H2N2, avian H6N1, or avian H10N1 virus. Survival of the mice will be monitored.

It is expected that this polyvalent mixture of VLPs will protect the mice from challenge with all of these viruses.

Example 4

Stimulation of Protective Immune Response with Addition of Adjuvant

Figure 6:
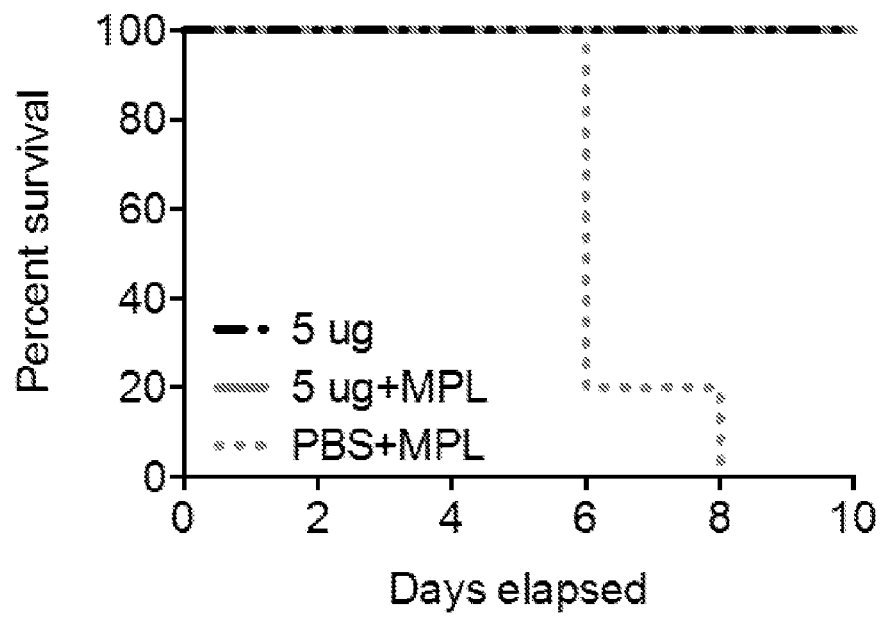
FIG. 6 is a survival curve showing 100% survival of monovalent H1 VLP vaccinated animals with or without addition of adjuvant.

Mice were vaccinated with 5 µg of a monovalent avian H1 expressing VLP (generated using the method of Example 1), or PBS, with and without 10 µg MPL adjuvant (a TLR agonist). The mice were subsequently boosted with the same VLPs or PBS. 3 weeks after boost, mice were challenged with a lethal dose of 1918 H1N1 virus. As shown in FIG. 6, all vaccinated mice survived.

Figure 7:
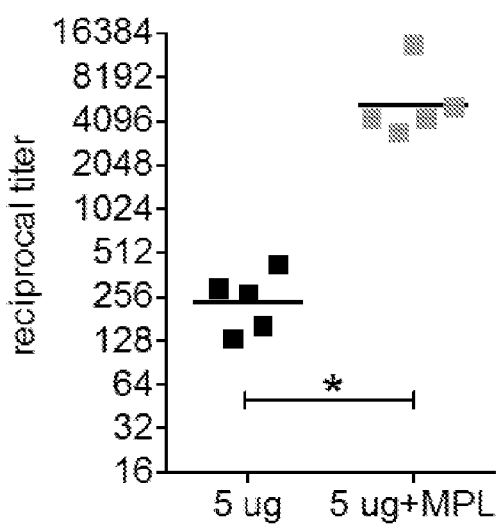
FIG. 7 is a graph showing higher neutralization titers in mice that received MPL-adjuvanted VLP vaccine (on the right) than those that did not received adjuvant (on the left).

Prior to 1918 virus challenge, serologic studies showed higher neutralization titers were observed in mice that received MPL-adjuvanted VLP vaccine (FIG. 7).

Example 5

Generation of VLP Vaccine and Testing in Mice

A polyvalent intranasal vaccine formulation that includes of mixture of HA VLPs separately expressing H1, H3, H5, and H7 will be generated as described in Example 1, and administered to mice as described in Example 2 (but both does of VLPs administered will be the same, as in Example 3). The VLPs will also contain M1 and M2. One skilled in the art will appreciate that other polyvalent influenza VLP compositions provided herein can be similarly tested.

Mice will be subsequently (4 to 6 weeks following the first VLP administration) challenged separately with a lethal dose ($10 \times MLD_{50}$) a variety of pathogenic influenza virus including the 1918 H1N1, 1957 H2N2, and 2009 H1N1 pandemic viruses, highly pathogenic H5N1, H7N9, H6N1, and H10N1 avian influenza viruses, and other relevant challenge viruses (such as H7N1, H7N9, and H11N1).

Mice will be evaluated for survival and vaccine-induced immunity, for example, by hemagglutination inhibition, microneutralization, and anti-HA stalk assays along with neuraminidase inhibition assays. Vaccinated animals will also be assessed for respiratory IgA and systemic IgG, T-cell responses, viral lung titers and pathology, and immune responses by transcriptomics and cytokine ELISAs.

In one example, eight-to-nine-week old female BALB/c mice were vaccinated with 1.5 each of H1, H3, H5 and H7 VLP (6 µg total) i.n. or with PBS for mock-vaccination. VLPs also contained M1. Mice were boosted at 21 days post-immunization. At 50 days post-initial immunization, mice were challenged with a lethal dose (see Table 4) of various challenge influenza A viruses and weighed daily. Challenge viruses were generated as follows. A standard reverse genetics-based system was utilized to produce influenza A viruses. Isogenic chimeric viruses were rescued using the PB1, $PB2^{E627K}$, PA, NP, NA, M, and NS gene segments from influenza A/Green Wing Teal/Ohio/175/1986 (H2N1), along with the H6, H7, or H10 HA segments as previously described (35). Chimeras were also produced using HA segments from A/South Carolina/1/1918 (H1N1), A/Japan/305/1957 (H2N2), as well as a lab variant of A/green-winged teal/Ohio/340/1987 (H11N9). Wild type (WT) influenza viruses A/Anhui/1/2013 (H7N9) and A/Vietnam/1203/04 (H5N1) were also used as challenge viruses. All WT and chimeric viruses were passaged 1-to-2 times in Madin-Darby canine kidney (MDCK) cells. Viruses were sequence verified and titered using plaque assay. Both viruses and samples were handled under biosafety level 3 enhanced laboratory (BSL3+) conditions. Influenza A/H5N1 virus and infectious samples were handled under BSL3+ conditions in accordance with the Select Agent guidelines of the National Institutes of Health (NIH), the Centers for Disease Control and Prevention (CDC), and the United States Department of Agriculture (USDA).

TABLE 4

Properties of challenge viruses used and survival post-challenge

| Challenge Virus* | MLD50 | VLP Vaccinated | | | Mock Vaccinated | | |
|---|---|---|---|---|---|---|---|
| | | Total number | Weight nadir | Percent Survival | Total number | Weight loss nadir | Percent Survival |
| 1918 H1N1 | $10^{3.25}$ | 5 | 99.4 | 100 | 5 | 74.0 | 0 |
| 1957 H2N1 | $10^{3.5}$ | 10 | 82.8 | 100 | 10 | 73.1 | 0 |
| H5N1 | $10^{0.7}$ | 10 | 89.6 | 90 | 10 | 74.4 | 10 |
| H6N1 | $10^{2.5}$ | 24 | 93.3 | 83.3 | 15 | 73 | 0 |
| H7N9 | $10^{1.7}$ | 15 | 96.3 | 100 | 15 | 73.2 | 0 |
| H7N1 | $10^{2.5}$ | 5 | 97.0 | 100 | 5 | 71.8 | 0 |
| H10N1 | $10^{1.6}$ | 10 | 88.3 | 100 | 10 | 73.6 | 20 |
| H11N1 | $10^{2.65}$ | 10 | 95.3 | 100 | 5 | 72.6 | 20 |
| Overall | | 89 | | 94.4 | 75 | | 5.3 |
| Duration of protection Study H7N9 | $10^{1.7}$ | 5 | 98.4 | 100 | 5 | 73.8 | 20 |
| Duration of protection Study H10N1 | $10^{1.6}$ | 5 | 79.2 | 80 | 5 | 74.0 | 20 |
| Aged mouse Study H10N1 | $10^{1.6}$ | 6 | 79.8 | 66.7 | 5 | 73.9 | 0 |

*Challenge viruses: Chimeric viruses were rescued using the PB1, $PB2^{E627K}$, PA, NP, NA, M, and NS gene segments from influenza A/Green Wing Teal/Ohio/175/1986 (H2N1), along with the H6, H7, or H10 HA segments. Chimeras were also produced using HA segments from A/South Carolina/1/1918 (H1N1), A/Japan/305/1957 (H2N2), as well as a lab variant of A/green-winged teal/Ohio/340/1987 (H11N9). Wild type (WT) influenza viruses A/Anhui/1/2013 (H7N9) and A/Vietnam/1203/04 (H5N1) were also used as challenge viruses.

Mouse vaccinations and infections were performed as follows. Mouse 50% lethal dose ($MLD_{50}$) determinations were performed on 8-9 week old female BALB/c mice (Jackson Laboratories, Bar Harbor, Me.) to assess murine pathogenicity of chimeric and WT viruses as previously described (Qi et al., mBio 5:e02116, 2014). For vaccination studies, 8-9 week old female BALB/c mice (Jackson Laboratories, Bar Harbor, Me.) (n=5-10 per treatment group)

were vaccinated intranasally (i.n.) with 1.5 µg each of H1, H3, H5, and H7 VLPs diluted in total in 50 µL of PBS at day 0. Mice were observed and boosted i.n. with an identical 6 µg dose at day 21. Cohorts of mock-vaccinated mice were vaccinated and boosted i.n. alongside vaccinated mice with 50 µl phosphate-buffered saline (PBS). For evaluation of vaccine efficacy in aged mice, 37-week-old Balb/C female mice were vaccinated and boosted i.n. at days 0 and 21. Mice were challenged on day 50 with 10×MLD$_{50}$ of virus diluted in 50 µL of Dulbecco's modified Eagle's medium (DMEM) i.n. To assess longevity of protection, mice were housed for an additional 6 months prior to challenge. Influenza A/H5N1 virus and infectious samples were handled under ABSL3+ conditions in accordance with the Select Agent guidelines of the NIH, CDC, and USDA. Survival and body weight were monitored for 14 days and mice were humanely euthanized if more than 25% of initial body weight was lost. Survival and mean time to death were analyzed by Kaplan-Meier survival analysis (Graph Pad Prism, La Jolla, Calif.). Differences in the percent weight loss nadirs, lung virus titers, and antibody responses were assessed using the Student's t-test. Mean differences were considered statistically significant if p<0.05. Mouse lungs were collected for viral titrations from H6N1-, H10N1-, and Anhui H7N9-infected animals on day 3 post-infection. Viral titers were determined for each lung sample as previously described (Id.).

Weight loss (i, iii, v, vii) of VLP-vaccinated (FIGS. 8A-C solid square) and mock-vaccinated (FIGS. 8A-C open circle) mice is expressed as mean percent of initial weight±SD. Survival (ii, iv, vi, viii) of VLP- (FIGS. 8A-C solid line) and mock-vaccinated (FIGS. 8A-C dotted line) mice were assessed for 14 days post-challenge. At 3 days post-infection, lungs were harvested and viral replication was measured in the lungs by plaque assay (FIGS. 9A-9D). Some mice were vaccinated but not challenged until 6 months after vaccination (FIG. 10A) or vaccinated at approximately 1 year of age (FIG. 10B).

This polyvalent mixture of VLPs was shown to afford significant protection in the mice from lethal challenge with all of these viruses (FIGS. 8A-8C). In aggregate, 94.4% of vaccinated mice survived challenge (84/89 animals) as compared to 5.3% of mock-vaccinated mice (4/75 animals; p<0.001). When challenged with viruses that expressed HAs identical to those contained in the vaccine (homologous challenge with 1918 H1N1 and avian H7N1; FIG. 8A), vaccinated mice showed 100% survival with only minimal weight loss nadirs (0.6% for 1918 H1N1 and 3.0% for H7). Mock-vaccinated animals all died following challenge. In the second group of experiments, two of the challenge viruses expressed HAs from different strains of the same subtype, but were not antigenically matched to the vaccine HAs (intrasubtypic heterologous challenge with H5N1 and H7N9; FIG. 8B). Here, vaccinated mice also showed 100% survival following A/Anhui/1/2013 (H7N9) virus challenge (weight loss nadir 3.7%), and 90% survival following A/Vietnam/1203/2004 highly pathogenic H5N1 virus challenge (weight loss nadir 10.4%). Mock-vaccinated animals showed rapid weight loss and 96% fatality (24/25) in aggregate. In the third group of experiments, four of the challenge viruses expressed HA subtypes not contained in the vaccine (heterosubtypic challenge): viruses expressing the 1957 pandemic H2 (H2N1), and avian H6N1, H10N1, and H11N1 IAV viruses (FIG. 8C). These vaccinated animals all showed 100% survival following challenge with H2N1 (weight loss nadir 17.2%), H10N1 (weight loss nadir 11.7%), and H11N1 (weight loss nadir 4.7%), and 83.3% survival following challenge with H6N1 (weight loss nadir 6.7%). Mock-vaccinated animals showed rapid weight loss and 92.5% fatality (37/40) in aggregate against these four challenge viruses. Thus, as shown in FIGS. 8A-8C, for all challenge groups, vaccinated mice had significantly reduced weight loss compared to mock-vaccinated mice (two-tailed, unpaired Student's t-test; Welch's correction; p<0.01).

In addition, vaccinated mice had significantly reduced viral lung titers (e.g., ~0.5-5 log$_{10}$ PFU) compared to mock-vaccinated mice for each of the four viruses (FIGS. 9A-9D, each group n=5, two-tailed Student's t-test; p<0.01). Mice vaccinated but not challenged until 6 months after vaccination also showed significant protection from lethal challenge with H7N9 and H10N1 influenza virus subtypes (FIG. 10A). Mice showed 100% survival following heterologous (intrasubtypic) challenge with H7N9 and 80% survival following heterosubtypic challenge with H10N1 (FIG. 10A). In each case, mock-vaccinated animals showed 80% fatality following challenge.

Older adults are particularly susceptible to severe disease following IAV infection and in this group vaccine is less efficacious than in younger adults. To evaluate the VLP cocktail in older animals, 8-month-old mice were vaccinated and boosted as above and then heterosubtypically challenged with H10N1. Aged mice (vaccinated at approximately 1 year of age) were also significantly protected from H10N1 influenza virus challenge (FIG. 10B). 66.7% of VLP-vaccinated aged mice survived lethal H10N1 virus challenge, compared with no survival of mock-vaccinated aged mice (FIG. 10B); viral lung titers were reduced by approximately 1 log$_{10}$ PFU compared to mock-vaccinated animals.

Example 6

Generation of VLP Vaccine and Testing in Mice

A polyvalent intranasal vaccine formulation that includes of mixture of HA VLPs separately expressing H1, H2, H3, H5, H7, and optionally H9, and NA VLPs separately expressing N1 and N2 will be generated as described in Example 1, and administered to mice as described in Example 2 (but both does of VLPs administered will be the same, as in Example 3). The VLPs will also contain M1 and M2. The polyvalent VLP composition will also contain MPL as the adjuvant. One skilled in the art will appreciate that other polyvalent influenza VLP compositions provided herein can be similarly tested.

Mice will be subsequently (4 to 6 weeks following the first VLP administration) challenged separately with a lethal dose (10×MLD$_{50}$) a variety of pathogenic influenza virus including the 1918 H1N1, 1957 H2N2, 1968 H3N2, and 2009 H1N1 pandemic viruses, highly pathogenic H5N1, H7N9, and H6N1 avian influenza viruses, and other relevant challenge viruses.

Mice will be evaluated for survival and vaccine-induced immunity, for example, by hemagglutination inhibition, microneutralization, and anti-HA stalk assays along with neuraminidase inhibition assays. Vaccinated animals will also be assessed for respiratory IgA and systemic IgG, T-cell responses, viral lung titers and pathology, and immune responses by transcriptomics and cytokine ELISAs.

It is expected that this polyvalent mixture of VLPs will protect the mice from challenge with all of these viruses.

Example 7

Generation of VLP Vaccine and Testing in Ferrets

A polyvalent intranasal vaccine formulation that includes of mixture of HA VLPs separately expressing H1, H2, H3, H5, H7, and optionally H9, and NA VLPs separately expressing N1 and N2 will be generated as described in Example 1, and administered to ferrets as generally described in Example 2 (but both does of VLPs administered will be the same, as in Example 3). The VLPs will also contain M1 and M2. The polyvalent VLP composition will also contain MPL as the adjuvant. One skilled in the art will appreciate that other polyvalent influenza VLP compositions provided herein can be similarly tested.

Fitch ferrets (*Mustela putorius* faro, female, 6-12-months of age), influenza naïve and de-scented, can be purchased from Marshall Farms (Sayre, Pa., USA). Ferrets are pair housed in stainless steel cages (Shor-line, Kansas City, Kans., USA) containing Sani-chips Laboratory Animal Bedding (P. J. Murphy Forest Products, Montville, N.J., USA). Ferrets are provided with Teklad Global Ferret Diet (Harlan Teklad, Madison, Wis., USA) and fresh water ad libitum.

Ferrets are administered i.n. with two doses of polyvalent influenza VLP compositions (2-10 µg each HA/NA), at week 0 and then boosted with the same dose at week 3. Animals are monitored for adverse events including weight loss, temperature, decrease in activity, nasal discharge, sneezing and diarrhea weekly during the vaccination regimen. Prior to vaccination, animals are confirmed by HA1 assay to be seronegative for circulating influenza A and influenza B viruses. Fourteen to twenty-one days after each vaccination, blood is collected from anesthetized ferrets via the anterior vena cava and transferred to a microfuge tube. Tubes are centrifuged and sera is removed and frozen at $-80\pm5°$ C. The serum can be analyzed for immune response, for example by HA1 serum antibody titer.

One to three weeks after final vaccination, ferrets are challenged separately with a lethal dose ($10 \times MLD_{50}$) intranasally with a variety of pathogenic influenza virus including the 1918 H1N1, 1957 H2N2, 1968 H3N2, and 2009 H1N1 pandemic viruses, highly pathogenic H5N1, H7N9, and H6N1 avian influenza viruses, and other relevant challenge viruses. After infection, ferrets are monitored daily for weight loss, disease signs and death for 14 days after infection. Individual body weights, sickness scores, and death are recorded for each group on each day after inoculation. Nasal washes are performed by instilling 3 ml of PBS into the nares of anesthetized ferrets each day for 7 days after inoculation. Washes are collected and stored at $-80°$ C. until use. Serum can also be collected.

Ferrets will be evaluated for survival and vaccine-induced immunity, for example, by hemagglutination inhibition, microneutralization, and anti-HA stalk assays along with neuraminidase inhibition assays. Vaccinated animals will also be assessed for respiratory IgA and systemic IgG, T-cell responses, viral lung titers and pathology, and immune responses by transcriptomics and cytokine ELISAs.

It is expected that this polyvalent mixture of VLPs will protect the ferrets from challenge with all of these viruses.

Example 8

Human Clinical Trials

After the selection of optimal broadly cross-reactive VLP vaccines in experimental animals, studies will be conducted in human volunteers with polyvalent influenza VLPs (for example that are produced using the Good Manufacturing Practice (GMP) such as from Paragon Bioservice, Baltimore, Md.). In some examples the VLPs will also contain M1 and M2. The polyvalent VLP composition in some examples will also contain MPL as the adjuvant.

A polyvalent intranasal vaccine formulation that includes of mixture of HA VLPs separately expressing H1, H2, H3, H5, H7, and H9, and NA VLPs separately expressing N1 and N2 will be generated using GMP methods, and administered to humans intransally. One skilled in the art will appreciate that other polyvalent influenza VLP compositions provided herein can be similarly tested.

Briefly, humans are vaccinated intranasally with a polyvalent mixture of VLPs (10 µg-20 µg, such as 15 µg each HA/NA). About 3-12 weeks later (such as 3, 4, 5, 6, 7, 8, 9, 10, 11, or 12 weeks later), the humans are boosted with the same mixture. A second group of humans are mock vaccinated (for example with saline). Blood and nasal samples can be obtained and stored. Patients will be monitored for any adverse events (AEs) during the course of study. Since VLP vaccines are not infectious, they are expected to have an excellent safety profile.

If the VLP composition is shown to be safe in Phase I trials, Phase II efficacy trials will be performed using a human volunteer influenza challenge model, as developed at the NIH Clinical Center (e.g., see Memoli et al., Validation of a Wild-Type Influenza A Human Challenge Model: H1N1pdMIST, An A(H1N1)pdm09 Dose Finding IND Study). Subjects will be screened for health status and by HA1 assay for low titers (<1:10) against the challenge 2009 pandemic H1N1 virus. Screened patients enrolled in the study will be intranasally vaccinated with the polyvalent mixture of VLPs (cohort 1) or given a mock vaccination with saline (cohort 2). They will be boosted at three weeks, and then at six weeks their serologic titers will be assessed by HA1 or other assays, and the subjects will be challenged with a dose of virus validated to induce influenza illness and shedding in >60% subjects pre-challenge HA1 titers <1:10. Vaccine efficacy will be assessed by development of serologic responses to vaccination, reduction in symptoms, reduction in viral titers, and/or reduction in duration of viral shedding.

In view of the many possible embodiments to which the principles of the disclosure may be applied, it should be recognized that the illustrated embodiments are only examples of the disclosure and should not be taken as limiting the scope of the invention. Rather, the scope of the disclosure is defined by the following claims. I therefore claim as my invention all that comes within the scope and spirit of these claims.

SEQUENCE LISTING

```
<160> NUMBER OF SEQ ID NOS: 39

<210> SEQ ID NO 1
<211> LENGTH: 1744
<212> TYPE: DNA
<213> ORGANISM: Influenza A virus
<220> FEATURE:
```

<221> NAME/KEY: CDS
<222> LOCATION: (19)..(1719)

<400> SEQUENCE: 1

```
ataatcaaat caaccaag atg gaa gca aaa cta ttt gta cta ttc tgt aca         51
                    Met Glu Ala Lys Leu Phe Val Leu Phe Cys Thr
                    1               5                   10 ttc act gta ctg aaa gct gac acc atc tgt gtg ggc tac cat gca aac         99
Phe Thr Val Leu Lys Ala Asp Thr Ile Cys Val Gly Tyr His Ala Asn
        15                  20                  25 aac tct aca gac act gtt gac aca gta ctg gaa aag aat gtg acc gtg       147
Asn Ser Thr Asp Thr Val Asp Thr Val Leu Glu Lys Asn Val Thr Val
30                  35                  40 act cac tca gtg aat ctg ctc gaa gac aac cat aat ggg aaa ctc tgc       195
Thr His Ser Val Asn Leu Leu Glu Asp Asn His Asn Gly Lys Leu Cys
    45                  50                  55 agc ctg aac ggg ata gct ccc cta caa ctg ggg aag tgc aat gtg gcg       243
Ser Leu Asn Gly Ile Ala Pro Leu Gln Leu Gly Lys Cys Asn Val Ala
60                  65                  70                  75 gga tgg ctc ctt ggc aat cca gaa tgt gac ctt tta ctc act gcg aac       291
Gly Trp Leu Leu Gly Asn Pro Glu Cys Asp Leu Leu Leu Thr Ala Asn
                80                  85                  90 tca tgg tcc tac ata ata gaa act tcc aat tcg gaa aac gga aca tgc       339
Ser Trp Ser Tyr Ile Ile Glu Thr Ser Asn Ser Glu Asn Gly Thr Cys
        95                  100                 105 tac ccc ggt gaa ttc ata gat tat gaa gag tta aga gag cag tta agt       387
Tyr Pro Gly Glu Phe Ile Asp Tyr Glu Glu Leu Arg Glu Gln Leu Ser
            110                 115                 120 tca gtt tcc tca ttt gaa aag ttt gaa att ttc ccg aag gca agc tca       435
Ser Val Ser Ser Phe Glu Lys Phe Glu Ile Phe Pro Lys Ala Ser Ser
    125                 130                 135 tgg cca aat cat gag aca acc aaa ggt gtt aca gcc gca tgc tct tac       483
Trp Pro Asn His Glu Thr Thr Lys Gly Val Thr Ala Ala Cys Ser Tyr
140                 145                 150                 155 tct gga gcc agc agt ttt tat cgg aac ttg ctg tgg ata aca aag aag       531
Ser Gly Ala Ser Ser Phe Tyr Arg Asn Leu Leu Trp Ile Thr Lys Lys
                160                 165                 170 ggg aat tca tac cca aaa ctc agc aaa tca tac acg aac aac aag ggg       579
Gly Asn Ser Tyr Pro Lys Leu Ser Lys Ser Tyr Thr Asn Asn Lys Gly
            175                 180                 185 aag gaa gtg ctt gtg ctc tgg ggg gtg cat cac cct cca act gcc agc       627
Lys Glu Val Leu Val Leu Trp Gly Val His His Pro Pro Thr Ala Ser
                190                 195                 200 gag cag caa agt cta tat cag aac gct gac gca tat gtg tca gtt gga       675
Glu Gln Gln Ser Leu Tyr Gln Asn Ala Asp Ala Tyr Val Ser Val Gly
    205                 210                 215 tca tca aaa tac aac cga aga ttc act ccg gag ata gca gct aga cct       723
Ser Ser Lys Tyr Asn Arg Arg Phe Thr Pro Glu Ile Ala Ala Arg Pro
220                 225                 230                 235 aaa gtt aga gga cag gca ggc aga atg aac tat tat tgg aca cta ttg       771
Lys Val Arg Gly Gln Ala Gly Arg Met Asn Tyr Tyr Trp Thr Leu Leu
                240                 245                 250 gac cag gga gac acc ata aca ttt gaa gca act ggg aat ttg ata gca       819
Asp Gln Gly Asp Thr Ile Thr Phe Glu Ala Thr Gly Asn Leu Ile Ala
            255                 260                 265 cca tgg tat gct ttt gca ttg aac aag ggg tct gac tcc gga att ata       867
Pro Trp Tyr Ala Phe Ala Leu Asn Lys Gly Ser Asp Ser Gly Ile Ile
        270                 275                 280 aca tca gat gct cca gtt cac aat tgt gac aca aag tgc caa acc cct       915
Thr Ser Asp Ala Pro Val His Asn Cys Asp Thr Lys Cys Gln Thr Pro
```

```
                285                 290                 295
cat ggg gct ttg aac agc agc ctt cct ttc cag aat gta cat cct atc      963
His Gly Ala Leu Asn Ser Ser Leu Pro Phe Gln Asn Val His Pro Ile
300                 305                 310                 315 act att gga gaa tgt ccc aaa tac gtc aag agc acc aag cta aga atg     1011
Thr Ile Gly Glu Cys Pro Lys Tyr Val Lys Ser Thr Lys Leu Arg Met
                320                 325                 330 gca aca gga cta aga aat gtc cca tcc att caa tcc aga gga cta ttt    1059
Ala Thr Gly Leu Arg Asn Val Pro Ser Ile Gln Ser Arg Gly Leu Phe
            335                 340                 345 gga gca att gct gga ttc att gag gga gga tgg aca ggc atg ata gat    1107
Gly Ala Ile Ala Gly Phe Ile Glu Gly Gly Trp Thr Gly Met Ile Asp
        350                 355                 360 gga tgg tat gga tat cat cat cag aat gag cag gga tca gga tat gct   1155
Gly Trp Tyr Gly Tyr His His Gln Asn Glu Gln Gly Ser Gly Tyr Ala
    365                 370                 375 gcc gat cag aaa agc acg cag aat gcg att gac ggg atc aca aat aag   1203
Ala Asp Gln Lys Ser Thr Gln Asn Ala Ile Asp Gly Ile Thr Asn Lys
380                 385                 390                 395 gtg aat tcg gta att gag aag atg aac act caa ttc act gca gtg ggc   1251
Val Asn Ser Val Ile Glu Lys Met Asn Thr Gln Phe Thr Ala Val Gly
                400                 405                 410 aag gaa ttc aac aac tta gaa agg aga att gaa aat ttg aat aag aag   1299
Lys Glu Phe Asn Asn Leu Glu Arg Arg Ile Glu Asn Leu Asn Lys Lys
            415                 420                 425 gtc gat gat ggg ttc ttg gat gtt tgg aca tat aat gcc gaa ctg ctc   1347
Val Asp Asp Gly Phe Leu Asp Val Trp Thr Tyr Asn Ala Glu Leu Leu
        430                 435                 440 gtc cta ctt gag aat gaa agg act ctg gac ttc cat gac tcc aat gtg   1395
Val Leu Leu Glu Asn Glu Arg Thr Leu Asp Phe His Asp Ser Asn Val
    445                 450                 455 aga aat tta tat gag aaa gtc aaa tca caa ttg agg aac aat gcc aaa   1443
Arg Asn Leu Tyr Glu Lys Val Lys Ser Gln Leu Arg Asn Asn Ala Lys
460                 465                 470                 475 gaa ctt ggg aat ggt tgt ttt gag ttc tac cac aaa tgt gat gat gag   1491
Glu Leu Gly Asn Gly Cys Phe Glu Phe Tyr His Lys Cys Asp Asp Glu
                480                 485                 490 tgc atg gaa agt gtg aag aac ggc aca tat gac tat ccc aaa tat tca   1539
Cys Met Glu Ser Val Lys Asn Gly Thr Tyr Asp Tyr Pro Lys Tyr Ser
            495                 500                 505 gaa gaa tcc aaa ttg aac cga gaa gaa ata gac gga gtg aaa cta gaa   1587
Glu Glu Ser Lys Leu Asn Arg Glu Glu Ile Asp Gly Val Lys Leu Glu
        510                 515                 520 tca atg gga gtt tac caa att ttg gcg atc tat tcc aca gtc gcc agt   1635
Ser Met Gly Val Tyr Gln Ile Leu Ala Ile Tyr Ser Thr Val Ala Ser
    525                 530                 535 tct cta gtc ttg tta gtc tcc ctg ggg gca atc agc ttc tgg atg tgc   1683
Ser Leu Val Leu Leu Val Ser Leu Gly Ala Ile Ser Phe Trp Met Cys
540                 545                 550                 555 tct aat ggg tca ttg caa tgc aga ata tgc att tag agcttgaact        1729
Ser Asn Gly Ser Leu Gln Cys Arg Ile Cys Ile
                560                 565 tcaaaatgta tggaa                                                   1744

<210> SEQ ID NO 2
<211> LENGTH: 566
<212> TYPE: PRT
<213> ORGANISM: Influenza A virus

<400> SEQUENCE: 2
```

```
Met Glu Ala Lys Leu Phe Val Leu Phe Cys Thr Phe Thr Val Leu Lys
1               5                   10                  15

Ala Asp Thr Ile Cys Val Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Asn His Asn Gly Lys Leu Cys Ser Leu Asn Gly Ile
50                      55                  60

Ala Pro Leu Gln Leu Gly Lys Cys Asn Val Ala Gly Trp Leu Leu Gly
65                  70                  75                  80

Asn Pro Glu Cys Asp Leu Leu Leu Thr Ala Asn Ser Trp Ser Tyr Ile
                85                  90                  95

Ile Glu Thr Ser Asn Ser Glu Asn Gly Thr Cys Tyr Pro Gly Glu Phe
                100                 105                 110

Ile Asp Tyr Glu Glu Leu Arg Glu Gln Leu Ser Ser Val Ser Ser Phe
            115                 120                 125

Glu Lys Phe Glu Ile Phe Pro Lys Ala Ser Ser Trp Pro Asn His Glu
            130                 135                 140

Thr Thr Lys Gly Val Thr Ala Ala Cys Ser Tyr Ser Gly Ala Ser Ser
145                 150                 155                 160

Phe Tyr Arg Asn Leu Leu Trp Ile Thr Lys Lys Gly Asn Ser Tyr Pro
                165                 170                 175

Lys Leu Ser Lys Ser Tyr Thr Asn Asn Lys Gly Lys Glu Val Leu Val
                180                 185                 190

Leu Trp Gly Val His His Pro Pro Thr Ala Ser Glu Gln Gln Ser Leu
            195                 200                 205

Tyr Gln Asn Ala Asp Ala Tyr Val Ser Val Gly Ser Ser Lys Tyr Asn
210                 215                 220

Arg Arg Phe Thr Pro Glu Ile Ala Ala Arg Pro Lys Val Arg Gly Gln
225                 230                 235                 240

Ala Gly Arg Met Asn Tyr Tyr Trp Thr Leu Leu Asp Gln Gly Asp Thr
                245                 250                 255

Ile Thr Phe Glu Ala Thr Gly Asn Leu Ile Ala Pro Trp Tyr Ala Phe
                260                 265                 270

Ala Leu Asn Lys Gly Ser Asp Ser Gly Ile Ile Thr Ser Asp Ala Pro
                275                 280                 285

Val His Asn Cys Asp Thr Lys Cys Gln Thr Pro His Gly Ala Leu Asn
            290                 295                 300

Ser Ser Leu Pro Phe Gln Asn Val His Pro Ile Thr Ile Gly Glu Cys
305                 310                 315                 320

Pro Lys Tyr Val Lys Ser Thr Lys Leu Arg Met Ala Thr Gly Leu Arg
                325                 330                 335

Asn Val Pro Ser Ile Gln Ser Arg Gly Leu Phe Gly Ala Ile Ala Gly
                340                 345                 350

Phe Ile Glu Gly Gly Trp Thr Gly Met Ile Asp Gly Trp Tyr Gly Tyr
            355                 360                 365

His His Gln Asn Glu Gln Gly Ser Gly Tyr Ala Ala Asp Gln Lys Ser
            370                 375                 380

Thr Gln Asn Ala Ile Asp Gly Ile Thr Asn Lys Val Asn Ser Val Ile
385                 390                 395                 400

Glu Lys Met Asn Thr Gln Phe Thr Ala Val Gly Lys Glu Phe Asn Asn
                405                 410                 415
```

```
Leu Glu Arg Arg Ile Glu Asn Leu Asn Lys Lys Val Asp Asp Gly Phe
            420                 425                 430

Leu Asp Val Trp Thr Tyr Asn Ala Glu Leu Leu Val Leu Leu Glu Asn
            435                 440                 445

Glu Arg Thr Leu Asp Phe His Asp Ser Asn Val Arg Asn Leu Tyr Glu
        450                 455                 460

Lys Val Lys Ser Gln Leu Arg Asn Asn Ala Lys Glu Leu Gly Asn Gly
465                 470                 475                 480

Cys Phe Glu Phe Tyr His Lys Cys Asp Asp Glu Cys Met Glu Ser Val
            485                 490                 495

Lys Asn Gly Thr Tyr Asp Tyr Pro Lys Tyr Ser Glu Glu Ser Lys Leu
            500                 505                 510

Asn Arg Glu Glu Ile Asp Gly Val Lys Leu Glu Ser Met Gly Val Tyr
        515                 520                 525

Gln Ile Leu Ala Ile Tyr Ser Thr Val Ala Ser Ser Leu Val Leu Leu
        530                 535                 540

Val Ser Leu Gly Ala Ile Ser Phe Trp Met Cys Ser Asn Gly Ser Leu
545                 550                 555                 560

Gln Cys Arg Ile Cys Ile
                565

<210> SEQ ID NO 3
<211> LENGTH: 1701
<212> TYPE: DNA
<213> ORGANISM: Influenza A virus
<220> FEATURE:
<221> NAME/KEY: CDS
<222> LOCATION: (1)..(1701)

<400> SEQUENCE: 3 atg gag gca aga cta ctg gtc ttg tta tgt gca ttt gca gct aca aat        48
Met Glu Ala Arg Leu Leu Val Leu Leu Cys Ala Phe Ala Ala Thr Asn
1               5                   10                  15 gca gac aca ata tgt ata ggc tac cat gcg aat aac tca acc gac act        96
Ala Asp Thr Ile Cys Ile Gly Tyr His Ala Asn Asn Ser Thr Asp Thr
            20                  25                  30 gtt gac aca gta ctc gaa aag aat gtg acc gtg aca cac tct gtt aac       144
Val Asp Thr Val Leu Glu Lys Asn Val Thr Val Thr His Ser Val Asn
        35                  40                  45 ctg ctc gaa gac agc cac aac gga aaa cta tgt aaa tta aaa gga ata       192
Leu Leu Glu Asp Ser His Asn Gly Lys Leu Cys Lys Leu Lys Gly Ile
    50                  55                  60 gcc cca tta caa ttg ggg aaa tgt aat atc gcc gga tgg ctc ttg gga       240
Ala Pro Leu Gln Leu Gly Lys Cys Asn Ile Ala Gly Trp Leu Leu Gly
65                  70                  75                  80 aac ccg gaa tgc gat tta ctg ctc aca gcg agc tca tgg tcc tat att       288
Asn Pro Glu Cys Asp Leu Leu Leu Thr Ala Ser Ser Trp Ser Tyr Ile
                85                  90                  95 gta gaa aca tcg aac tca gag aat gga aca tgt tac cca gga gat ttc       336
Val Glu Thr Ser Asn Ser Glu Asn Gly Thr Cys Tyr Pro Gly Asp Phe
            100                 105                 110 atc gac tat gaa gaa ctg agg gag caa ttg agc tca gtg tca tcg ttt       384
Ile Asp Tyr Glu Glu Leu Arg Glu Gln Leu Ser Ser Val Ser Ser Phe
        115                 120                 125 gaa aaa ttc gaa ata ttt ccc aag aca agc tcg tgg ccc aat cat gaa       432
Glu Lys Phe Glu Ile Phe Pro Lys Thr Ser Ser Trp Pro Asn His Glu
    130                 135                 140 aca acc aaa ggt gta acg gca gca tgc tcc tat gcg gga gca agc agt       480
Thr Thr Lys Gly Val Thr Ala Ala Cys Ser Tyr Ala Gly Ala Ser Ser
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |     |
| ttt | tac | aga | aat | ttg | ctg | tgg | ctg | aca | aag | aag | gga | agc | tca | tac | cca | 528 |
| Phe | Tyr | Arg | Asn | Leu | Leu | Trp | Leu | Thr | Lys | Lys | Gly | Ser | Ser | Tyr | Pro |     |
|     |     |     |     |     | 165 |     |     |     |     | 170 |     |     |     |     | 175 |     |
| aag | ctt | agc | aag | tcc | tat | gtg | aac | aat | aaa | ggg | aaa | gaa | gtc | ctt | gta | 576 |
| Lys | Leu | Ser | Lys | Ser | Tyr | Val | Asn | Asn | Lys | Gly | Lys | Glu | Val | Leu | Val |     |
|     |     |     | 180 |     |     |     |     | 185 |     |     |     |     | 190 |     |     |     |
| cta | tgg | ggt | gtt | cat | cat | ccg | cct | acc | ggt | act | gat | caa | cag | agt | ctc | 624 |
| Leu | Trp | Gly | Val | His | His | Pro | Pro | Thr | Gly | Thr | Asp | Gln | Gln | Ser | Leu |     |
|     |     | 195 |     |     |     |     | 200 |     |     |     |     | 205 |     |     |     |     |
| tat | cag | aat | gca | gat | gct | tat | gtc | tct | gta | ggg | tca | tca | aaa | tat | aac | 672 |
| Tyr | Gln | Asn | Ala | Asp | Ala | Tyr | Val | Ser | Val | Gly | Ser | Ser | Lys | Tyr | Asn |     |
|     | 210 |     |     |     |     | 215 |     |     |     |     | 220 |     |     |     |     |     |
| agg | aga | ttc | acc | ccg | gaa | ata | gca | gcg | aga | ccc | aaa | gta | aga | gat | caa | 720 |
| Arg | Arg | Phe | Thr | Pro | Glu | Ile | Ala | Ala | Arg | Pro | Lys | Val | Arg | Asp | Gln |     |
| 225 |     |     |     |     | 230 |     |     |     |     | 235 |     |     |     |     | 240 |     |
| gct | ggg | agg | atg | aac | tat | tac | tgg | aca | tta | cta | gaa | ccc | gga | gac | aca | 768 |
| Ala | Gly | Arg | Met | Asn | Tyr | Tyr | Trp | Thr | Leu | Leu | Glu | Pro | Gly | Asp | Thr |     |
|     |     |     |     |     | 245 |     |     |     |     | 250 |     |     |     |     | 255 |     |
| ata | aca | ttt | gag | gca | act | gga | aat | cta | ata | gca | cca | tgg | tat | gct | ttc | 816 |
| Ile | Thr | Phe | Glu | Ala | Thr | Gly | Asn | Leu | Ile | Ala | Pro | Trp | Tyr | Ala | Phe |     |
|     |     |     | 260 |     |     |     |     | 265 |     |     |     |     | 270 |     |     |     |
| gca | ctg | aat | aga | ggt | tct | gga | tcc | ggt | atc | atc | act | tca | gac | gca | cca | 864 |
| Ala | Leu | Asn | Arg | Gly | Ser | Gly | Ser | Gly | Ile | Ile | Thr | Ser | Asp | Ala | Pro |     |
|     |     | 275 |     |     |     |     | 280 |     |     |     |     | 285 |     |     |     |     |
| gtg | cat | gat | tgt | aac | acg | aag | tgt | caa | aca | ccc | cat | ggt | gct | ata | aac | 912 |
| Val | His | Asp | Cys | Asn | Thr | Lys | Cys | Gln | Thr | Pro | His | Gly | Ala | Ile | Asn |     |
|     | 290 |     |     |     |     | 295 |     |     |     |     | 300 |     |     |     |     |     |
| agc | agt | ctc | cct | ttc | cag | aat | ata | cat | cca | gtc | aca | ata | gga | gag | tgc | 960 |
| Ser | Ser | Leu | Pro | Phe | Gln | Asn | Ile | His | Pro | Val | Thr | Ile | Gly | Glu | Cys |     |
| 305 |     |     |     |     | 310 |     |     |     |     | 315 |     |     |     |     | 320 |     |
| cca | aaa | tac | gtc | agg | agt | acc | aaa | ttg | agg | atg | gct | aca | gga | cta | aga | 1008 |
| Pro | Lys | Tyr | Val | Arg | Ser | Thr | Lys | Leu | Arg | Met | Ala | Thr | Gly | Leu | Arg |     |
|     |     |     |     | 325 |     |     |     |     | 330 |     |     |     |     | 335 |     |     |
| aac | att | cca | tct | att | caa | tcc | agg | ggt | cta | ttt | gga | gcc | att | gcc | ggt | 1056 |
| Asn | Ile | Pro | Ser | Ile | Gln | Ser | Arg | Gly | Leu | Phe | Gly | Ala | Ile | Ala | Gly |     |
|     |     |     | 340 |     |     |     |     | 345 |     |     |     |     | 350 |     |     |     |
| ttt | att | gag | ggg | gga | tgg | act | gga | atg | ata | gat | gga | tgg | tat | ggt | tat | 1104 |
| Phe | Ile | Glu | Gly | Gly | Trp | Thr | Gly | Met | Ile | Asp | Gly | Trp | Tyr | Gly | Tyr |     |
|     |     |     |     | 355 |     |     |     |     | 360 |     |     |     |     | 365 |     |     |
| cat | cat | cag | aat | gaa | cag | gga | tca | ggc | tat | gca | gcg | gat | caa | aaa | agc | 1152 |
| His | His | Gln | Asn | Glu | Gln | Gly | Ser | Gly | Tyr | Ala | Ala | Asp | Gln | Lys | Ser |     |
|     |     | 370 |     |     |     |     | 375 |     |     |     |     | 380 |     |     |     |     |
| aca | caa | aat | gcc | att | gac | ggg | att | aca | aac | aag | gtg | aat | tct | gtt | atc | 1200 |
| Thr | Gln | Asn | Ala | Ile | Asp | Gly | Ile | Thr | Asn | Lys | Val | Asn | Ser | Val | Ile |     |
| 385 |     |     |     |     | 390 |     |     |     |     | 395 |     |     |     |     | 400 |     |
| gag | aaa | atg | aac | acc | caa | ttc | aca | gca | gtg | ggt | aaa | gaa | ttc | aac | aac | 1248 |
| Glu | Lys | Met | Asn | Thr | Gln | Phe | Thr | Ala | Val | Gly | Lys | Glu | Phe | Asn | Asn |     |
|     |     |     |     | 405 |     |     |     |     | 410 |     |     |     |     | 415 |     |     |
| tta | gaa | aga | agg | ata | gaa | aat | tta | aat | aaa | aaa | gtc | gat | gat | gga | ttt | 1296 |
| Leu | Glu | Arg | Arg | Ile | Glu | Asn | Leu | Asn | Lys | Lys | Val | Asp | Asp | Gly | Phe |     |
|     |     |     | 420 |     |     |     |     | 425 |     |     |     |     | 430 |     |     |     |
| ctg | gat | att | tgg | aca | tat | aat | gca | gaa | ttg | tta | gtt | cta | ctg | gaa | aat | 1344 |
| Leu | Asp | Ile | Trp | Thr | Tyr | Asn | Ala | Glu | Leu | Leu | Val | Leu | Leu | Glu | Asn |     |
|     |     | 435 |     |     |     |     | 440 |     |     |     |     | 445 |     |     |     |     |
| gaa | aga | acc | ctg | gat | ttc | cat | gac | tca | aat | gta | agg | aat | ctg | tat | gag | 1392 |
| Glu | Arg | Thr | Leu | Asp | Phe | His | Asp | Ser | Asn | Val | Arg | Asn | Leu | Tyr | Glu |     |
|     | 450 |     |     |     |     | 455 |     |     |     |     | 460 |     |     |     |     |     |
| aaa | gta | aaa | agc | caa | tta | aag | aat | aat | gcc | aag | gaa | atc | gga | aat | gga | 1440 |

```
Lys Val Lys Ser Gln Leu Lys Asn Asn Ala Lys Glu Ile Gly Asn Gly
465                 470                 475                 480 tgt ttt gag ttc tac cac aag tgt gac gat gca tgc atg gaa agt gta      1488
Cys Phe Glu Phe Tyr His Lys Cys Asp Asp Ala Cys Met Glu Ser Val
                    485                 490                 495 aga aat ggg act tat gat tac cca aaa tat tca gaa gaa tca aag ttg      1536
Arg Asn Gly Thr Tyr Asp Tyr Pro Lys Tyr Ser Glu Glu Ser Lys Leu
                500                 505                 510 aac aga gaa gaa ata gat gga gtg aaa tta gaa tca atg ggg gtc tat      1584
Asn Arg Glu Glu Ile Asp Gly Val Lys Leu Glu Ser Met Gly Val Tyr
            515                 520                 525 cag att ctg gcg atc tac tca act gtc gcc agt tca cta gtg ctg tta      1632
Gln Ile Leu Ala Ile Tyr Ser Thr Val Ala Ser Ser Leu Val Leu Leu
        530                 535                 540 gtc tcc ctg ggg gca atc agc ttc tgg atg tgt tct aat ggg tct ttg      1680
Val Ser Leu Gly Ala Ile Ser Phe Trp Met Cys Ser Asn Gly Ser Leu
545                 550                 555                 560 cag tgc aga ata tgc att tga                                          1701
Gln Cys Arg Ile Cys Ile
                565

<210> SEQ ID NO 4
<211> LENGTH: 566
<212> TYPE: PRT
<213> ORGANISM: Influenza A virus

<400> SEQUENCE: 4

Met Glu Ala Arg Leu Leu Val Leu Leu Cys Ala Phe Ala Ala Thr Asn
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Lys Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Leu Leu Leu Thr Ala Ser Ser Trp Ser Tyr Ile
                85                  90                  95

Val Glu Thr Ser Asn Ser Glu Asn Gly Thr Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Lys Phe Glu Ile Phe Pro Lys Thr Ser Ser Trp Pro Asn His Glu
        130                 135                 140

Thr Thr Lys Gly Val Thr Ala Ala Cys Ser Tyr Ala Gly Ala Ser Ser
145                 150                 155                 160

Phe Tyr Arg Asn Leu Leu Trp Leu Thr Lys Lys Gly Ser Ser Tyr Pro
                165                 170                 175

Lys Leu Ser Lys Ser Tyr Val Asn Asn Lys Gly Lys Glu Val Leu Val
                180                 185                 190

Leu Trp Gly Val His His Pro Pro Thr Gly Thr Asp Gln Gln Ser Leu
            195                 200                 205

Tyr Gln Asn Ala Asp Ala Tyr Val Ser Val Gly Ser Ser Lys Tyr Asn
        210                 215                 220

Arg Arg Phe Thr Pro Glu Ile Ala Ala Arg Pro Lys Val Arg Asp Gln
225                 230                 235                 240
```

```
Ala Gly Arg Met Asn Tyr Tyr Trp Thr Leu Leu Glu Pro Gly Asp Thr
            245                 250                 255
Ile Thr Phe Glu Ala Thr Gly Asn Leu Ile Ala Pro Trp Tyr Ala Phe
        260                 265                 270
Ala Leu Asn Arg Gly Ser Gly Ser Gly Ile Ile Thr Ser Asp Ala Pro
        275                 280                 285
Val His Asp Cys Asn Thr Lys Cys Gln Thr Pro His Gly Ala Ile Asn
290                 295                 300
Ser Ser Leu Pro Phe Gln Asn Ile His Pro Val Thr Ile Gly Glu Cys
305                 310                 315                 320
Pro Lys Tyr Val Arg Ser Thr Lys Leu Arg Met Ala Thr Gly Leu Arg
            325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Ile Asp Gly Trp Tyr Gly Tyr
            355                 360                 365
His His Gln Asn Glu Gln Gly Ser Gly Tyr Ala Ala Asp Gln Lys Ser
        370                 375                 380
Thr Gln Asn Ala Ile Asp Gly Ile Thr Asn Lys Val Asn Ser Val Ile
385                 390                 395                 400
Glu Lys Met Asn Thr Gln Phe Thr Ala Val Gly Lys Glu Phe Asn Asn
            405                 410                 415
Leu Glu Arg Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
Glu Arg Thr Leu Asp Phe His Asp Ser Asn Val Arg Asn Leu Tyr Glu
        450                 455                 460
Lys Val Lys Ser Gln Leu Lys Asn Asn Ala Lys Glu Ile Gly Asn Gly
465                 470                 475                 480
Cys Phe Glu Phe Tyr His Lys Cys Asp Asp Ala Cys Met Glu Ser Val
            485                 490                 495
Arg Asn Gly Thr Tyr Asp Tyr Pro Lys Tyr Ser Glu Glu Ser Lys Leu
            500                 505                 510
Asn Arg Glu Glu Ile Asp Gly Val Lys Leu Glu Ser Met Gly Val Tyr
        515                 520                 525
Gln Ile Leu Ala Ile Tyr Ser Thr Val Ala Ser Ser Leu Val Leu Leu
        530                 535                 540
Val Ser Leu Gly Ala Ile Ser Phe Trp Met Cys Ser Asn Gly Ser Leu
545                 550                 555                 560
Gln Cys Arg Ile Cys Ile
            565
```

<210> SEQ ID NO 5
<211> LENGTH: 1738
<212> TYPE: DNA
<213> ORGANISM: Influenza A virus
<220> FEATURE:
<221> NAME/KEY: CDS
<222> LOCATION: (29)..(1717)

<400> SEQUENCE: 5

```
ttataccatg gacaaccgaa caaagaca atg act atc acc ttt ctc att ctc    52
                                Met Thr Ile Thr Phe Leu Ile Leu
                                 1               5
```

```
ctg ttc aca gta gtg aaa ggg gac caa ata tgt atc ggg tac cac gcc    100
Leu Phe Thr Val Val Lys Gly Asp Gln Ile Cys Ile Gly Tyr His Ala
 10              15                  20 aac aat tcc aca gag aaa gtc gac aca atc ttg gaa cga aac gtc acc    148
Asn Asn Ser Thr Glu Lys Val Asp Thr Ile Leu Glu Arg Asn Val Thr
 25              30                  35                  40 gtg act cat gcc aag aac att ctt gag aaa acg cac aat gga aag ttg    196
Val Thr His Ala Lys Asn Ile Leu Glu Lys Thr His Asn Gly Lys Leu
                 45                  50                  55 tgt aga tta agc ggg atc cct ccg ttg gaa ttg ggg gat tgc agc att    244
Cys Arg Leu Ser Gly Ile Pro Pro Leu Glu Leu Gly Asp Cys Ser Ile
                     60                  65                  70 gca ggt tgg ctc ctt gga aat cca gaa tgt gat cgg ctc cta agt gta    292
Ala Gly Trp Leu Leu Gly Asn Pro Glu Cys Asp Arg Leu Leu Ser Val
             75                  80                  85 cct gaa tgg tcc tat ata gtg gaa aag gaa aac cca gcg aat ggt ctg    340
Pro Glu Trp Ser Tyr Ile Val Glu Lys Glu Asn Pro Ala Asn Gly Leu
 90                  95                 100 tgt tac cca ggc agt ttc aat gat tat gag gaa ttg aaa cat ctc ctc    388
Cys Tyr Pro Gly Ser Phe Asn Asp Tyr Glu Glu Leu Lys His Leu Leu
105                 110                 115                 120 act agt gtg aca cat ttt gag aaa att aag att ctg ccc aga gat caa    436
Thr Ser Val Thr His Phe Glu Lys Ile Lys Ile Leu Pro Arg Asp Gln
                125                 130                 135 tgg act cag cac acg aca act ggt ggc tct cgg gcc tgt gca gta tct    484
Trp Thr Gln His Thr Thr Thr Gly Gly Ser Arg Ala Cys Ala Val Ser
                140                 145                 150 ggc aac ccg tca ttc ttc agg aac atg gtt tgg ctt aca aaa aag gga    532
Gly Asn Pro Ser Phe Phe Arg Asn Met Val Trp Leu Thr Lys Lys Gly
            155                 160                 165 tca aac tac cca gtt gcc caa aga tca tac aac aac aca agc ggg gag    580
Ser Asn Tyr Pro Val Ala Gln Arg Ser Tyr Asn Asn Thr Ser Gly Glu
170                 175                 180 caa atg ctg ata att tgg ggg ata cat cat ccc aat gac gat gcg gaa    628
Gln Met Leu Ile Ile Trp Gly Ile His His Pro Asn Asp Asp Ala Glu
185                 190                 195                 200 caa agg aca ctg tac cag aac gtg aga aca tat gtt tct gta ggc aca    676
Gln Arg Thr Leu Tyr Gln Asn Val Arg Thr Tyr Val Ser Val Gly Thr
                205                 210                 215 tca aca tta aat aag agg tca atc cct gaa ata gca aca agg ccc aaa    724
Ser Thr Leu Asn Lys Arg Ser Ile Pro Glu Ile Ala Thr Arg Pro Lys
                220                 225                 230 gtc aac gga caa ggg ggg aga atg gaa ttc tct tgg act cta ttg gaa    772
Val Asn Gly Gln Gly Gly Arg Met Glu Phe Ser Trp Thr Leu Leu Glu
            235                 240                 245 aca tgg gat gtc ata aat ttc gag agc act ggt aat tta att gca cca    820
Thr Trp Asp Val Ile Asn Phe Glu Ser Thr Gly Asn Leu Ile Ala Pro
250                 255                 260 gaa tat gga ttc aaa ata tcg aag aga gga agc tca gga att atg aag    868
Glu Tyr Gly Phe Lys Ile Ser Lys Arg Gly Ser Ser Gly Ile Met Lys
265                 270                 275                 280 aca gag aaa aca ctt gaa aat tgt gaa acc aaa tgt cag acc ccc ttg    916
Thr Glu Lys Thr Leu Glu Asn Cys Glu Thr Lys Cys Gln Thr Pro Leu
                285                 290                 295 ggg gca ata aat aca aca ttg cct ttt cac aac att cat cca ttg aca    964
Gly Ala Ile Asn Thr Thr Leu Pro Phe His Asn Ile His Pro Leu Thr
                300                 305                 310 ata ggt gaa tgt ccc aaa tat gta aag tca gat aga ttg gtt ttg gca    1012
Ile Gly Glu Cys Pro Lys Tyr Val Lys Ser Asp Arg Leu Val Leu Ala
                315                 320                 325
```

-continued

| | | |
|---|---|---|
| aca ggg cta aga aat gtc cct cag att gaa tca agg gga ttg ttt gga<br>Thr Gly Leu Arg Asn Val Pro Gln Ile Glu Ser Arg Gly Leu Phe Gly<br>330                              335                          340 | | 1060 |
| gca ata gct ggt ttt ata gaa ggc gga tgg caa gga atg att gat ggt<br>Ala Ile Ala Gly Phe Ile Glu Gly Gly Trp Gln Gly Met Ile Asp Gly<br>345                              350                          355                          360 | | 1108 |
| tgg tat ggg tat cat cac agc aat gat caa gga tca gga tat gca gca<br>Trp Tyr Gly Tyr His His Ser Asn Asp Gln Gly Ser Gly Tyr Ala Ala<br>                              365                          370                          375 | | 1156 |
| gac aaa gaa tcc act caa aag gca att gat ggg ata act aac aaa gta<br>Asp Lys Glu Ser Thr Gln Lys Ala Ile Asp Gly Ile Thr Asn Lys Val<br>                   380                          385                          390 | | 1204 |
| aat tct gtg att gaa aag atg aac act cag ttt gag gct gtt ggg aaa<br>Asn Ser Val Ile Glu Lys Met Asn Thr Gln Phe Glu Ala Val Gly Lys<br>395                              400                          405 | | 1252 |
| gaa ttc aac aat cta gag aga aga ctg gaa aac tta aat aaa aag atg<br>Glu Phe Asn Asn Leu Glu Arg Arg Leu Glu Asn Leu Asn Lys Lys Met<br>                410                          415                          420 | | 1300 |
| gaa gat ggg ttt ctt gat gta tgg aca tat aat gcc gaa ctc cta gtt<br>Glu Asp Gly Phe Leu Asp Val Trp Thr Tyr Asn Ala Glu Leu Leu Val<br>425                              430                          435                          440 | | 1348 |
| ttg atg gaa aat gag agg aca ctt gat tac cat gat tct aat gtg aag<br>Leu Met Glu Asn Glu Arg Thr Leu Asp Tyr His Asp Ser Asn Val Lys<br>                              445                          450                          455 | | 1396 |
| aat ctg tac gac aaa gtc aga atg caa ttg aga gac aat gcc aag gaa<br>Asn Leu Tyr Asp Lys Val Arg Met Gln Leu Arg Asp Asn Ala Lys Glu<br>                   460                          465                          470 | | 1444 |
| ata ggg aat gga tgc ttt gag ttt tat cat aaa tgt gat gat gaa tgc<br>Ile Gly Asn Gly Cys Phe Glu Phe Tyr His Lys Cys Asp Asp Glu Cys<br>475                              480                          485 | | 1492 |
| atg aat agt gtc agg aat ggg aca tat gat tat ccc aaa tat gaa gaa<br>Met Asn Ser Val Arg Asn Gly Thr Tyr Asp Tyr Pro Lys Tyr Glu Glu<br>              490                          495                          500 | | 1540 |
| gaa tcc aag ctg aac aga aac gaa atc aaa gga gtg aaa ttg agc aac<br>Glu Ser Lys Leu Asn Arg Asn Glu Ile Lys Gly Val Lys Leu Ser Asn<br>505                              510                          515                          520 | | 1588 |
| atg ggg gtt tat caa ata ctt gct ata tac gct aca gtg gca ggc tcc<br>Met Gly Val Tyr Gln Ile Leu Ala Ile Tyr Ala Thr Val Ala Gly Ser<br>                   525                          530                          535 | | 1636 |
| ttg tca ctg gca atc atg ata gct ggg att tct ttc tgg atg tgt tct<br>Leu Ser Leu Ala Ile Met Ile Ala Gly Ile Ser Phe Trp Met Cys Ser<br>              540                          545                          550 | | 1684 |
| aat ggg tct ctg caa tgc aga att tgc ata tga ctgtaagtca atttgtaatt<br>Asn Gly Ser Leu Gln Cys Arg Ile Cys Ile<br>              555                          560 | | 1737 |
| a | | 1738 |

<210> SEQ ID NO 6
<211> LENGTH: 562
<212> TYPE: PRT
<213> ORGANISM: Influenza A virus

<400> SEQUENCE: 6

Met Thr Ile Thr Phe Leu Ile Leu Leu Phe Thr Val Val Lys Gly Asp
1                  5                      10                     15

Gln Ile Cys Ile Gly Tyr His Ala Asn Asn Ser Thr Glu Lys Val Asp
                  20                      25                      30

Thr Ile Leu Glu Arg Asn Val Thr Val Thr His Ala Lys Asn Ile Leu
              35                          40                        45

```
Glu Lys Thr His Asn Gly Lys Leu Cys Arg Leu Ser Gly Ile Pro Pro
 50                  55                  60

Leu Glu Leu Gly Asp Cys Ser Ile Ala Gly Trp Leu Leu Gly Asn Pro
 65                  70                  75                  80

Glu Cys Asp Arg Leu Leu Ser Val Pro Glu Trp Ser Tyr Ile Val Glu
                 85                  90                  95

Lys Glu Asn Pro Ala Asn Gly Leu Cys Tyr Pro Gly Ser Phe Asn Asp
                100                 105                 110

Tyr Glu Glu Leu Lys His Leu Leu Thr Ser Val Thr His Phe Glu Lys
            115                 120                 125

Ile Lys Ile Leu Pro Arg Asp Gln Trp Thr Gln His Thr Thr Thr Gly
130                 135                 140

Gly Ser Arg Ala Cys Ala Val Ser Gly Asn Pro Ser Phe Phe Arg Asn
145                 150                 155                 160

Met Val Trp Leu Thr Lys Lys Gly Ser Asn Tyr Pro Val Ala Gln Arg
                165                 170                 175

Ser Tyr Asn Asn Thr Ser Gly Glu Gln Met Leu Ile Ile Trp Gly Ile
            180                 185                 190

His His Pro Asn Asp Asp Ala Glu Gln Arg Thr Leu Tyr Gln Asn Val
        195                 200                 205

Arg Thr Tyr Val Ser Val Gly Thr Ser Thr Leu Asn Lys Arg Ser Ile
210                 215                 220

Pro Glu Ile Ala Thr Arg Pro Lys Val Asn Gly Gln Gly Gly Arg Met
225                 230                 235                 240

Glu Phe Ser Trp Thr Leu Leu Glu Thr Trp Asp Val Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Lys Thr Leu Glu Asn Cys
        275                 280                 285

Glu Thr Lys Cys Gln Thr Pro Leu Gly Ala Ile Asn Thr Thr Leu Pro
290                 295                 300

Phe His Asn Ile His Pro Leu Thr Ile Gly Glu Cys Pro Lys Tyr Val
305                 310                 315                 320

Lys Ser Asp Arg Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Ile Asp Gly Trp Tyr Gly Tyr His Ser His
        355                 360                 365

Asp Gln Gly Ser Gly Tyr Ala Ala Asp Lys Glu Ser Thr Gln Lys Ala
370                 375                 380

Ile Asp Gly Ile Thr Asn Lys Val Asn Ser Val Ile Glu Lys Met Asn
385                 390                 395                 400

Thr Gln Phe Glu Ala Val Gly Lys Glu Phe Asn Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Tyr His Asp Ser Asn Val Lys Asn Leu Tyr Asp Lys Val Arg Met
    450                 455                 460
```

-continued

```
Gln Leu Arg Asp Asn Ala Lys Glu Ile Gly Asn Gly Cys Phe Glu Phe
465                 470                 475                 480

Tyr His Lys Cys Asp Asp Glu Cys Met Asn Ser Val Arg Asn Gly Thr
            485                 490                 495

Tyr Asp Tyr Pro Lys Tyr Glu Glu Ser Lys Leu Asn Arg Asn Glu
                500                 505                 510

Ile Lys Gly Val Lys Leu Ser Asn Met Gly Val Tyr Gln Ile Leu Ala
            515                 520                 525

Ile Tyr Ala Thr Val Ala Gly Ser Leu Ser Leu Ala Ile Met Ile Ala
            530                 535                 540

Gly Ile Ser Phe Trp Met Cys Ser Asn Gly Ser Leu Gln Cys Arg Ile
545                 550                 555                 560

Cys Ile
```

<210> SEQ ID NO 7
<211> LENGTH: 1773
<212> TYPE: DNA
<213> ORGANISM: Influenza A virus
<220> FEATURE:
<221> NAME/KEY: CDS
<222> LOCATION: (44)..(1732)

<400> SEQUENCE: 7

```
agcaaaagca ggggttatac catagacaac caaaagcaaa aca atg gcc atc att        55
                                              Met Ala Ile Ile
                                                1 tat ctc att ctc ctg ttc aca gca gtg aga ggg gac cag ata tgc att       103
Tyr Leu Ile Leu Leu Phe Thr Ala Val Arg Gly Asp Gln Ile Cys Ile
  5                  10                  15                  20 gga tac cat gcc aat aat tcc aca gag aag gtc gac aca aat cta gag       151
Gly Tyr His Ala Asn Asn Ser Thr Glu Lys Val Asp Thr Asn Leu Glu
                 25                  30                  35 cgg aac gtc act gtg act cat gcc aag gac att ctt gag aag acc cat       199
Arg Asn Val Thr Val Thr His Ala Lys Asp Ile Leu Glu Lys Thr His
             40                  45                  50 aac gga aag tta tgc aaa cta aac gga atc cct cca ctt gaa cta ggg       247
Asn Gly Lys Leu Cys Lys Leu Asn Gly Ile Pro Pro Leu Glu Leu Gly
         55                  60                  65 gac tgt agc att gcc gga tgg ctc ctt gga aat cca gaa tgt gat agg       295
Asp Cys Ser Ile Ala Gly Trp Leu Leu Gly Asn Pro Glu Cys Asp Arg
     70                  75                  80 ctt cta agt gtg cca gaa tgg tcc tat ata atg gag aaa gaa aac ccg       343
Leu Leu Ser Val Pro Glu Trp Ser Tyr Ile Met Glu Lys Glu Asn Pro
 85                  90                  95                 100 aga gac ggt ttg tgt tat cca ggc agc ttc aat gat tat gaa gaa ttg       391
Arg Asp Gly Leu Cys Tyr Pro Gly Ser Phe Asn Asp Tyr Glu Glu Leu
                105                 110                 115 aaa cat ctc ctc agc agc gtg aaa cat ttc gag aaa gta aag att ctg       439
Lys His Leu Leu Ser Ser Val Lys His Phe Glu Lys Val Lys Ile Leu
            120                 125                 130 ccc aaa gat aga tgg aca cag cat aca aca act gga ggt tca cgg gcc       487
Pro Lys Asp Arg Trp Thr Gln His Thr Thr Thr Gly Gly Ser Arg Ala
        135                 140                 145 tgc gcg gtg tct ggt aat cca tca ttt ttc agg aac atg gtc tgg ctg       535
Cys Ala Val Ser Gly Asn Pro Ser Phe Phe Arg Asn Met Val Trp Leu
    150                 155                 160 aca aag gaa gga tca gat tat ccg gtt gcc aaa gga tcg tac aac aat       583
Thr Lys Glu Gly Ser Asp Tyr Pro Val Ala Lys Gly Ser Tyr Asn Asn
165                 170                 175                 180
```

```
aca agc gga gaa caa atg cta ata att tgg ggg gtg cac cat ccc att    631
Thr Ser Gly Glu Gln Met Leu Ile Ile Trp Gly Val His His Pro Ile
                185                 190                 195 gat gag aca gaa caa aga aca ttg tac cag aat gtg gga acc tat gtt    679
Asp Glu Thr Glu Gln Arg Thr Leu Tyr Gln Asn Val Gly Thr Tyr Val
            200                 205                 210 tcc gta ggc aca tca aca ttg aac aaa agg tca acc cca gaa ata gca    727
Ser Val Gly Thr Ser Thr Leu Asn Lys Arg Ser Thr Pro Glu Ile Ala
        215                 220                 225 aca agg cct aaa gtg aat gga caa gga ggt aga atg gaa ttc tct tgg    775
Thr Arg Pro Lys Val Asn Gly Gln Gly Gly Arg Met Glu Phe Ser Trp
    230                 235                 240 acc ctc ttg gat atg tgg gac acc ata aat ttt gag agt act ggt aat    823
Thr Leu Leu Asp Met Trp Asp Thr Ile Asn Phe Glu Ser Thr Gly Asn
245                 250                 255                 260 cta att gca cca gag tat gga ttc aaa ata tcg aaa aga ggt agt tca    871
Leu Ile Ala Pro Glu Tyr Gly Phe Lys Ile Ser Lys Arg Gly Ser Ser
                265                 270                 275 ggg atc atg aaa aca gaa gga aca ctt gag aac tgt gag acc aaa tgc    919
Gly Ile Met Lys Thr Glu Gly Thr Leu Glu Asn Cys Glu Thr Lys Cys
            280                 285                 290 caa act cct ttg gga gca ata aat aca aca ttg cct ttt cac aat gtc    967
Gln Thr Pro Leu Gly Ala Ile Asn Thr Thr Leu Pro Phe His Asn Val
        295                 300                 305 cac cca ctg aca ata ggt gag tgc ccc aaa tat gta aaa tcg gag aag   1015
His Pro Leu Thr Ile Gly Glu Cys Pro Lys Tyr Val Lys Ser Glu Lys
    310                 315                 320 ttg gtc tta gca aca gga cta agg aat gtt ccc cag att gaa tca aga   1063
Leu Val Leu Ala Thr Gly Leu Arg Asn Val Pro Gln Ile Glu Ser Arg
325                 330                 335                 340 gga ttg ttt ggg gca ata gct ggt ttt ata gaa gga gga tgg caa gga   1111
Gly Leu Phe Gly Ala Ile Ala Gly Phe Ile Glu Gly Gly Trp Gln Gly
                345                 350                 355 atg gtt gat ggt tgg tat gga tac cat cac agc aat gac caa gga tca   1159
Met Val Asp Gly Trp Tyr Gly Tyr His His Ser Asn Asp Gln Gly Ser
            360                 365                 370 ggg tat gca gca gac aaa gaa tcc act caa aag gca ttt gat gga atc   1207
Gly Tyr Ala Ala Asp Lys Glu Ser Thr Gln Lys Ala Phe Asp Gly Ile
        375                 380                 385 acc aac aag gta aat tct gtg att gaa aag atg aac acc caa ttt gaa   1255
Thr Asn Lys Val Asn Ser Val Ile Glu Lys Met Asn Thr Gln Phe Glu
    390                 395                 400 gct gtt ggg aag gaa ttc ggt aac tta gag aga aga ctg gag aac ttg   1303
Ala Val Gly Lys Glu Phe Gly Asn Leu Glu Arg Arg Leu Glu Asn Leu
405                 410                 415                 420 aac aaa agg atg gaa gac ggg ttt cta gat gtg tgg aca tac aat gct   1351
Asn Lys Arg Met Glu Asp Gly Phe Leu Asp Val Trp Thr Tyr Asn Ala
                425                 430                 435 gag ctt cta gtt ctg atg gaa aat gag agg aca ctt gac ttt cat gat   1399
Glu Leu Leu Val Leu Met Glu Asn Glu Arg Thr Leu Asp Phe His Asp
            440                 445                 450 tct aat gtc aag aat ctg tat gat aaa gtc aga atg cag ctg aga gac   1447
Ser Asn Val Lys Asn Leu Tyr Asp Lys Val Arg Met Gln Leu Arg Asp
        455                 460                 465 aac gtc aaa gaa cta gga aat gga tgt ttt gaa ttt tat cac aaa tgt   1495
Asn Val Lys Glu Leu Gly Asn Gly Cys Phe Glu Phe Tyr His Lys Cys
    470                 475                 480 gat gat gaa tgc atg aat agt gtg aaa aac ggg acg tat gat tat ccc   1543
Asp Asp Glu Cys Met Asn Ser Val Lys Asn Gly Thr Tyr Asp Tyr Pro
485                 490                 495                 500
```

```
aag tat gaa gaa gag tct aaa cta aat aga aat gaa atc aaa ggg gta    1591
Lys Tyr Glu Glu Glu Ser Lys Leu Asn Arg Asn Glu Ile Lys Gly Val
            505                 510                 515 aaa ttg agc agc atg ggg gtt tat caa atc ctt gcc att tat gct aca    1639
Lys Leu Ser Ser Met Gly Val Tyr Gln Ile Leu Ala Ile Tyr Ala Thr
        520                 525                 530 gta gca ggt tct ctg tca ctg gca atc atg atg gct ggg atc tct ttc    1687
Val Ala Gly Ser Leu Ser Leu Ala Ile Met Met Ala Gly Ile Ser Phe
        535                 540                 545 tgg atg tgc tcc aac ggg tct ctg cag tgc agg atc tgc ata tga        1732
Trp Met Cys Ser Asn Gly Ser Leu Gln Cys Arg Ile Cys Ile
        550                 555                 560 ttataagtca ttttataatt aaaaacaccc ttgtttctac t                       1773
```

<210> SEQ ID NO 8
<211> LENGTH: 562
<212> TYPE: PRT
<213> ORGANISM: Influenza A virus

<400> SEQUENCE: 8

```
Met Ala Ile Ile Tyr Leu Ile Leu Leu Phe Thr Ala Val Arg Gly Asp
1               5                   10                  15

Gln Ile Cys Ile Gly Tyr His Ala Asn Asn Ser Thr Glu Lys Val Asp
            20                  25                  30

Thr Asn Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
    50                  55                  60

Leu Glu Leu Gly Asp Cys Ser Ile Ala Gly Trp Leu Leu Gly Asn Pro
65                  70                  75                  80

Glu Cys Asp Arg Leu Leu Ser Val Pro Glu Trp Ser Tyr Ile Met Glu
                85                  90                  95

Lys Glu Asn Pro Arg Asp Gly Leu Cys Tyr Pro Gly Ser Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Arg Ala Cys Ala Val Ser Gly Asn Pro Ser Phe Phe Arg Asn
145                 150                 155                 160

Met Val Trp Leu Thr Lys Glu Gly Ser Asp Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Gln Gly Gly Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
```

```
                275                 280                 285
Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Met Asn
385                 390                 395                 400

Thr Gln Phe Glu Ala Val Gly Lys Glu Phe Gly Asn Leu Glu Arg Arg
                405                 410                 415

Leu Glu Asn Leu Asn Lys Arg Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Tyr Gln Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile

<210> SEQ ID NO 9
<211> LENGTH: 1724
<212> TYPE: DNA
<213> ORGANISM: Influenza A virus
<220> FEATURE:
<221> NAME/KEY: CDS
<222> LOCATION: (9)..(1709)

<400> SEQUENCE: 9 tattaatc atg aag acc atc att gtt tta agt tat ctt ttc tgt ctg gct       50
         Met Lys Thr Ile Ile Val Leu Ser Tyr Leu Phe Cys Leu Ala
         1               5                   10 ctc agc caa gat tac tca gag aac aac aac agc act gca acg ctg tgc       98
Leu Ser Gln Asp Tyr Ser Glu Asn Asn Asn Ser Thr Ala Thr Leu Cys
15                  20                  25                  30 ttg ggg cat cat gca gta ccg aat ggg aca ata gtg aag aca att acg      146
Leu Gly His His Ala Val Pro Asn Gly Thr Ile Val Lys Thr Ile Thr
                35                  40                  45 gat gac caa att gag gtg acc aat gcc act gag ttg gtc cag agc tcc      194
```

```
Asp Asp Gln Ile Glu Val Thr Asn Ala Thr Glu Leu Val Gln Ser Ser
         50                  55                  60 tcg aca ggg aaa ata tgc aac aac cca cat aga atc ctt gat ggg agg      242
Ser Thr Gly Lys Ile Cys Asn Asn Pro His Arg Ile Leu Asp Gly Arg
             65                  70                  75 gac tgt aca ctg ata gat gcc cta ctg gga gac ccc cac tgt gat gta      290
Asp Cys Thr Leu Ile Asp Ala Leu Leu Gly Asp Pro His Cys Asp Val
         80                  85                  90 ctc caa gat gaa acc tgg gac ctt tat gtg gaa cgt agc agc gcc ttc      338
Leu Gln Asp Glu Thr Trp Asp Leu Tyr Val Glu Arg Ser Ser Ala Phe
 95                 100                 105                 110 agc aac tgc tat ccc tat gat gta cca gac tat gca tcg ctc agg tct      386
Ser Asn Cys Tyr Pro Tyr Asp Val Pro Asp Tyr Ala Ser Leu Arg Ser
                115                 120                 125 cta gtt gct tcc tca gga acc cta gag ttc atc aca gaa gga ttc aca      434
Leu Val Ala Ser Ser Gly Thr Leu Glu Phe Ile Thr Glu Gly Phe Thr
            130                 135                 140 tgg aca gga gtc act caa aat gga gga agc aat gcc tgc aaa agg ggg      482
Trp Thr Gly Val Thr Gln Asn Gly Gly Ser Asn Ala Cys Lys Arg Gly
145                 150                 155 cct gct agt ggt ttc ttc agc aga ctg aat tgg ctg act aaa tct gga      530
Pro Ala Ser Gly Phe Phe Ser Arg Leu Asn Trp Leu Thr Lys Ser Gly
        160                 165                 170 agt gct tac cca gtg ttg aat gtg act atg cca aat aat gac aac ttt      578
Ser Ala Tyr Pro Val Leu Asn Val Thr Met Pro Asn Asn Asp Asn Phe
175                 180                 185                 190 gac aaa ttg tat gtc tgg gga gtt cac cac cca agc aca aac caa gag      626
Asp Lys Leu Tyr Val Trp Gly Val His His Pro Ser Thr Asn Gln Glu
                195                 200                 205 caa acc aac cta tac gtt cag gca tca gga agg gta aca gtt tca act      674
Gln Thr Asn Leu Tyr Val Gln Ala Ser Gly Arg Val Thr Val Ser Thr
            210                 215                 220 aga agg agc caa caa acc ata atc ccg aat att gga tcc agg cct tgg      722
Arg Arg Ser Gln Gln Thr Ile Ile Pro Asn Ile Gly Ser Arg Pro Trp
                225                 230                 235 gtc agg ggc caa tca ggg agg ata agc atc tac tgg aca ata gtg aag      770
Val Arg Gly Gln Ser Gly Arg Ile Ser Ile Tyr Trp Thr Ile Val Lys
        240                 245                 250 ccg ggg gat gta cta gta att aac agt aat ggt aac ctg atc gct cct      818
Pro Gly Asp Val Leu Val Ile Asn Ser Asn Gly Asn Leu Ile Ala Pro
255                 260                 265                 270 cga ggg tac ttc aaa atg cgc act ggg aaa agc tca ata atg aga tca      866
Arg Gly Tyr Phe Lys Met Arg Thr Gly Lys Ser Ser Ile Met Arg Ser
                275                 280                 285 gat gca cct att gac aca tgc att tct gag tgt atc act cct aat gga      914
Asp Ala Pro Ile Asp Thr Cys Ile Ser Glu Cys Ile Thr Pro Asn Gly
            290                 295                 300 agc atc ccc aat gac aag cca ttt cag aat gta aac aag atc act tac      962
Ser Ile Pro Asn Asp Lys Pro Phe Gln Asn Val Asn Lys Ile Thr Tyr
                305                 310                 315 gga gca tgt cct aag tat gtc aaa cag agc act ttg aaa ctg gca aca     1010
Gly Ala Cys Pro Lys Tyr Val Lys Gln Ser Thr Leu Lys Leu Ala Thr
        320                 325                 330 ggg atg agg aac gta cct gag aaa caa acc agg ggt ctg ttc ggt gca     1058
Gly Met Arg Asn Val Pro Glu Lys Gln Thr Arg Gly Leu Phe Gly Ala
335                 340                 345                 350 ata gca gga ttt ata gaa aat gga tgg gaa gga atg ata gac ggc tgg     1106
Ile Ala Gly Phe Ile Glu Asn Gly Trp Glu Gly Met Ile Asp Gly Trp
                355                 360                 365
```

-continued

| | | | | | | | | | | | | | | | | |
|---|---|---|---|---|---|---|---|---|---|---|---|---|---|---|---|---|
| tat | ggt | ttc | aga | cac | cag | aac | tct | gag | ggt | aca | gga | caa | gct | gca | gac | 1154 |
| Tyr | Gly | Phe | Arg | His | Gln | Asn | Ser | Glu | Gly | Thr | Gly | Gln | Ala | Ala | Asp | |
| | | | 370 | | | | | 375 | | | | | 380 | | | |
| cta | aaa | agc | aca | cag | gca | gcc | att | gac | cag | att | aat | ggg | aaa | ttg | aac | 1202 |
| Leu | Lys | Ser | Thr | Gln | Ala | Ala | Ile | Asp | Gln | Ile | Asn | Gly | Lys | Leu | Asn | |
| | | 385 | | | | | 390 | | | | | 395 | | | | |
| cga | gta | atc | gag | aaa | aca | aat | gag | aag | ttt | cac | cag | att | gaa | aag | gaa | 1250 |
| Arg | Val | Ile | Glu | Lys | Thr | Asn | Glu | Lys | Phe | His | Gln | Ile | Glu | Lys | Glu | |
| | 400 | | | | | 405 | | | | | 410 | | | | | |
| ttc | tct | gaa | gta | gaa | gga | aga | atc | cag | gac | ctt | gag | aaa | tat | gtt | gaa | 1298 |
| Phe | Ser | Glu | Val | Glu | Gly | Arg | Ile | Gln | Asp | Leu | Glu | Lys | Tyr | Val | Glu | |
| 415 | | | | | 420 | | | | | 425 | | | | | 430 | |
| gac | act | aag | ata | gat | cta | tgg | tct | tac | aat | gca | gag | ctt | ctg | gtg | gcc | 1346 |
| Asp | Thr | Lys | Ile | Asp | Leu | Trp | Ser | Tyr | Asn | Ala | Glu | Leu | Leu | Val | Ala | |
| | | | | 435 | | | | | 440 | | | | | 445 | | |
| ttg | gaa | aac | cag | cat | aca | att | gat | ctg | act | gat | tct | gaa | atg | aac | aaa | 1394 |
| Leu | Glu | Asn | Gln | His | Thr | Ile | Asp | Leu | Thr | Asp | Ser | Glu | Met | Asn | Lys | |
| | | | 450 | | | | | 455 | | | | | 460 | | | |
| cta | ttc | gag | aag | acg | agg | cgg | caa | ttg | agg | gag | aat | gct | gaa | gat | atg | 1442 |
| Leu | Phe | Glu | Lys | Thr | Arg | Arg | Gln | Leu | Arg | Glu | Asn | Ala | Glu | Asp | Met | |
| | | 465 | | | | | 470 | | | | | 475 | | | | |
| ggc | aac | ggt | tgc | ttc | aaa | ata | tac | cac | aaa | tgt | gac | aac | gca | tgt | ata | 1490 |
| Gly | Asn | Gly | Cys | Phe | Lys | Ile | Tyr | His | Lys | Cys | Asp | Asn | Ala | Cys | Ile | |
| | 480 | | | | | 485 | | | | | 490 | | | | | |
| gag | tca | atc | agg | aac | ggg | acc | tat | gat | cat | gac | ata | tac | aga | gat | gaa | 1538 |
| Glu | Ser | Ile | Arg | Asn | Gly | Thr | Tyr | Asp | His | Asp | Ile | Tyr | Arg | Asp | Glu | |
| 495 | | | | | 500 | | | | | 505 | | | | | 510 | |
| gca | tta | aac | aac | cga | ttc | caa | atc | aag | ggt | gta | gag | cta | aaa | tct | ggg | 1586 |
| Ala | Leu | Asn | Asn | Arg | Phe | Gln | Ile | Lys | Gly | Val | Glu | Leu | Lys | Ser | Gly | |
| | | | | 515 | | | | | 520 | | | | | 525 | | |
| tac | aaa | gat | tgg | atc | tta | tgg | att | tcc | ttt | gcc | ata | tca | tgc | ctt | ttg | 1634 |
| Tyr | Lys | Asp | Trp | Ile | Leu | Trp | Ile | Ser | Phe | Ala | Ile | Ser | Cys | Leu | Leu | |
| | | | 530 | | | | | 535 | | | | | 540 | | | |
| ctt | tgt | gtt | gtt | cta | ctg | ggg | ttc | att | atg | tgg | gcc | tgc | caa | aga | ggc | 1682 |
| Leu | Cys | Val | Val | Leu | Leu | Gly | Phe | Ile | Met | Trp | Ala | Cys | Gln | Arg | Gly | |
| | | 545 | | | | | 550 | | | | | 555 | | | | |
| aac | att | agg | tgc | aac | att | tgc | att | tga | gtatattagt | aatta | | | | | | 1724 |
| Asn | Ile | Arg | Cys | Asn | Ile | Cys | Ile | | | | | | | | | |
| | 560 | | | | | 565 | | | | | | | | | | |

<210> SEQ ID NO 10
<211> LENGTH: 566
<212> TYPE: PRT
<213> ORGANISM: Influenza A virus

<400> SEQUENCE: 10

Met Lys Thr Ile Ile Val Leu Ser Tyr Leu Phe Cys Leu Ala Leu Ser
1               5                   10                  15

Gln Asp Tyr Ser Glu Asn Asn Ser Thr Ala Thr Leu Cys Leu Gly
            20                  25                  30

His His Ala Val Pro Asn Gly Thr Ile Val Lys Thr Ile Thr Asp Asp
        35                  40                  45

Gln Ile Glu Val Thr Asn Ala Thr Glu Leu Val Gln Ser Ser Ser Thr
    50                  55                  60

Gly Lys Ile Cys Asn Asn Pro His Arg Ile Leu Asp Gly Arg Asp Cys
65                  70                  75                  80

Thr Leu Ile Asp Ala Leu Leu Gly Asp Pro His Cys Asp Val Leu Gln
                85                  90                  95

Asp Glu Thr Trp Asp Leu Tyr Val Glu Arg Ser Ser Ala Phe Ser Asn 100                 105                 110
        Cys Tyr Pro Tyr Asp Val Pro Asp Tyr Ala Ser Leu Arg Ser Leu Val
                    115                 120                 125

Ala Ser Ser Gly Thr Leu Glu Phe Ile Thr Glu Gly Phe Thr Trp Thr
                    130                 135                 140

Gly Val Thr Gln Asn Gly Gly Ser Asn Ala Cys Lys Arg Gly Pro Ala
        145                 150                 155                 160

Ser Gly Phe Phe Ser Arg Leu Asn Trp Leu Thr Lys Ser Gly Ser Ala
                        165                 170                 175

Tyr Pro Val Leu Asn Val Thr Met Pro Asn Asn Asp Asn Phe Asp Lys
                    180                 185                 190

Leu Tyr Val Trp Gly Val His His Pro Ser Thr Asn Gln Glu Gln Thr
                    195                 200                 205

Asn Leu Tyr Val Gln Ala Ser Gly Arg Val Thr Val Ser Thr Arg Arg
                    210                 215                 220

Ser Gln Gln Thr Ile Ile Pro Asn Ile Gly Ser Arg Pro Trp Val Arg
        225                 230                 235                 240

Gly Gln Ser Gly Arg Ile Ser Ile Tyr Trp Thr Ile Val Lys Pro Gly
                        245                 250                 255

Asp Val Leu Val Ile Asn Ser Asn Gly Asn Leu Ile Ala Pro Arg Gly
                    260                 265                 270

Tyr Phe Lys Met Arg Thr Gly Lys Ser Ser Ile Met Arg Ser Asp Ala
                    275                 280                 285

Pro Ile Asp Thr Cys Ile Ser Glu Cys Ile Thr Pro Asn Gly Ser Ile
        290                 295                 300

Pro Asn Asp Lys Pro Phe Gln Asn Val Asn Lys Ile Thr Tyr Gly Ala
        305                 310                 315                 320

Cys Pro Lys Tyr Val Lys Gln Ser Thr Leu Lys Leu Ala Thr Gly Met
                        325                 330                 335

Arg Asn Val Pro Glu Lys Gln Thr Arg Gly Leu Phe Gly Ala Ile Ala
                    340                 345                 350

Gly Phe Ile Glu Asn Gly Trp Glu Gly Met Ile Asp Gly Trp Tyr Gly
                    355                 360                 365

Phe Arg His Gln Asn Ser Glu Gly Thr Gly Gln Ala Ala Asp Leu Lys
        370                 375                 380

Ser Thr Gln Ala Ala Ile Asp Gln Ile Asn Gly Lys Leu Asn Arg Val
        385                 390                 395                 400

Ile Glu Lys Thr Asn Glu Lys Phe His Gln Ile Glu Lys Glu Phe Ser
                        405                 410                 415

Glu Val Glu Gly Arg Ile Gln Asp Leu Glu Lys Tyr Val Glu Asp Thr
                    420                 425                 430

Lys Ile Asp Leu Trp Ser Tyr Asn Ala Glu Leu Leu Val Ala Leu Glu
                    435                 440                 445

Asn Gln His Thr Ile Asp Leu Thr Asp Ser Glu Met Asn Lys Leu Phe
        450                 455                 460

Glu Lys Thr Arg Arg Gln Leu Arg Glu Asn Ala Glu Asp Met Gly Asn
        465                 470                 475                 480

Gly Cys Phe Lys Ile Tyr His Lys Cys Asp Asn Ala Cys Ile Glu Ser
                        485                 490                 495

Ile Arg Asn Gly Thr Tyr Asp His Asp Ile Tyr Arg Asp Glu Ala Leu
                    500                 505                 510

Asn Asn Arg Phe Gln Ile Lys Gly Val Glu Leu Lys Ser Gly Tyr Lys
                    515                 520                 525

```
Asp Trp Ile Leu Trp Ile Ser Phe Ala Ile Ser Cys Leu Leu Cys
    530             535             540

Val Val Leu Leu Gly Phe Ile Met Trp Ala Cys Gln Arg Gly Asn Ile
545                 550             555                 560

Arg Cys Asn Ile Cys Ile
                565

<210> SEQ ID NO 11
<211> LENGTH: 1725
<212> TYPE: DNA
<213> ORGANISM: Influenza A virus
<220> FEATURE:
<221> NAME/KEY: CDS
<222> LOCATION: (7)..(1701)

<400

-continued

|  |  |  |  |  |  |  |  |  |  |  |  |  |  |  |  |  |
|--|--|--|--|--|--|--|--|--|--|--|--|--|--|--|--|--|
|  | 225 |  |  |  | 230 |  |  |  | 235 |  |  |  |  |  |  |  |

```
agt gga aga atg gaa ttt ttc tgg aca ata ctg aag tcg aac gat gca       768
Ser Gly Arg Met Glu Phe Phe Trp Thr Ile Leu Lys Ser Asn Asp Ala
    240                 245                 250 atc agc ttt gaa agt aat ggg aat ttt ata gct cct gaa tat gcg tac       816
Ile Ser Phe Glu Ser Asn Gly Asn Phe Ile Ala Pro Glu Tyr Ala Tyr
255                 260                 265                 270 aaa att gtc aag aaa gga gat tca gca atc atg aga agt gaa ttg gag       864
Lys Ile Val Lys Lys Gly Asp Ser Ala Ile Met Arg Ser Glu Leu Glu
                275                 280                 285 tat ggt aac tgt gac acc aaa tgt cag act cca ttg ggt gct ata aat       912
Tyr Gly Asn Cys Asp Thr Lys Cys Gln Thr Pro Leu Gly Ala Ile Asn
            290                 295                 300 tcc agt atg ccc ttc cac aat gtt cat cct ctt gcc att ggg gag tgc       960
Ser Ser Met Pro Phe His Asn Val His Pro Leu Ala Ile Gly Glu Cys
        305                 310                 315 ccc aag tat gtc aaa tcg gac aaa ctg gtc ctt gca aca gga cta aga      1008
Pro Lys Tyr Val Lys Ser Asp Lys Leu Val Leu Ala Thr Gly Leu Arg
    320                 325                 330 aac gta ccc caa aga aaa aca aga ggc cta ttt ggt gca ata gca gga      1056
Asn Val Pro Gln Arg Lys Thr Arg Gly Leu Phe Gly Ala Ile Ala Gly
335                 340                 345                 350 ttc ata gaa gga gga tgg caa gga atg gtt gac ggg tgg tac gga tac      1104
Phe Ile Glu Gly Gly Trp Gln Gly Met Val Asp Gly Trp Tyr Gly Tyr
                355                 360                 365 cat cat aac aat gag cag gga agt gga tat gct gca gac aaa gaa tct      1152
His His Asn Asn Glu Gln Gly Ser Gly Tyr Ala Ala Asp Lys Glu Ser
            370                 375                 380 acc cag aaa gca atc gat ggg atc acc aat aaa gta aac tca atc att      1200
Thr Gln Lys Ala Ile Asp Gly Ile Thr Asn Lys Val Asn Ser Ile Ile
        385                 390                 395 gac aaa atg aac act caa ttc gaa gcc gtt ggg aaa gaa ttc aac aac      1248
Asp Lys Met Asn Thr Gln Phe Glu Ala Val Gly Lys Glu Phe Asn Asn
    400                 405                 410 cta gaa agg aga ata gaa aat ttg aat aag aaa atg gaa gat ggg ttt      1296
Leu Glu Arg Arg Ile Glu Asn Leu Asn Lys Lys Met Glu Asp Gly Phe
415                 420                 425                 430 tta gat gta tgg act tac aat gca gaa ctt ctc gtg ctc atg gaa aac      1344
Leu Asp Val Trp Thr Tyr Asn Ala Glu Leu Leu Val Leu Met Glu Asn
                435                 440                 445 gaa aga act ctg gat ttc cat gat tca aat gtc aag aac cta tac gat      1392
Glu Arg Thr Leu Asp Phe His Asp Ser Asn Val Lys Asn Leu Tyr Asp
            450                 455                 460 aag gtc cga ctc cag ctg aga gac aat gca aaa gaa ttg ggc aac gga      1440
Lys Val Arg Leu Gln Leu Arg Asp Asn Ala Lys Glu Leu Gly Asn Gly
        465                 470                 475 tgc ttc gaa ttc tac cac aag tgt gac aat gaa tgc atg gaa agt gtg      1488
Cys Phe Glu Phe Tyr His Lys Cys Asp Asn Glu Cys Met Glu Ser Val
    480                 485                 490 aga aat gga act tat gac tat ccg caa tat tca gaa gaa tca aga ctg      1536
Arg Asn Gly Thr Tyr Asp Tyr Pro Gln Tyr Ser Glu Glu Ser Arg Leu
495                 500                 505                 510 aac aga gag gaa ata gac gga gtc aaa ttg gaa tca atg ggc acc tat      1584
Asn Arg Glu Glu Ile Asp Gly Val Lys Leu Glu Ser Met Gly Thr Tyr
                515                 520                 525 cag ata tta tca atc tac tca aca gtg gcg agt tcc cta gca ctg gca      1632
Gln Ile Leu Ser Ile Tyr Ser Thr Val Ala Ser Ser Leu Ala Leu Ala
            530                 535                 540 atc atg atg gct ggt cta tct ttt tgg atg tgt tcc aat gga tca ttg      1680
```

```
Ile Met Met Ala Gly Leu Ser Phe Trp Met Cys Ser Asn Gly Ser Leu
            545                 550                 555 cag tgc aga att tgc atc tag aattgtgagt tcagattata atta            1725
Gln Cys Arg Ile Cys Ile
    560
```

<210> SEQ ID NO 12
<211> LENGTH: 564
<212> TYPE: PRT
<213> ORGANISM: Influenza A virus

<400> SEQUENCE: 12

```
Met Glu Arg Ile Val Ile Ala Leu Ala Ile Ile Ser Ile Val Lys Gly
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Glu His Asn Gly Lys Leu Cys Ser Leu Lys Gly Val Arg
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Val Asn Gly Gln Cys Tyr Pro Gly Asp Phe Ser
            100                 105                 110

Asp Tyr Glu Glu Leu Lys His Leu Met Ser Ser Thr Asn His Phe Glu
        115                 120                 125

Lys Ile Gln Ile Ile Pro Arg Ser Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Thr Tyr Asn Asn Thr Asn Val Glu Asp Leu Leu Ile Ile Trp
            180                 185                 190

Gly Ile His His Pro Asn Asp Ala Ala Glu Gln Thr Lys Leu Tyr Gln
        195                 200                 205

Asn Ser Asn Thr Tyr Val Ser Val Gly Thr Ser Thr Leu Asn Gln Arg
    210                 215                 220

Ser Ile Pro Glu Ile Ala Thr Arg Pro Lys Val Asn Gly Gln Ser Gly
225                 230                 235                 240

Arg Met Glu Phe Phe Trp Thr Ile Leu Lys Ser Asn Asp Ala Ile Ser
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Arg Ser Glu Leu Glu Tyr Gly
        275                 280                 285

Asn Cys Asp Thr Lys Cys Gln Thr Pro Leu Gly Ala Ile Asn Ser Ser
    290                 295                 300

Met Pro Phe His Asn Val His Pro Leu Ala Ile Gly Glu Cys Pro Lys
305                 310                 315                 320

Tyr Val Lys Ser Asp Lys Leu Val Leu Ala Thr Gly Leu Arg Asn Val
                325                 330                 335

Pro Gln Arg Lys Thr Arg Gly Leu Phe Gly Ala Ile Ala Gly Phe Ile
```

```
                    340                 345                 350
Glu Gly Gly Trp Gln Gly Met Val Asp Gly Trp Tyr Gly Tyr His His
            355                 360                 365

Asn Asn Glu Gln Gly Ser Gly Tyr Ala Ala Asp Lys Glu Ser Thr Gln
        370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
    530                 535                 540

Met Ala Gly Leu Ser Phe Trp Met Cys Ser Asn Gly Ser Leu Gln Cys
545                 550                 555                 560

Arg Ile Cys Ile

<210> SEQ ID NO 13
<211> LENGTH: 1695
<212> TYPE: DNA
<213> ORGANISM: Influenza A virus
<220> FEATURE:
<221> NAME/KEY: CDS
<222> LOCATION: (6)..(1688)

<400> SEQUENCE: 13 acaaa atg aac act caa att ttg gca ctc att gct tgt atg ctg att gga       50
      Met Asn Thr Gln Ile Leu Ala Leu Ile Ala Cys Met Leu Ile Gly
      1               5                  10                  15 gct aaa gga gac aaa ata tgt ctt ggg cac cat gct gtg gca aat gga        98
Ala Lys Gly Asp Lys Ile Cys Leu Gly His His Ala Val Ala Asn Gly
                20                  25                  30 aca aaa gtg aac aca tta aca gag aga gga att gaa gta gta aat gcc      146
Thr Lys Val Asn Thr Leu Thr Glu Arg Gly Ile Glu Val Val Asn Ala
            35                  40                  45 acg gaa acg gtg gag act gta aat att aag aaa ata tgc act caa ggg      194
Thr Glu Thr Val Glu Thr Val Asn Ile Lys Lys Ile Cys Thr Gln Gly
        50                  55                  60 aaa agg cca aca gat ctg ggt caa tgt gga ctt cta gga acc cta ata      242
Lys Arg Pro Thr Asp Leu Gly Gln Cys Gly Leu Leu Gly Thr Leu Ile
65                  70                  75 gga cct ccc caa tgc gat caa ttc ctg gag ttt gac gct gac ttg ata      290
Gly Pro Pro Gln Cys Asp Gln Phe Leu Glu Phe Asp Ala Asp Leu Ile
80                  85                  90                  95 att gaa cga aga gaa gga act gat gtg tgc tac ccc ggg aag ttc aca      338
```

```
                Ile Glu Arg Arg Glu Gly Thr Asp Val Cys Tyr Pro Gly Lys Phe Thr
                                100                 105                 110 aat gaa gaa tca ctg agg cag atc ctt cga ggg tca gga gga att gat        386
Asn Glu Glu Ser Leu Arg Gln Ile Leu Arg Gly Ser Gly Gly Ile Asp
            115                 120                 125 aag gag tca atg ggt ttc acc tat agt gga ata aga acc aat ggg gta        434
Lys Glu Ser Met Gly Phe Thr Tyr Ser Gly Ile Arg Thr Asn Gly Val
        130                 135                 140 aca agt gcc tgc aga aga tca ggc tct tct ttc tat gcg gag atg aag        482
Thr Ser Ala Cys Arg Arg Ser Gly Ser Ser Phe Tyr Ala Glu Met Lys
    145                 150                 155 tgg tta ctg tcg aat tca gac aat gcg gca ttt ccc caa atg act aag        530
Trp Leu Leu Ser Asn Ser Asp Asn Ala Ala Phe Pro Gln Met Thr Lys
160                 165                 170                 175 tcg tat aga aat ccc agg aac aaa cca gct ctg ata att tgg gga gtg        578
Ser Tyr Arg Asn Pro Arg Asn Lys Pro Ala Leu Ile Ile Trp Gly Val
                180                 185                 190 cat cac tct gga tcg gct act gaa cag acc aaa ctc tat gga agt gga        626
His His Ser Gly Ser Ala Thr Glu Gln Thr Lys Leu Tyr Gly Ser Gly
            195                 200                 205 aac aag ttg ata aca gta ggg agc tcg aaa tac cag caa tca ttc acc        674
Asn Lys Leu Ile Thr Val Gly Ser Ser Lys Tyr Gln Gln Ser Phe Thr
        210                 215                 220 cca agt ccg gga gca cgg cca cag gtg aat gga caa tca gga agg att        722
Pro Ser Pro Gly Ala Arg Pro Gln Val Asn Gly Gln Ser Gly Arg Ile
    225                 230                 235 gat ttt cac tgg cta ctc ctt gat cct aat gac aca gtg acc ttc act        770
Asp Phe His Trp Leu Leu Leu Asp Pro Asn Asp Thr Val Thr Phe Thr
240                 245                 250                 255 ttc aat ggg gca ttc ata gct cct gac agg gca agt ttc ttt aga gga        818
Phe Asn Gly Ala Phe Ile Ala Pro Asp Arg Ala Ser Phe Phe Arg Gly
                260                 265                 270 gaa tcg cta gga gtc cag agt gat gtt cct ttg gat tct ggt tgt gag        866
Glu Ser Leu Gly Val Gln Ser Asp Val Pro Leu Asp Ser Gly Cys Glu
            275                 280                 285 gga gat tgc ttc cac agt ggg ggt acg ata gta agc tcc ctg cca ttc        914
Gly Asp Cys Phe His Ser Gly Gly Thr Ile Val Ser Ser Leu Pro Phe
        290                 295                 300 cag aac atc aat cct aga aca gtg ggg aaa tgc cct cga tat gtc aaa        962
Gln Asn Ile Asn Pro Arg Thr Val Gly Lys Cys Pro Arg Tyr Val Lys
    305                 310                 315 cag aca agc ctc ctt ttg gct aca gga atg aga aac gtc cca gag aac       1010
Gln Thr Ser Leu Leu Leu Ala Thr Gly Met Arg Asn Val Pro Glu Asn
320                 325                 330                 335 ccc aag acc aga ggc ctt ttt gga gca att gct gga ttc ata gag aat       1058
Pro Lys Thr Arg Gly Leu Phe Gly Ala Ile Ala Gly Phe Ile Glu Asn
                340                 345                 350 gga tgg gaa ggt ctc att gat gga tgg tat ggt ttc aga cat caa aat       1106
Gly Trp Glu Gly Leu Ile Asp Gly Trp Tyr Gly Phe Arg His Gln Asn
            355                 360                 365 gca caa gga gaa gga act gca gct gac tac aaa agc acc caa tct gca       1154
Ala Gln Gly Glu Gly Thr Ala Ala Asp Tyr Lys Ser Thr Gln Ser Ala
        370                 375                 380 ata gat cag atc aca ggc aaa ttg aat cgc cta att gac aaa aca aat       1202
Ile Asp Gln Ile Thr Gly Lys Leu Asn Arg Leu Ile Asp Lys Thr Asn
    385                 390                 395 cag cag ttt gaa ctg ata gac aat gaa ttt agt gaa ata gaa caa caa       1250
Gln Gln Phe Glu Leu Ile Asp Asn Glu Phe Ser Glu Ile Glu Gln Gln
400                 405                 410                 415
```

-continued

| | | |
|---|---|---|
| att ggg aat gtc att aac tgg aca cga gac tca atg act gag gta tgg<br>Ile Gly Asn Val Ile Asn Trp Thr Arg Asp Ser Met Thr Glu Val Trp<br>             420                              425                      430 | 1298 |
| tca tac aat gct gaa ttg ctg gta gca atg gaa aat cag cac aca ata<br>Ser Tyr Asn Ala Glu Leu Leu Val Ala Met Glu Asn Gln His Thr Ile<br>                435                             440                       445 | 1346 |
| gat ctt gca gac tca gaa atg aac aaa ctt tac gag cgt gtt agg aaa<br>Asp Leu Ala Asp Ser Glu Met Asn Lys Leu Tyr Glu Arg Val Arg Lys<br>           450                              455                     460 | 1394 |
| caa cta aga gag aat gct gaa gaa gat ggg act gga tgc ttt gag ata<br>Gln Leu Arg Glu Asn Ala Glu Glu Asp Gly Thr Gly Cys Phe Glu Ile<br>465                       470                            475 | 1442 |
| ttt cat aag tgt gat gat cag tgt atg gag agc ata agg aac aac act<br>Phe His Lys Cys Asp Asp Gln Cys Met Glu Ser Ile Arg Asn Asn Thr<br>480                     485                            490               495 | 1490 |
| tat gac cat acc caa tac aga aca gag tca ctg cag aat aga ata cag<br>Tyr Asp His Thr Gln Tyr Arg Thr Glu Ser Leu Gln Asn Arg Ile Gln<br>                    500                         505                     510 | 1538 |
| ata gac cca gtg aaa ttg agt agt gga tac aaa gac ata atc tta tgg<br>Ile Asp Pro Val Lys Leu Ser Ser Gly Tyr Lys Asp Ile Ile Leu Trp<br>           515                              520                     525 | 1586 |
| ttt agc ttc ggg gca tca tgt ttt ctt ctt cta gcc att gca atg gga<br>Phe Ser Phe Gly Ala Ser Cys Phe Leu Leu Leu Ala Ile Ala Met Gly<br>        530                            535                       540 | 1634 |
| ttg gtt ttc att tgc ata aag aat gga aac atg cgg tgc act att tgt<br>Leu Val Phe Ile Cys Ile Lys Asn Gly Asn Met Arg Cys Thr Ile Cys<br>545                     550                            555 | 1682 |
| ata tag tttgaga<br>Ile<br>560 | 1695 |

<210> SEQ ID NO 14
<211> LENGTH: 560
<212> TYPE: PRT
<213> ORGANISM: Influenza A virus

<400> SEQUENCE: 14

Met Asn Thr Gln Ile Leu Ala Leu Ile Ala Cys Met Leu Ile Gly Ala
1               5                   10                  15

Lys Gly Asp Lys Ile Cys Leu Gly His His Ala Val Ala Asn Gly Thr
            20                  25                  30

Lys Val Asn Thr Leu Thr Glu Arg Gly Ile Glu Val Val Asn Ala Thr
        35                  40                  45

Glu Thr Val Glu Thr Val Asn Ile Lys Lys Ile Cys Thr Gln Gly Lys
    50                  55                  60

Arg Pro Thr Asp Leu Gly Gln Cys Gly Leu Leu Gly Thr Leu Ile Gly
65                  70                  75                  80

Pro Pro Gln Cys Asp Gln Phe Leu Glu Phe Asp Ala Asp Leu Ile Ile
                85                  90                  95

Glu Arg Arg Glu Gly Thr Asp Val Cys Tyr Pro Gly Lys Phe Thr Asn
            100                 105                 110

Glu Glu Ser Leu Arg Gln Ile Leu Arg Gly Ser Gly Ile Asp Lys
        115                 120                 125

Glu Ser Met Gly Phe Thr Tyr Ser Gly Ile Arg Thr Asn Gly Val Thr
    130                 135                 140

Ser Ala Cys Arg Arg Ser Gly Ser Ser Phe Tyr Ala Glu Met Lys Trp
145                 150                 155                 160

Leu Leu Ser Asn Ser Asp Asn Ala Ala Phe Pro Gln Met Thr Lys Ser

```
                165                 170                 175
Tyr Arg Asn Pro Arg Asn Lys Pro Ala Leu Ile Ile Trp Gly Val His
                180                 185                 190

His Ser Gly Ser Ala Thr Glu Gln Thr Lys Leu Tyr Gly Ser Gly Asn
            195                 200                 205

Lys Leu Ile Thr Val Gly Ser Ser Lys Tyr Gln Gln Ser Phe Thr Pro
        210                 215                 220

Ser Pro Gly Ala Arg Pro Gln Val Asn Gly Gln Ser Gly Arg Ile Asp
225                 230                 235                 240

Phe His Trp Leu Leu Leu Asp Pro Asn Asp Thr Val Thr Phe Thr Phe
                245                 250                 255

Asn Gly Ala Phe Ile Ala Pro Asp Arg Ala Ser Phe Phe Arg Gly Glu
            260                 265                 270

Ser Leu Gly Val Gln Ser Asp Val Pro Leu Asp Ser Gly Cys Glu Gly
        275                 280                 285

Asp Cys Phe His Ser Gly Gly Thr Ile Val Ser Ser Leu Pro Phe Gln
    290                 295                 300

Asn Ile Asn Pro Arg Thr Val Gly Lys Cys Pro Arg Tyr Val Lys Gln
305                 310                 315                 320

Thr Ser Leu Leu Leu Ala Thr Gly Met Arg Asn Val Pro Glu Asn Pro
                325                 330                 335

Lys Thr Arg Gly Leu Phe Gly Ala Ile Ala Gly Phe Ile Glu Asn Gly
            340                 345                 350

Trp Glu Gly Leu Ile Asp Gly Trp Tyr Gly Phe Arg His Gln Asn Ala
        355                 360                 365

Gln Gly Glu Gly Thr Ala Ala Asp Tyr Lys Ser Thr Gln Ser Ala Ile
    370                 375                 380

Asp Gln Ile Thr Gly Lys Leu Asn Arg Leu Ile Asp Lys Thr Asn Gln
385                 390                 395                 400

Gln Phe Glu Leu Ile Asp Asn Glu Phe Ser Glu Ile Glu Gln Gln Ile
                405                 410                 415

Gly Asn Val Ile Asn Trp Thr Arg Asp Ser Met Thr Glu Val Trp Ser
            420                 425                 430

Tyr Asn Ala Glu Leu Leu Val Ala Met Glu Asn Gln His Thr Ile Asp
        435                 440                 445

Leu Ala Asp Ser Glu Met Asn Lys Leu Tyr Glu Arg Val Arg Lys Gln
    450                 455                 460

Leu Arg Glu Asn Ala Glu Glu Asp Gly Thr Gly Cys Phe Glu Ile Phe
465                 470                 475                 480

His Lys Cys Asp Asp Gln Cys Met Glu Ser Ile Arg Asn Asn Thr Tyr
                485                 490                 495

Asp His Thr Gln Tyr Arg Thr Glu Ser Leu Gln Asn Arg Ile Gln Ile
            500                 505                 510

Asp Pro Val Lys Leu Ser Ser Gly Tyr Lys Asp Ile Ile Leu Trp Phe
        515                 520                 525

Ser Phe Gly Ala Ser Cys Phe Leu Leu Leu Ala Ile Ala Met Gly Leu
    530                 535                 540

Val Phe Ile Cys Ile Lys Asn Gly Asn Met Arg Cys Thr Ile Cys Ile
545                 550                 555                 560

<210> SEQ ID NO 15
<211> LENGTH: 1410
<212> TYPE: DNA
<213> ORGANISM: Influenza A virus
```

```
<220> FEATURE:
<221> NAME/KEY: CDS
<222> LOCATION: (1)..(1410)

<400> SEQUENCE: 15 atg aat cca aac caa aag ata ata acc att ggt tcg gtc tgt atg aca      48
Met Asn Pro Asn Gln Lys Ile Ile Thr Ile Gly Ser Val Cys Met Thr
1               5                   10                  15 att gga atg gct aac tta ata tta caa att gga aac ata atc tca ata      96
Ile Gly Met Ala Asn Leu Ile Leu Gln Ile Gly Asn Ile Ile Ser Ile
            20                  25                  30 tgg att agc cac tca att caa ctt ggg aat caa aat cag att gaa aca     144
Trp Ile Ser His Ser Ile Gln Leu Gly Asn Gln Asn Gln Ile Glu Thr
35                  40                  45 tgc aat caa agc gtc att act tat gaa aac aac act tgg gta aat cag     192
Cys Asn Gln Ser Val Ile Thr Tyr Glu Asn Asn Thr Trp Val Asn Gln
50                  55                  60 aca tat gtt aac atc agc aac acc aac ttt gct gct gga cag tca gtg     240
Thr Tyr Val Asn Ile Ser Asn Thr Asn Phe Ala Ala Gly Gln Ser Val
65                  70                  75                  80 gtt tcc gtg aaa tta gcg ggc aat tcc tct ctc tgc cct gtt agt gga     288
Val Ser Val Lys Leu Ala Gly Asn Ser Ser Leu Cys Pro Val Ser Gly
                85                  90                  95 tgg gct ata tac agt aaa gac aac agt gta aga atc ggt tcc aag ggg     336
Trp Ala Ile Tyr Ser Lys Asp Asn Ser Val Arg Ile Gly Ser Lys Gly
            100                 105                 110 gat gtg ttt gtc ata agg gaa cca ttc ata tca tgc tcc ccc ttg gaa     384
Asp Val Phe Val Ile Arg Glu Pro Phe Ile Ser Cys Ser Pro Leu Glu
        115                 120                 125 tgc aga acc ttc ttc ttg act caa ggg gcc ttg cta aat gac aaa cat     432
Cys Arg Thr Phe Phe Leu Thr Gln Gly Ala Leu Leu Asn Asp Lys His
130                 135                 140 tcc aat gga acc att aaa gac agg agc cca tat cga acc cta atg agc     480
Ser Asn Gly Thr Ile Lys Asp Arg Ser Pro Tyr Arg Thr Leu Met Ser
145                 150                 155                 160 tgt cct att ggt gaa gtt ccc tct cca tac aac tca aga ttt gag tca     528
Cys Pro Ile Gly Glu Val Pro Ser Pro Tyr Asn Ser Arg Phe Glu Ser
                165                 170                 175 gtc gct tgg tca gca agt gct tgt cat gat ggc atc aat tgg cta aca     576
Val Ala Trp Ser Ala Ser Ala Cys His Asp Gly Ile Asn Trp Leu Thr
            180                 185                 190 att gga att tct ggc cca gac aat ggg gca gtg gct gtg tta aag tac     624
Ile Gly Ile Ser Gly Pro Asp Asn Gly Ala Val Ala Val Leu Lys Tyr
        195                 200                 205 aac ggc ata ata aca gac act atc aag agt tgg aga aac aat ata ttg     672
Asn Gly Ile Ile Thr Asp Thr Ile Lys Ser Trp Arg Asn Asn Ile Leu
210                 215                 220 aga aca caa gag tct gaa tgt gca tgt gta aat ggt tct tgc ttt act     720
Arg Thr Gln Glu Ser Glu Cys Ala Cys Val Asn Gly Ser Cys Phe Thr
225                 230                 235                 240 gta atg acc gat gga cca agt aat gga cag gcc tca tac aag atc ttc     768
Val Met Thr Asp Gly Pro Ser Asn Gly Gln Ala Ser Tyr Lys Ile Phe
                245                 250                 255 aga ata gaa aag gga aag ata gtc aaa tca gtc gaa atg aat gcc cct     816
Arg Ile Glu Lys Gly Lys Ile Val Lys Ser Val Glu Met Asn Ala Pro
            260                 265                 270 aat tat cac tat gag gaa tgc tcc tgt tat cct gat tct agt gaa atc     864
Asn Tyr His Tyr Glu Glu Cys Ser Cys Tyr Pro Asp Ser Ser Glu Ile
        275                 280                 285 aca tgt gtg tgc agg gat aac tgg cat ggc tcg aat cga ccg tgg gtg     912
```

```
                Thr Cys Val Cys Arg Asp Asn Trp His Gly Ser Asn Arg Pro Trp Val
                290                 295                 300 tct ttc aac cag aat ctg gaa tat cag ata gga tac ata tgc agt ggg         960
Ser Phe Asn Gln Asn Leu Glu Tyr Gln Ile Gly Tyr Ile Cys Ser Gly
305                 310                 315                 320 att ttc gga gac aat cca cgc cct aat gat aag aca ggc agt tgt ggt         1008
Ile Phe Gly Asp Asn Pro Arg Pro Asn Asp Lys Thr Gly Ser Cys Gly
                325                 330                 335 cca gta tcg tct aat gga gca aat gga gta aaa ggg ttt tca ttc aaa         1056
Pro Val Ser Ser Asn Gly Ala Asn Gly Val Lys Gly Phe Ser Phe Lys
            340                 345                 350 tac ggc aat ggt gtt tgg ata ggg aga act aaa agc att agt tca aga         1104
Tyr Gly Asn Gly Val Trp Ile Gly Arg Thr Lys Ser Ile Ser Ser Arg
        355                 360                 365 aac ggt ttt gag atg att tgg gat ccg aac gga tgg act ggg aca gac         1152
Asn Gly Phe Glu Met Ile Trp Asp Pro Asn Gly Trp Thr Gly Thr Asp
370                 375                 380 aat aac ttc tca ata aag caa gat atc gta gga ata aat gag tgg tca         1200
Asn Asn Phe Ser Ile Lys Gln Asp Ile Val Gly Ile Asn Glu Trp Ser
385                 390                 395                 400 gga tat agc ggg agt ttt gtt cag cat cca gaa cta aca ggg ctg gat         1248
Gly Tyr Ser Gly Ser Phe Val Gln His Pro Glu Leu Thr Gly Leu Asp
                405                 410                 415 tgt ata aga cct tgc ttc tgg gtt gaa cta atc aga ggg cga ccc aaa         1296
Cys Ile Arg Pro Cys Phe Trp Val Glu Leu Ile Arg Gly Arg Pro Lys
            420                 425                 430 gag aac aca atc tgg act agc ggg agc agc ata tcc ttt tgt ggt gta         1344
Glu Asn Thr Ile Trp Thr Ser Gly Ser Ser Ile Ser Phe Cys Gly Val
        435                 440                 445 aac agt gac act gtg ggt tgg tct tgg cca gac ggt gct gag ttg cca         1392
Asn Ser Asp Thr Val Gly Trp Ser Trp Pro Asp Gly Ala Glu Leu Pro
450                 455                 460 ttt acc att gac aag taa                                                 1410
Phe Thr Ile Asp Lys
465

<210> SEQ ID NO 16
<211> LENGTH: 469
<212> TYPE: PRT
<213> ORGANISM: Influenza A virus

<400> SEQUENCE: 16

Met Asn Pro Asn Gln Lys Ile Ile Thr Ile Gly Ser Val Cys Met Thr
1                   5                   10                  15

Ile Gly Met Ala Asn Leu Ile Leu Gln Ile Gly Asn Ile Ile Ser Ile
                20                  25                  30

Trp Ile Ser His Ser Ile Gln Leu Gly Asn Gln Asn Gln Ile Glu Thr
            35                  40                  45

Cys Asn

```
Cys Arg Thr Phe Phe Leu Thr Gln Gly Ala Leu Leu Asn Asp Lys His
        130                 135                 140
Ser Asn Gly Thr Ile Lys Asp Arg Ser Pro Tyr Arg Thr Leu Met Ser
145                 150                 155                 160
Cys Pro Ile Gly Glu Val Pro Ser Pro Tyr Asn Ser Arg Phe Glu Ser
                165                 170                 175
Val Ala Trp Ser Ala Ser Ala Cys His Asp Gly Ile Asn Trp Leu Thr
            180                 185                 190
Ile Gly Ile Ser Gly Pro Asp Asn Gly Ala Val Ala Val Leu Lys Tyr
        195                 200                 205
Asn Gly Ile Ile Thr Asp Thr Ile Lys Ser Trp Arg Asn Asn Ile Leu
210                 215                 220
Arg Thr Gln Glu Ser Glu Cys Ala Cys Val Asn Gly Ser Cys Phe Thr
225                 230                 235                 240
Val Met Thr Asp Gly Pro Ser Asn Gly Gln Ala Ser Tyr Lys Ile Phe
                245                 250                 255
Arg Ile Glu Lys Gly Lys Ile Val Lys Ser Val Glu Met Asn Ala Pro
            260                 265                 270
Asn Tyr His Tyr Glu Glu Cys Ser Cys Tyr Pro Asp Ser Ser Glu Ile
        275                 280                 285
Thr Cys Val Cys Arg Asp Asn Trp His Gly Ser Asn Arg Pro Trp Val
290                 295                 300
Ser Phe Asn Gln Asn Leu Glu Tyr Gln Ile Gly Tyr Ile Cys Ser Gly
305                 310                 315                 320
Ile Phe Gly Asp Asn Pro Arg Pro Asn Asp Lys Thr Gly Ser Cys Gly
                325                 330                 335
Pro Val Ser Ser Asn Gly Ala Asn Gly Val Lys Gly Phe Ser Phe Lys
            340                 345                 350
Tyr Gly Asn Gly Val Trp Ile Gly Arg Thr Lys Ser Ile Ser Ser Arg
        355                 360                 365
Asn Gly Phe Glu Met Ile Trp Asp Pro Asn Gly Trp Thr Gly Thr Asp
370                 375                 380
Asn Asn Phe Ser Ile Lys Gln Asp Ile Val Gly Ile Asn Glu Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Lys
            420                 425                 430
Glu Asn Thr Ile Trp Thr Ser Gly Ser Ser Ile Ser Phe Cys Gly Val
        435                 440                 445
Asn Ser Asp Thr Val Gly Trp Ser Trp Pro Asp Gly Ala Glu Leu Pro
450                 455                 460
Phe Thr Ile Asp Lys
465

<210> SEQ ID NO 17
<211> LENGTH: 1398
<212> TYPE: DNA
<213> ORGANISM: Influenza A virus
<220> FEATURE:
<221> NAME/KEY: CDS
<222> LOCATION: (21)..(1370)

<400> SEQUENCE: 17
agcaaaagca ggagttcaaa atg aat cca aat cag aag ata ata acc atc gga    53
                     Met Asn Pro Asn Gln Lys Ile Ile Thr Ile Gly
```

```
                     1               5                      10
tca atc tgt atg gta act gga ata gtt agc tta atg tta caa att ggg    101
Ser Ile Cys Met Val Thr Gly Ile Val Ser Leu Met Leu Gln Ile Gly
            15                  20                  25 aac atg atc tca ata tgg gtc agt cat tca att cac aca ggg aat caa    149
Asn Met Ile Ser Ile Trp Val Ser His Ser Ile His Thr Gly Asn Gln
        30                  35                  40 cac caa tct gaa cca atc agc aat act aat ttt ctt act gag aaa gct    197
His Gln Ser Glu Pro Ile Ser Asn Thr Asn Phe Leu Thr Glu Lys Ala
    45                  50                  55 gtg gct tca gta aaa tta gcg ggc aat tca tct ctt tgc ccc att aac    245
Val Ala Ser Val Lys Leu Ala Gly Asn Ser Ser Leu Cys Pro Ile Asn
60                  65                  70                  75 gga tgg gct gta tac agt aag gac aac agt ata agg atc ggt tcc aag    293
Gly Trp Ala Val Tyr Ser Lys Asp Asn Ser Ile Arg Ile Gly Ser Lys
            80                  85                  90 ggg gat gtg ttt gtt ata aga gag ccg ttc atc tca tgc tcc cac ttg    341
Gly Asp Val Phe Val Ile Arg Glu Pro Phe Ile Ser Cys Ser His Leu
        95                  100                 105 gaa tgc aga act ttc ttt ttg act cag gga gcc ttg ctg aat gac aag    389
Glu Cys Arg Thr Phe Phe Leu Thr Gln Gly Ala Leu Leu Asn Asp Lys
    110                 115                 120 cac tcc aat ggg act gtc aaa gac aga agc cct cac aga aca tta atg    437
His Ser Asn Gly Thr Val Lys Asp Arg Ser Pro His Arg Thr Leu Met
125                 130                 135 agt tgt cct gtg ggt gag gct ccc tcc cca tat aac tca agg ttt gag    485
Ser Cys Pro Val Gly Glu Ala Pro Ser Pro Tyr Asn Ser Arg Phe Glu
140                 145                 150                 155 tct gtt gct tgg tca gca agt gct tgc cat gat ggc acc agt tgg ttg    533
Ser Val Ala Trp Ser Ala Ser Ala Cys His Asp Gly Thr Ser Trp Leu
                160                 165                 170 acg att gga att tct ggc cca gac aat ggg gct gtg gct gta ttg aaa    581
Thr Ile Gly Ile Ser Gly Pro Asp Asn Gly Ala Val Ala Val Leu Lys
            175                 180                 185 tac aat ggc ata ata aca gac act atc aag agt tgg agg aac aac ata    629
Tyr Asn Gly Ile Ile Thr Asp Thr Ile Lys Ser Trp Arg Asn Asn Ile
        190                 195                 200 ctg aga act caa gag tct gaa tgt gca tgt gta aat ggc tct tgc ttt    677
Leu Arg Thr Gln Glu Ser Glu Cys Ala Cys Val Asn Gly Ser Cys Phe
    205                 210                 215 act gta atg act gac gga cca agt aat ggt cag gca tca cat aag atc    725
Thr Val Met Thr Asp Gly Pro Ser Asn Gly Gln Ala Ser His Lys Ile
220                 225                 230                 235 ttc aaa atg gaa aaa ggg aaa gtg gtt aaa tca gtc gaa ttg gat gct    773
Phe Lys Met Glu Lys Gly Lys Val Val Lys Ser Val Glu Leu Asp Ala
            240                 245                 250 cct aat tat cac tat gag gaa tgc tcc tgt tat cct aat gcc gga gaa    821
Pro Asn Tyr His Tyr Glu Glu Cys Ser Cys Tyr Pro Asn Ala Gly Glu
        255                 260                 265 atc aca tgt gtg tgc agg gat aat tgg cat ggc tca aat cgg cca tgg    869
Ile Thr Cys Val Cys Arg Asp Asn Trp His Gly Ser Asn Arg Pro Trp
    270                 275                 280 gta tct ttc aat caa aat ttg gag tat caa ata gga tat ata tgc agt    917
Val Ser Phe Asn Gln Asn Leu Glu Tyr Gln Ile Gly Tyr Ile Cys Ser
285                 290                 295 gga gtt ttc gga gac aat cca cgc ccc aat gat gga aca ggt agt tgt    965
Gly Val Phe Gly Asp Asn Pro Arg Pro Asn Asp Gly Thr Gly Ser Cys
300                 305                 310                 315 ggt ccg gtg tcc tct aac ggg gca tat ggg gta aaa ggg ttt tca ttt    1013
```

```
Gly Pro Val Ser Ser Asn Gly Ala Tyr Gly Val Lys Gly Phe Ser Phe
                320                 325                 330 aaa tac ggc aat ggt gtc tgg atc ggg aga acc aaa agc act aat tcc      1061
Lys Tyr Gly Asn Gly Val Trp Ile Gly Arg Thr Lys Ser Thr Asn Ser
            335                 340                 345 agg agc ggc ttt gaa atg att tgg gat cca aat ggg tgg act gaa acg      1109
Arg Ser Gly Phe Glu Met Ile Trp Asp Pro Asn Gly Trp Thr Glu Thr
        350                 355                 360 gac agt agc ttt tca gtg aaa caa gat atc gta gca ata act gat tgg      1157
Asp Ser Ser Phe Ser Val Lys Gln Asp Ile Val Ala Ile Thr Asp Trp
    365                 370                 375 tca gga tat agc ggg agt ttt gtc cag cat cca gaa ctg aca gga cta      1205
Ser Gly Tyr Ser Gly Ser Phe Val Gln His Pro Glu Leu Thr Gly Leu
380                 385                 390                 395 gat tgc ata aga cct tgt ttc tgg gtt gag ttg atc aga ggg cgg ccc      1253
Asp Cys Ile Arg Pro Cys Phe Trp Val Glu Leu Ile Arg Gly Arg Pro
                400                 405                 410 aaa gag agc aca att tgg act agt ggg agc agc ata tct ttt tgt ggt      1301
Lys Glu Ser Thr Ile Trp Thr Ser Gly Ser Ser Ile Ser Phe Cys Gly
            415                 420                 425 gta aat agt gac act gtg ggt tgg tct tgg cca gac ggt gct gag ttg      1349
Val Asn Ser Asp Thr Val Gly Trp Ser Trp Pro Asp Gly Ala Glu Leu
        430                 435                 440 cca ttc acc att gac aag tag tttgttcaaa aaactccttg tttctact          1398
Pro Phe Thr Ile Asp Lys
    445

<210> SEQ ID NO 18
<211> LENGTH: 449
<212> TYPE: PRT
<213> ORGANISM: Influenza A virus

<400> SEQUENCE: 18

Met Asn Pro Asn Gln Lys Ile Ile Thr Ile Gly Ser Ile Cys Met Val
1               5                   10                  15

Thr Gly Ile Val Ser Leu Met Leu Gln Ile Gly Asn Met Ile Ser Ile
            20                  25                  30

Trp Val Ser His Ser Ile His Thr Gly Asn Gln His Gln Ser Glu Pro
        35                  40                  45

Ile Ser Asn Thr Asn Phe Leu Thr Glu Lys Ala Val Ala Ser Val Lys
    50                  55                  60

Leu Ala Gly Asn Ser Ser Leu Cys Pro Ile Asn Gly Trp Ala Val Tyr
65                  70                  75                  80

Ser Lys Asp Asn Ser Ile Arg Ile Gly Ser Lys Gly Asp Val Phe Val
                85                  90                  95

Ile Arg Glu Pro Phe Ile Ser Cys Ser His Leu Glu Cys Arg Thr Phe
            100                 105                 110

Phe Leu Thr Gln Gly Ala Leu Leu Asn Asp Lys His Ser Asn Gly Thr
        115                 120                 125

Val Lys Asp Arg Ser Pro His Arg Thr Leu Met Ser Cys Pro Val Gly
    130                 135                 140

Glu Ala Pro Ser Pro Tyr Asn Ser Arg Phe Glu Ser Val Ala Trp Ser
145                 150                 155                 160

Ala Ser Ala Cys His Asp Gly Thr Ser Trp Leu Thr Ile Gly Ile Ser
                165                 170                 175

Gly Pro Asp Asn Gly Ala Val Ala Val Leu Lys Tyr Asn Gly Ile Ile
            180                 185                 190
```

-continued

```
Thr Asp Thr Ile Lys Ser Trp Arg Asn Asn Ile Leu Arg Thr Gln Glu
            195                 200                 205
Ser Glu Cys Ala Cys Val Asn Gly Ser Cys Phe Thr Val Met Thr Asp
        210                 215                 220
Gly Pro Ser Asn Gly Gln Ala Ser His Lys Ile Phe Lys Met Glu Lys
225                 230                 235                 240
Gly Lys Val Val Lys Ser Val Glu Leu Asp Ala Pro Asn Tyr His Tyr
                245                 250                 255
Glu Glu Cys Ser Cys Tyr Pro Asn Ala Gly Glu Ile Thr Cys Val Cys
            260                 265                 270
Arg Asp Asn Trp His Gly Ser Asn Arg Pro Trp Val Ser Phe Asn Gln
        275                 280                 285
Asn Leu Glu Tyr Gln Ile Gly Tyr Ile Cys Ser Gly Val Phe Gly Asp
290                 295                 300
Asn Pro Arg Pro Asn Asp Gly Thr Gly Ser Cys Gly Pro Val Ser Ser
305                 310                 315                 320
Asn Gly Ala Tyr Gly Val Lys Gly Phe Ser Phe Lys Tyr Gly Asn Gly
                325                 330                 335
Val Trp Ile Gly Arg Thr Lys Ser Thr Asn Ser Arg Ser Gly Phe Glu
            340                 345                 350
Met Ile Trp Asp Pro Asn Gly Trp Thr Glu Thr Asp Ser Ser Phe Ser
        355                 360                 365
Val Lys Gln Asp Ile Val Ala Ile Thr Asp Trp Ser Gly Tyr Ser Gly
    370                 375                 380
Ser Phe Val Gln His Pro Glu Leu Thr Gly Leu Asp Cys Ile Arg Pro
385                 390                 395                 400
Cys Phe Trp Val Glu Leu Ile Arg Gly Arg Pro Lys Glu Ser Thr Ile
                405                 410                 415
Trp Thr Ser Gly Ser Ser Ile Ser Phe Cys Gly Val Asn Ser Asp Thr
            420                 425                 430
Val Gly Trp Ser Trp Pro Asp Gly Ala Glu Leu Pro Phe Thr Ile Asp
        435                 440                 445
Lys
```

```
<210> SEQ ID NO 19
<211> LENGTH: 1023
<212> TYPE: DNA
<213> ORGANISM: Influenza A virus
<220> FEATURE:
<221> NAME/KEY: CDS
<222> LOCATION: (22)..(780)

<400> SEQUENCE: 19
```

```
aaagcaggta gatattgaaa g atg agt ctt cta acc gag gtc gaa acg tac        51
                        Met Ser Leu Leu Thr Glu Val Glu Thr Tyr
                         1               5                  10 gtt ctc tct atc atc ccg tca ggc ccc ctc aaa gcc gag atc gca cag        99
Val Leu Ser Ile Ile Pro Ser Gly Pro Leu Lys Ala Glu Ile Ala Gln
             15                  20                  25 aga ctt gaa gat gtc ttt gct gga aag aat acc gat ctt gag gct ctc       147
Arg Leu Glu Asp Val Phe Ala Gly Lys Asn Thr Asp Leu Glu Ala Leu
         30                  35                  40 atg gaa tgg cta aag aca aga ccg atc ctg tca cct ctg act aag ggg       195
Met Glu Trp Leu Lys Thr Arg Pro Ile Leu Ser Pro Leu Thr Lys Gly
     45                  50                  55 att tta gga ttt gtg ttc acg ctc acc gtg ccc agt gag cga gga ctg       243
Ile Leu Gly Phe Val Phe Thr Leu Thr Val Pro Ser Glu Arg Gly Leu
 60                  65                  70
```

```
            60                  65                  70
cag cgt aga cgc ttt gtc caa aat gcc ctt aat ggg aat ggg gat cca       291
Gln Arg Arg Arg Phe Val Gln Asn Ala Leu Asn Gly Asn Gly Asp Pro
 75                  80                  85                  90 aat aat atg gac aga gca gtt aaa ttg tat cga aag ctt aag agg gag       339
Asn Asn Met Asp Arg Ala Val Lys Leu Tyr Arg Lys Leu Lys Arg Glu
                 95                 100                 105 ata aca ttc cat ggg gcc aaa gaa ata gca ctc agt tat tct gct ggt       387
Ile Thr Phe His Gly Ala Lys Glu Ile Ala Leu Ser Tyr Ser Ala Gly
            110                 115                 120 gca ctt gcc agt tgt atg gga ctc ata tac aac agg atg ggg gct gta       435
Ala Leu Ala Ser Cys Met Gly Leu Ile Tyr Asn Arg Met Gly Ala Val
        125                 130                 135 acc acc gaa tca gca ttt ggc ctt ata tgc gca acc tgt gaa cag att       483
Thr Thr Glu Ser Ala Phe Gly Leu Ile Cys Ala Thr Cys Glu Gln Ile
    140                 145                 150 gcc gac tcc cag cat aag tct cat agg caa atg gta aca aca acc aat       531
Ala Asp Ser Gln His Lys Ser His Arg Gln Met Val Thr Thr Thr Asn
155                 160                 165                 170 cca tta ata aga cat gag aac aga atg gtt ctg gcc agc act aca gct       579
Pro Leu Ile Arg His Glu Asn Arg Met Val Leu Ala Ser Thr Thr Ala
                175                 180                 185 aag gct atg gag caa atg gct gga tcg agt gaa caa gca gct gag gcc       627
Lys Ala Met Glu Gln Met Ala Gly Ser Ser Glu Gln Ala Ala Glu Ala
            190                 195                 200 atg gag gtt gct agt cag gcc agg cag atg gtg cag gca atg aga gcc       675
Met Glu Val Ala Ser Gln Ala Arg Gln Met Val Gln Ala Met Arg Ala
        205                 210                 215 att ggg act cat cct agc tct agc act ggt ctg aaa aat gat ctc ctt       723
Ile Gly Thr His Pro Ser Ser Ser Thr Gly Leu Lys Asn Asp Leu Leu
    220                 225                 230 gaa aat ttg cag gcc tat cag aaa cga atg ggg gtg cag atg caa cga       771
Glu Asn Leu Gln Ala Tyr Gln Lys Arg Met Gly Val Gln Met Gln Arg
235                 240                 245                 250 ttc aag tga tcctcttgtt gttgccgcaa gtataattgg gattgtgcac              820
Phe Lys ctgatattgt ggattattga tcgccttttt tccaaaagca tttatcgtat ctttaaacac    880
ggtttaaaaa gagggccttc tacggaagga gtaccagagt ctatgaggga agaatatcga    940
gaggaacagc agaatgctgt ggatgctgac gatggtcatt ttgtcagcat agagctggag   1000
taaaaaacta ccttgtttct act                                            1023
```

<210> SEQ ID NO 20
<211> LENGTH: 252
<212> TYPE: PRT
<213> ORGANISM: Influenza A virus

<400> SEQUENCE: 20

```
Met Ser Leu Leu Thr Glu Val Glu Thr Tyr Val Leu Ser Ile Ile Pro
  1               5                  10                  15

Ser Gly Pro Leu Lys Ala Glu Ile Ala Gln Arg Leu Glu Asp Val Phe
                 20                  25                  30

Ala Gly Lys Asn Thr Asp Leu Glu Ala Leu Met Glu Trp Leu Lys Thr
             35                  40                  45

Arg Pro Ile Leu Ser Pro Leu Thr Lys Gly Ile Leu Gly Phe Val Phe
         50                  55                  60

Thr Leu Thr Val Pro Ser Glu Arg Gly Leu Gln Arg Arg Arg Phe Val
 65                  70                  75                  80
```

```
Gln Asn Ala Leu Asn Gly Asn Gly Asp Pro Asn Asn Met Asp Arg Ala
                 85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Ser Ala Phe
    130                 135                 140

Gly Leu Ile Cys Ala Thr Cys Glu Gln Ile Ala Asp Ser Gln His Lys
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Ala Ile Gly Thr His Pro Ser
    210                 215                 220

Ser Ser Thr Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250

<210> SEQ ID NO 21
<211> LENGTH: 97
<212> TYPE: PRT
<213> ORGANISM: Influenza A virus

<400> SEQUENCE: 21

Met Ser Leu Leu Thr Glu Val Glu Thr Pro Ile Arg Asn Glu Trp Gly
1               5                   10                  15

Cys Arg Cys Asn Asp Ser Ser Asp Pro Leu Val Val Ala Ala Ser Ile
            20                  25                  30

Ile Gly Ile Val His Leu Ile Leu Trp Ile Ile Asp Arg Leu Phe Ser
        35                  40                  45

Lys Ser Ile Tyr Arg Ile Phe Lys His Gly Leu Lys Arg Gly Pro Ser
    50                  55                  60

Thr Glu Gly Val Pro Glu Ser Met Arg Glu Glu Tyr Arg Glu Glu Gln
65                  70                  75                  80

Gln Asn Ala Val Asp Ala Asp Asp Gly His Phe Val Ser Ile Glu Leu
                85                  90                  95

Glu

<210> SEQ ID NO 22
<211> LENGTH: 1843
<212> TYPE: DNA
<213> ORGANISM: Influenza B virus
<220> FEATURE:
<221> NAME/KEY: CDS
<222> LOCATION: (18)..(1769)

<400> SEQUENCE: 22
tttctaatat ccacaaa atg aag gca ata att gta cta ctc atg gta gta         50
                   Met Lys Ala Ile Ile Val Leu Leu Met Val Val
                     1               5                  10 aca tcc aac gca gat cga atc tgc act ggg ata aca tct tca aac tca        98
Thr Ser Asn Ala Asp Arg Ile Cys Thr Gly Ile Thr Ser Ser Asn Ser
```

```
              15                  20                  25
cct cat gtg gtc aaa aca gct act caa ggg gaa gtt aat gtg act ggt      146
Pro His Val Val Lys Thr Ala Thr Gln Gly Glu Val Asn Val Thr Gly
         30                  35                  40 gtg ata cca ctg aca aca aca cca aca aaa tct cat ttt gca aat ctc      194
Val Ile Pro Leu Thr Thr Thr Pro Thr Lys Ser His Phe Ala Asn Leu
     45                  50                  55 aaa gga aca aag acc aga ggg aaa cta tgc cca aac tgt ctc aac tgc      242
Lys Gly Thr Lys Thr Arg Gly Lys Leu Cys Pro Asn Cys Leu Asn Cys
 60                  65                  70                  75 aca gat ctg gat gtg gcc ttg ggc aga cca atg tgt atg ggg acc ata      290
Thr Asp Leu Asp Val Ala Leu Gly Arg Pro Met Cys Met Gly Thr Ile
                 80                  85                  90 cct tcg gca aaa gct tca ata ctc cac gaa gtc aga cct gtt aca tcc      338
Pro Ser Ala Lys Ala Ser Ile Leu His Glu Val Arg Pro Val Thr Ser
             95                 100                 105 ggg tgc ttt cct ata atg cac gac aga aca aaa atc aga cag cta ccc      386
Gly Cys Phe Pro Ile Met His Asp Arg Thr Lys Ile Arg Gln Leu Pro
         110                 115                 120 aat ctt ctc aga gga tat gaa aat atc aga tta tca acc cat aac gtt      434
Asn Leu Leu Arg Gly Tyr Glu Asn Ile Arg Leu Ser Thr His Asn Val
     125                 130                 135 atc aac gca gaa agg gca cca gga gga ccc tac aga ctt gga acc tca      482
Ile Asn Ala Glu Arg Ala Pro Gly Gly Pro Tyr Arg Leu Gly Thr Ser
140                 145                 150                 155 gga tct tgc cct aac gtt acc agt aga aac gga ttc ttc gca aca atg      530
Gly Ser Cys Pro Asn Val Thr Ser Arg Asn Gly Phe Phe Ala Thr Met
                 160                 165                 170 gct tgg gct gtc cca agg gac aac aaa aca gca acg aat cca cta aca      578
Ala Trp Ala Val Pro Arg Asp Asn Lys Thr Ala Thr Asn Pro Leu Thr
             175                 180                 185 gta gaa gta cca tac att tgc aca aaa gga gaa gac caa att act gtt      626
Val Glu Val Pro Tyr Ile Cys Thr Lys Gly Glu Asp Gln Ile Thr Val
         190                 195                 200 tgg ggg ttc cat tct gat gac aaa acc caa atg aaa aac ctc tat gga      674
Trp Gly Phe His Ser Asp Asp Lys Thr Gln Met Lys Asn Leu Tyr Gly
     205                 210                 215 gac tca aat cct caa aag ttc acc tca tct gcc aat gga gta acc aca      722
Asp Ser Asn Pro Gln Lys Phe Thr Ser Ser Ala Asn Gly Val Thr Thr
220                 225                 230                 235 cat tat gtt tct cag att ggt gac ttc cca aat caa aca gaa gac gga      770
His Tyr Val Ser Gln Ile Gly Asp Phe Pro Asn Gln Thr Glu Asp Gly
                 240                 245                 250 ggg cta cca caa agc ggc aga att gtt gtt gat tac atg gtg caa aaa      818
Gly Leu Pro Gln Ser Gly Arg Ile Val Val Asp Tyr Met Val Gln Lys
             255                 260                 265 cct ggg aaa aca gga aca att gtc tat caa aga ggt gtt ttg ttg cct      866
Pro Gly Lys Thr Gly Thr Ile Val Tyr Gln Arg Gly Val Leu Leu Pro
         270                 275                 280 caa aag gtg tgg tgc gca agt ggc agg agc aag gta ata aaa ggg tcc      914
Gln Lys Val Trp Cys Ala Ser Gly Arg Ser Lys Val Ile Lys Gly Ser
     285                 290                 295 ttg cct tta att ggt gaa gca gat tgc ctt cac gaa aaa tac ggt gga      962
Leu Pro Leu Ile Gly Glu Ala Asp Cys Leu His Glu Lys Tyr Gly Gly
300                 305                 310                 315 tta aac aaa agc aag cct tac tac aca gga gaa cat gca aaa gcc ata     1010
Leu Asn Lys Ser Lys Pro Tyr Tyr Thr Gly Glu His Ala Lys Ala Ile
                 320                 325                 330 gga aat tgc cca ata tgg gtg aaa aca cct ttg aag ctt gcc aat gga     1058
```

```
                Gly Asn Cys Pro Ile Trp Val Lys Thr Pro Leu Lys Leu Ala Asn Gly
                                335                 340                 345 acc aaa tat aga cct cct gca aaa cta tta aag gaa agg ggt ttc ttc          1106
Thr Lys Tyr Arg Pro Pro Ala Lys Leu Leu Lys Glu Arg Gly Phe Phe
            350                 355                 360 gga gct att gct ggt ttc tta gag gga gga tgg gaa gga atg att gca          1154
Gly Ala Ile Ala Gly Phe Leu Glu Gly Gly Trp Glu Gly Met Ile Ala
365                 370                 375 ggt tgg cac gga tac aca tct cat gga gca cat gga gtg gca gtg gca          1202
Gly Trp His Gly Tyr Thr Ser His Gly Ala His Gly Val Ala Val Ala
380                 385                 390                 395 gca gac ctt aag agc acg caa gaa gcc ata aac aag ata aca aaa aat          1250
Ala Asp Leu Lys Ser Thr Gln Glu Ala Ile Asn Lys Ile Thr Lys Asn
                400                 405                 410 ctc aat tct ttg agt gag cta gaa gta aag aat ctt caa aga cta agt          1298
Leu Asn Ser Leu Ser Glu Leu Glu Val Lys Asn Leu Gln Arg Leu Ser
            415                 420                 425 ggt gcc atg gat gaa ctc cac aac gaa ata ctc gag ctg gat gag aaa          1346
Gly Ala Met Asp Glu Leu His Asn Glu Ile Leu Glu Leu Asp Glu Lys
        430                 435                 440 gtg gat gat ctc aga gct gac aca ata agc tcg caa ata gag ctt gca          1394
Val Asp Asp Leu Arg Ala Asp Thr Ile Ser Ser Gln Ile Glu Leu Ala
445                 450                 455 gtc ttg ctt tcc aac gaa gga ata ata aac agt gaa gat gag cat cta          1442
Val Leu Leu Ser Asn Glu Gly Ile Ile Asn Ser Glu Asp Glu His Leu
460                 465                 470                 475 ttg gca ctt gag aga aaa cta aag aaa atg ctg ggt ccc tct gct gta          1490
Leu Ala Leu Glu Arg Lys Leu Lys Lys Met Leu Gly Pro Ser Ala Val
                480                 485                 490 gac ata ggg aat gga tgc ttc gaa acc aaa cac aag tgc aac cag acc          1538
Asp Ile Gly Asn Gly Cys Phe Glu Thr Lys His Lys Cys Asn Gln Thr
            495                 500                 505 tgc cta gac agg ata gct gct ggc acc ttt aat gca gga gaa ttt tct          1586
Cys Leu Asp Arg Ile Ala Ala Gly Thr Phe Asn Ala Gly Glu Phe Ser
        510                 515                 520 ctt ccc act ttt gat tca ctg aat att act gct gca tct tta aat gat          1634
Leu Pro Thr Phe Asp Ser Leu Asn Ile Thr Ala Ala Ser Leu Asn Asp
525                 530                 535 gat gga ttg gat aat cat act ata ctg ctc tac tac tca act gct gct          1682
Asp Gly Leu Asp Asn His Thr Ile Leu Leu Tyr Tyr Ser Thr Ala Ala
540                 545                 550                 555 tct agt ttg gcc gta aca ttg atg ata gct att ttt att gtt tat atg          1730
Ser Ser Leu Ala Val Thr Leu Met Ile Ala Ile Phe Ile Val Tyr Met
                560                 565                 570 gtc tcc aga gac aat gtt tct tgc tcc atc tgt cta taa ggaaaattaa          1779
Val Ser Arg Asp Asn Val Ser Cys Ser Ile Cys Leu
            575                 580 gccctgtatt ttcctttatt gtagtgcttg tttgcttgtt accattacaa agaaacgtta       1839
ttga                                                                     1843

<210> SEQ ID NO 23
<211> LENGTH: 583
<212> TYPE: PRT
<213> ORGANISM: Influenza B virus

<400> SEQUENCE: 23

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
```

```
                    20                  25                  30
Thr Ala Thr Gln Gly Glu Val Asn Val Thr Gly Val Ile Pro Leu Thr
                35                  40                  45
Thr Thr Pro Thr Lys Ser His Phe Ala Asn Leu Lys Gly Thr Lys Thr
 50                  55                  60
Arg Gly Lys Leu Cys Pro Asn Cys Leu Asn Cys Thr Asp Leu Asp Val
 65                  70                  75                  80
Ala Leu Gly Arg Pro Met Cys Met Gly Thr Ile Pro Ser Ala Lys Ala
                85                  90                  95
Ser Ile Leu His Glu Val Arg Pro Val Thr Ser Gly Cys Phe Pro Ile
                100                 105                 110
Met His Asp Arg Thr Lys Ile Arg Gln Leu Pro Asn Leu Leu Arg Gly
                115                 120                 125
Tyr Glu Asn Ile Arg Leu Ser Thr His Asn Val Ile Asn Ala Glu Arg
                130                 135                 140
Ala Pro Gly Gly Pro Tyr Arg Leu Gly Thr Ser Gly Ser Cys Pro Asn
145                 150                 155                 160
Val Thr Ser Arg Asn Gly Phe Phe Ala Thr Met Ala Trp Ala Val Pro
                165                 170                 175
Arg Asp Asn Lys Thr Ala Thr Asn Pro Leu Thr Val Glu Val Pro Tyr
                180                 185                 190
Ile Cys Thr Lys Gly Glu Asp Gln Ile Thr Val Trp Gly Phe His Ser
                195                 200                 205
Asp Asp Lys Thr Gln Met Lys Asn Leu Tyr Gly Asp Ser Asn Pro Gln
                210                 215                 220
Lys Phe Thr Ser Ser Ala Asn Gly Val Thr Thr His Tyr Val Ser Gln
225                 230                 235                 240
Ile Gly Asp Phe Pro Asn Gln Thr Glu Asp Gly Gly Leu Pro Gln Ser
                245                 250                 255
Gly Arg Ile Val Val Asp Tyr Met Val Gln Lys Pro Gly Lys Thr Gly
                260                 265                 270
Thr Ile Val Tyr Gln Arg Gly Val Leu Leu Pro Gln Lys Val Trp Cys
                275                 280                 285
Ala Ser Gly Arg Ser Lys Val Ile Lys Gly Ser Leu Pro Leu Ile Gly
                290                 295                 300
Glu Ala Asp Cys Leu His Glu Lys Tyr Gly Gly Leu Asn Lys Ser Lys
305                 310                 315                 320
Pro Tyr Tyr Thr Gly Glu His Ala Lys Ala Ile Gly Asn Cys Pro Ile
                325                 330                 335
Trp Val Lys Thr Pro Leu Lys Leu Ala Asn Gly Thr Lys Tyr Arg Pro
                340                 345                 350
Pro Ala Lys Leu Leu Lys Glu Arg Gly Phe Phe Gly Ala Ile Ala Gly
                355                 360                 365
Phe Leu Glu Gly Gly Trp Glu Gly Met Ile Ala Gly Trp His Gly Tyr
                370                 375                 380
Thr Ser His Gly Ala His Gly Val Ala Val Ala Ala Asp Leu Lys Ser
385                 390                 395                 400
Thr Gln Glu Ala Ile Asn Lys Ile Thr Lys Asn Leu Asn Ser Leu Ser
                405                 410                 415
Glu Leu Glu Val Lys Asn Leu Gln Arg Leu Ser Gly Ala Met Asp Glu
                420                 425                 430
Leu His Asn Glu Ile Leu Glu Leu Asp Glu Lys Val Asp Asp Leu Arg
                435                 440                 445
```

```
Ala Asp Thr Ile Ser Ser Gln Ile Glu Leu Ala Val Leu Leu Ser Asn
    450                 455                 460
Glu Gly Ile Ile Asn Ser Glu Asp Glu His Leu Ala Leu Glu Arg
465                 470                 475                 480
Lys Leu Lys Lys Met Leu Gly Pro Ser Ala Val Asp Ile Gly Asn Gly
                485                 490                 495
Cys Phe Glu Thr Lys His Lys Cys Asn Gln Thr Cys Leu Asp Arg Ile
                500                 505                 510
Ala Ala Gly Thr Phe Asn Ala Gly Glu Phe Ser Leu Pro Thr Phe Asp
                515                 520                 525
Ser Leu Asn Ile Thr Ala Ala Ser Leu Asn Asp Asp Gly Leu Asp Asn
    530                 535                 540
His Thr Ile Leu Leu Tyr Tyr Ser Thr Ala Ala Ser Ser Leu Ala Val
545                 550                 555                 560
Thr Leu Met Ile Ala Ile Phe Ile Val Tyr Met Val Ser Arg Asp Asn
                565                 570                 575
Val Ser Cys Ser Ile Cys Leu
                580

<210> SEQ ID NO 24
<211> LENGTH: 1847
<212> TYPE: DNA
<213> ORGANISM: Influenza B virus
<220> FEATURE:
<221> NAME/KEY: CDS
<222> LOCATION: (16)..(1773)

<400> SEQUENCE: 24
tctaatatcc acaaa atg aag gca ata att gta cta ctc atg gta gta aca         51
                Met Lys Ala Ile Ile Val Leu Leu Met Val Val Thr
                 1               5                  10 tcc aat gca gat cga atc tgc act ggg ata aca tcg tca aac tca cca         99
Ser Asn Ala Asp Arg Ile Cys Thr Gly Ile Thr Ser Ser Asn Ser Pro
         15                  20                  25 cat gtt gtc aaa act gct act caa ggg gag gtc aat gtg act ggt gta       147
His Val Val Lys Thr Ala Thr Gln Gly Glu Val Asn Val Thr Gly Val
 30                  35                  40 ata cca ctg aca aca aca ccc acc aaa tct cat ttt gca aat ctc aaa       195
Ile Pro Leu Thr Thr Thr Pro Thr Lys Ser His Phe Ala Asn Leu Lys
45                  50                  55                  60 gga aca gaa acc aga ggg aaa cta tgc cca aaa tgc ctc aac tgc aca       243
Gly Thr Glu Thr Arg Gly Lys Leu Cys Pro Lys Cys Leu Asn Cys Thr
                 65                  70                  75 gat ctg gac gtg gcc ttg ggc aga cca aaa tgc acg ggg aac ata ccc       291
Asp Leu Asp Val Ala Leu Gly Arg Pro Lys Cys Thr Gly Asn Ile Pro
             80                  85                  90 tcg gca aga gtt tca ata ctc cat gaa gtc aga cct gtt aca tct ggg       339
Ser Ala Arg Val Ser Ile Leu His Glu Val Arg Pro Val Thr Ser Gly
         95                  100                 105 tgc ttt cct ata atg cac gac aga aca aag att aga cag ctg cct aac       387
Cys Phe Pro Ile Met His Asp Arg Thr Lys Ile Arg Gln Leu Pro Asn
     110                 115                 120 ctt ctc aga gga tac gaa cat atc agg tta tca act cat aac gtt atc       435
Leu Leu Arg Gly Tyr Glu His Ile Arg Leu Ser Thr His Asn Val Ile
125                 130                 135                 140 aat gca gaa aat gca cca gga gga ccc tac aaa att gga acc tca ggg       483
Asn Ala Glu Asn Ala Pro Gly Gly Pro Tyr Lys Ile Gly Thr Ser Gly
                 145                 150                 155
```

| | | | | | | | | | | | | | | | | |
|---|---|---|---|---|---|---|---|---|---|---|---|---|---|---|---|---|
| tct | tgc | cct | aac | gtt | acc | aat | gga | aac | gga | ttt | ttc | gca | aca | atg | gct | 531 |
| Ser | Cys | Pro | Asn | Val | Thr | Asn | Gly | Asn | Gly | Phe | Phe | Ala | Thr | Met | Ala | |
| | | | 160 | | | | | 165 | | | | | 170 | | | |
| tgg | gcc | gtc | cca | aaa | aac | gac | aac | aac | aaa | aca | gca | aca | aat | tca | tta | 579 |
| Trp | Ala | Val | Pro | Lys | Asn | Asp | Asn | Asn | Lys | Thr | Ala | Thr | Asn | Ser | Leu | |
| | | 175 | | | | | 180 | | | | | 185 | | | | |
| aca | ata | gaa | gta | cca | tac | att | tgt | aca | gaa | gga | gaa | gac | caa | att | acc | 627 |
| Thr | Ile | Glu | Val | Pro | Tyr | Ile | Cys | Thr | Glu | Gly | Glu | Asp | Gln | Ile | Thr | |
| | 190 | | | | | 195 | | | | | 200 | | | | | |
| gtt | tgg | ggg | ttc | cac | tct | gat | aac | gag | acc | caa | atg | gca | aag | ctc | tat | 675 |
| Val | Trp | Gly | Phe | His | Ser | Asp | Asn | Glu | Thr | Gln | Met | Ala | Lys | Leu | Tyr | |
| 205 | | | | | 210 | | | | | 215 | | | | | 220 | |
| ggg | gac | tca | aag | ccc | cag | aag | ttc | acc | tca | tct | gcc | aac | gga | gtg | acc | 723 |
| Gly | Asp | Ser | Lys | Pro | Gln | Lys | Phe | Thr | Ser | Ser | Ala | Asn | Gly | Val | Thr | |
| | | | 225 | | | | | 230 | | | | | 235 | | | |
| aca | cat | tac | gtt | tca | cag | att | ggt | ggc | ttc | cca | aat | caa | aca | gaa | gac | 771 |
| Thr | His | Tyr | Val | Ser | Gln | Ile | Gly | Gly | Phe | Pro | Asn | Gln | Thr | Glu | Asp | |
| | | | 240 | | | | | 245 | | | | | 250 | | | |
| gga | gga | cta | cca | caa | agt | ggt | aga | att | gtt | gtt | gat | tac | atg | gtg | caa | 819 |
| Gly | Gly | Leu | Pro | Gln | Ser | Gly | Arg | Ile | Val | Val | Asp | Tyr | Met | Val | Gln | |
| | | | 255 | | | | | 260 | | | | | 265 | | | |
| aaa | tct | ggg | aaa | aca | gga | aca | att | acc | tat | caa | aga | ggt | att | tta | ttg | 867 |
| Lys | Ser | Gly | Lys | Thr | Gly | Thr | Ile | Thr | Tyr | Gln | Arg | Gly | Ile | Leu | Leu | |
| | 270 | | | | | 275 | | | | | 280 | | | | | |
| cct | caa | aag | gtg | tgg | tgc | gca | agt | ggc | agg | agc | aag | gta | ata | aaa | gga | 915 |
| Pro | Gln | Lys | Val | Trp | Cys | Ala | Ser | Gly | Arg | Ser | Lys | Val | Ile | Lys | Gly | |
| 285 | | | | | 290 | | | | | 295 | | | | | 300 | |
| tcc | ttg | cct | tta | att | gga | gaa | gca | gat | tgc | ctc | cac | gaa | aaa | tac | ggt | 963 |
| Ser | Leu | Pro | Leu | Ile | Gly | Glu | Ala | Asp | Cys | Leu | His | Glu | Lys | Tyr | Gly | |
| | | | | 305 | | | | | 310 | | | | | 315 | | |
| gga | tta | aac | aaa | agc | aag | cct | tac | tac | aca | ggg | gaa | cat | gca | aag | gcc | 1011 |
| Gly | Leu | Asn | Lys | Ser | Lys | Pro | Tyr | Tyr | Thr | Gly | Glu | His | Ala | Lys | Ala | |
| | | | 320 | | | | | 325 | | | | | 330 | | | |
| ata | gga | aat | tgc | cca | ata | tgg | gtg | aaa | aca | ccc | ttg | aag | ctg | gcc | aat | 1059 |
| Ile | Gly | Asn | Cys | Pro | Ile | Trp | Val | Lys | Thr | Pro | Leu | Lys | Leu | Ala | Asn | |
| | | 335 | | | | | 340 | | | | | 345 | | | | |
| gga | acc | aaa | tat | aga | cct | cct | gca | aaa | cta | tta | aag | gaa | agg | ggt | ttc | 1107 |
| Gly | Thr | Lys | Tyr | Arg | Pro | Pro | Ala | Lys | Leu | Leu | Lys | Glu | Arg | Gly | Phe | |
| | 350 | | | | | 355 | | | | | 360 | | | | | |
| ttc | gga | gct | att | gct | ggt | ttc | tta | gaa | gga | gga | tgg | gaa | gga | atg | att | 1155 |
| Phe | Gly | Ala | Ile | Ala | Gly | Phe | Leu | Glu | Gly | Gly | Trp | Glu | Gly | Met | Ile | |
| 365 | | | | | 370 | | | | | 375 | | | | | 380 | |
| gca | ggt | tgg | cac | gga | tac | aca | tcc | cat | ggg | gca | cat | gga | gta | gcg | gtg | 1203 |
| Ala | Gly | Trp | His | Gly | Tyr | Thr | Ser | His | Gly | Ala | His | Gly | Val | Ala | Val | |
| | | | | 385 | | | | | 390 | | | | | 395 | | |
| gca | gca | gac | ctt | aag | agc | act | caa | gag | gcc | ata | aac | aag | ata | aca | aaa | 1251 |
| Ala | Ala | Asp | Leu | Lys | Ser | Thr | Gln | Glu | Ala | Ile | Asn | Lys | Ile | Thr | Lys | |
| | | | 400 | | | | | 405 | | | | | 410 | | | |
| aat | ctc | aac | tct | ttg | agt | gag | ctg | gaa | gta | aag | aat | ctt | caa | aga | cta | 1299 |
| Asn | Leu | Asn | Ser | Leu | Ser | Glu | Leu | Glu | Val | Lys | Asn | Leu | Gln | Arg | Leu | |
| | | 415 | | | | | 420 | | | | | 425 | | | | |
| agc | ggt | gcc | atg | gat | gaa | ctc | cac | aac | gaa | ata | cta | gaa | cta | gac | gag | 1347 |
| Ser | Gly | Ala | Met | Asp | Glu | Leu | His | Asn | Glu | Ile | Leu | Glu | Leu | Asp | Glu | |
| | 430 | | | | | 435 | | | | | 440 | | | | | |
| aaa | gtg | gat | gat | ctc | aga | gct | gat | aca | ata | agc | tca | caa | ata | gaa | ctc | 1395 |
| Lys | Val | Asp | Asp | Leu | Arg | Ala | Asp | Thr | Ile | Ser | Ser | Gln | Ile | Glu | Leu | |
| 445 | | | | | 450 | | | | | 455 | | | | | 460 | |
| gca | gtc | ctg | ctt | tcc | aat | gaa | gga | ata | ata | aac | agt | gaa | gat | gag | cat | 1443 |
| Ala | Val | Leu | Leu | Ser | Asn | Glu | Gly | Ile | Ile | Asn | Ser | Glu | Asp | Glu | His | |
| | | | | 465 | | | | | 470 | | | | | 475 | | |

```
ctc ttg gcg ctt gaa aga aag ctg aag aaa atg ctg ggc ccc tct gct      1491
Leu Leu Ala Leu Glu Arg Lys Leu Lys Lys Met Leu Gly Pro Ser Ala
            480                 485                 490 gta gag ata ggg aat gga tgc ttt gaa acc aaa cac aag tgc aac cag      1539
Val Glu Ile Gly Asn Gly Cys Phe Glu Thr Lys His Lys Cys Asn Gln
            495                 500                 505 acc tgt ctc gac aga ata gct gct ggt acc ttt gat gca gga gaa ttt      1587
Thr Cys Leu Asp Arg Ile Ala Ala Gly Thr Phe Asp Ala Gly Glu Phe
510                 515                 520 tct ctc ccc acc ttt gat tca ctg aat att act gct gca tct tta aat      1635
Ser Leu Pro Thr Phe Asp Ser Leu Asn Ile Thr Ala Ala Ser Leu Asn
525                 530                 535                 540 gac gat gga ttg gat aat cat act ata ctg ctt tat tac tca act gct      1683
Asp Asp Gly Leu Asp Asn His Thr Ile Leu Leu Tyr Tyr Ser Thr Ala
            545                 550                 555 gcc tcc agt ttg gct gta aca ttg atg ata gct atc ttt gtt gtt tat      1731
Ala Ser Ser Leu Ala Val Thr Leu Met Ile Ala Ile Phe Val Val Tyr
            560                 565                 570 atg gtc tcc aga gac aat gtt tct tgc tcc atc tgt cta taa              1773
Met Val Ser Arg Asp Asn Val Ser Cys Ser Ile Cys Leu
            575                 580             585 gggaagttaa accctgtatt ttcctttatt gtagtgcttg tttgcttgtt accattacaa    1833
agaaacgtta ttga                                                      1847

<210> SEQ ID NO 25
<211> LENGTH: 585
<212> TYPE: PRT
<213> ORGANISM: Influenza B virus

<400> SEQUENCE: 25

Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
            20                  25                  30

Thr Ala Thr Gln Gly Glu Val Asn Val Thr Gly Val Ile Pro Leu Thr
        35                  40                  45

Thr Thr Pro Thr Lys Ser His Phe Ala Asn Leu Lys Gly Thr Glu Thr
    50                  55                  60

Arg Gly Lys Leu Cys Pro Lys Cys Leu Asn Cys Thr Asp Leu Asp Val
65                  70                  75                  80

Ala Leu Gly Arg Pro Lys Cys Thr Gly Asn Ile Pro Ser Ala Arg Val
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu His Ile Arg Leu Ser Thr His Asn Val Ile Asn Ala Glu Asn
    130                 135                 140

Ala Pro Gly Gly Pro Tyr Lys Ile Gly Thr Ser Gly Ser Cys Pro Asn
145                 150                 155                 160

Val Thr Asn Gly Asn Gly Phe Phe Ala Thr Met Ala Trp Ala Val Pro
                165                 170                 175

Lys Asn Asp Asn Asn Lys Thr Ala Thr Asn Ser Leu Thr Ile Glu Val
            180                 185                 190

Pro Tyr Ile Cys Thr Glu Gly Glu Asp Gln Ile Thr Val Trp Gly Phe
        195                 200                 205
```

```
His Ser Asp Asn Glu Thr Gln Met Ala Lys Leu Tyr Gly Asp Ser Lys
        210                 215                 220

Pro Gln Lys Phe Thr Ser Ser Ala Asn Gly Val Thr Thr His Tyr Val
225                 230                 235                 240

Ser Gln Ile Gly Gly Phe Pro Asn Gln Thr Glu Asp Gly Gly Leu Pro
                245                 250                 255

Gln Ser Gly Arg Ile Val Val Asp Tyr Met Val Gln Lys Ser Gly Lys
                260                 265                 270

Thr Gly Thr Ile Thr Tyr Gln Arg Gly Ile Leu Leu Pro Gln Lys Val
            275                 280                 285

Trp Cys Ala Ser Gly Arg Ser Lys Val Ile Lys Gly Ser Leu Pro Leu
        290                 295                 300

Ile Gly Glu Ala Asp Cys Leu His Glu Lys Tyr Gly Gly Leu Asn Lys
305                 310                 315                 320

Ser Lys Pro Tyr Tyr Thr Gly Glu His Ala Lys Ala Ile Gly Asn Cys
                325                 330                 335

Pro Ile Trp Val Lys Thr Pro Leu Lys Leu Ala Asn Gly Thr Lys Tyr
                340                 345                 350

Arg Pro Pro Ala Lys Leu Leu Lys Glu Arg Gly Phe Phe Gly Ala Ile
            355                 360                 365

Ala Gly Phe Leu Glu Gly Gly Trp Glu Gly Met Ile Ala Gly Trp His
        370                 375                 380

Gly Tyr Thr Ser His Gly Ala His Gly Val Ala Val Ala Ala Asp Leu
385                 390                 395                 400

Lys Ser Thr Gln Glu Ala Ile Asn Lys Ile Thr Lys Asn Leu Asn Ser
                405                 410                 415

Leu Ser Glu Leu Glu Val Lys Asn Leu Gln Arg Leu Ser Gly Ala Met
            420                 425                 430

Asp Glu Leu His Asn Glu Ile Leu Glu Leu Asp Glu Lys Val Asp Asp
        435                 440                 445

Leu Arg Ala Asp Thr Ile Ser Ser Gln Ile Glu Leu Ala Val Leu Leu
450                 455                 460

Ser Asn Glu Gly Ile Ile Asn Ser Glu Asp Glu His Leu Leu Ala Leu
465                 470                 475                 480

Glu Arg Lys Leu Lys Lys Met Leu Gly Pro Ser Ala Val Glu Ile Gly
                485                 490                 495

Asn Gly Cys Phe Glu Thr Lys His Lys Cys Asn Gln Thr Cys Leu Asp
            500                 505                 510

Arg Ile Ala Ala Gly Thr Phe Asp Ala Gly Glu Phe Ser Leu Pro Thr
        515                 520                 525

Phe Asp Ser Leu Asn Ile Thr Ala Ala Ser Leu Asn Asp Asp Gly Leu
530                 535                 540

Asp Asn His Thr Ile Leu Leu Tyr Tyr Ser Thr Ala Ala Ser Ser Leu
545                 550                 555                 560

Ala Val Thr Leu Met Ile Ala Ile Phe Val Val Tyr Met Val Ser Arg
                565                 570                 575

Asp Asn Val Ser Cys Ser Ile Cys Leu
            580                 585

<210> SEQ ID NO 26
<211> LENGTH: 1755
<212> TYPE: DNA
<213> ORGANISM: Influenza B virus
<220> FEATURE:
```

```
<221> NAME/KEY: CDS
<222> LOCATION: (1)..(1755)

<400> SEQUENCE: 26 atg aag gca ata att gta cta ctc atg gta gta aca tcc aat gca gat      48
Met Lys Ala Ile Ile Val Leu Leu Met Val Val Thr Ser Asn Ala Asp
1               5                   10                  15 cga atc tgc act ggg ata aca tct tca aac tca cct cat gtg gtc aaa      96
Arg Ile Cys Thr Gly Ile Thr Ser Ser Asn Ser Pro His Val Val Lys
            20                  25                  30 aca gct act caa ggg gag gtc aat gtg act ggc gtg ata cca ctg aca     144
Thr Ala Thr Gln Gly Glu Val Asn Val Thr Gly Val Ile Pro Leu Thr
        35                  40                  45 aca aca cca aca aaa tct tat ttt gca aat ctc aaa gga aca agg acc     192
Thr Thr Pro Thr Lys Ser Tyr Phe Ala Asn Leu Lys Gly Thr Arg Thr
    50                  55                  60 aga ggg aaa cta tgc ccg gac tgt ctc aac tgt aca gat ctg gat gtg     240
Arg Gly Lys Leu Cys Pro Asp Cys Leu Asn Cys Thr Asp Leu Asp Val
65                  70                  75                  80 gcc ttg ggc agg cca atg tgt gtg ggg acc aca ccc tct gct aaa gct     288
Ala Leu Gly Arg Pro Met Cys Val Gly Thr Thr Pro Ser Ala Lys Ala
                85                  90                  95 tca ata ctc cat gag gtc aga cct gtt aca tcc ggg tgc ttt cct ata     336
Ser Ile Leu His Glu Val Arg Pro Val Thr Ser Gly Cys Phe Pro Ile
            100                 105                 110 atg cac gac aga aca aaa atc agg caa cta ccc aat ctt ctc aga gga     384
Met His Asp Arg Thr Lys Ile Arg Gln Leu Pro Asn Leu Leu Arg Gly
        115                 120                 125 tat gaa aag atc agg tta tca acc caa aac gtt atc gat gca gaa aaa     432
Tyr Glu Lys Ile Arg Leu Ser Thr Gln Asn Val Ile Asp Ala Glu Lys
    130                 135                 140 gca cca gga gga ccc tac aga ctt gga acc tca gga tct tgc cct aac     480
Ala Pro Gly Gly Pro Tyr Arg Leu Gly Thr Ser Gly Ser Cys Pro Asn
145                 150                 155                 160 gct acc agt aaa atc gga ttt ttt gca aca atg gct tgg gct gtc cca     528
Ala Thr Ser Lys Ile Gly Phe Phe Ala Thr Met Ala Trp Ala Val Pro
                165                 170                 175 aag gac aac tac aaa aat gca acg aac cca caa aca gtg gaa gta cca     576
Lys Asp Asn Tyr Lys Asn Ala Thr Asn Pro Gln Thr Val Glu Val Pro
            180                 185                 190 tac att tgt aca gaa ggg gaa gac caa att act gtt tgg ggg ttc cat     624
Tyr Ile Cys Thr Glu Gly Glu Asp Gln Ile Thr Val Trp Gly Phe His
        195                 200                 205 tcg gat aac aaa acc caa atg aag agc ctc tat gga gac tca aat cct     672
Ser Asp Asn Lys Thr Gln Met Lys Ser Leu Tyr Gly Asp Ser Asn Pro
    210                 215                 220 caa aag ttc acc tca tct gct aat gga gta acc aca cat tat gtt tct     720
Gln Lys Phe Thr Ser Ser Ala Asn Gly Val Thr Thr His Tyr Val Ser
225                 230                 235                 240 cag att ggc gac ttc cca gat caa aca gaa gac gga gga cta cca caa     768
Gln Ile Gly Asp Phe Pro Asp Gln Thr Glu Asp Gly Gly Leu Pro Gln
                245                 250                 255 agc ggc aga att gtt gtt gat tac atg atg caa aaa cct ggg aaa aca     816
Ser Gly Arg Ile Val Val Asp Tyr Met Met Gln Lys Pro Gly Lys Thr
            260                 265                 270 gga aca att gtc tat caa agg ggt gtt ttg ttg cct caa aag gtg tgg     864
Gly Thr Ile Val Tyr Gln Arg Gly Val Leu Leu Pro Gln Lys Val Trp
        275                 280                 285 tgc gcg agt ggc agg agc aaa gta ata aaa ggg tca ttg cct tta att     912
Cys Ala Ser Gly Arg Ser Lys Val Ile Lys Gly Ser Leu Pro Leu Ile
    290                 295                 300
```

```
                        290                 295                 300
ggt gaa gca gat tgc ctt cat gaa gaa tac ggt gga tta aac aaa agc        960
Gly Glu Ala Asp Cys Leu His Glu Glu Tyr Gly Gly Leu Asn Lys Ser
305                 310                 315                 320 aag cct tac tac aca gga aaa cat gca aaa gcc ata gga aat tgc cca       1008
Lys Pro Tyr Tyr Thr Gly Lys His Ala Lys Ala Ile Gly Asn Cys Pro
                325                 330                 335 ata tgg gta aaa aca cct ttg aag ctt gcc aat gga acc aaa tat aga       1056
Ile Trp Val Lys Thr Pro Leu Lys Leu Ala Asn Gly Thr Lys Tyr Arg
            340                 345                 350 cct cct gca aaa cta ttg aag gaa agg ggt ttc ttc gga gct att gct       1104
Pro Pro Ala Lys Leu Leu Lys Glu Arg Gly Phe Phe Gly Ala Ile Ala
                    355                 360                 365 ggt ttc cta gaa gga gga tgg gaa gga atg att gca ggt tgg cac gga       1152
Gly Phe Leu Glu Gly Gly Trp Glu Gly Met Ile Ala Gly Trp His Gly
370                 375                 380 tac aca tct cac gga gca cat gga gtg gca gtg gcg gca gac ctt aag       1200
Tyr Thr Ser His Gly Ala His Gly Val Ala Val Ala Ala Asp Leu Lys
385                 390                 395                 400 agt aca caa gaa gct ata aat aag ata aca aaa aat ctc aat tct ttg       1248
Ser Thr Gln Glu Ala Ile Asn Lys Ile Thr Lys Asn Leu Asn Ser Leu
                405                 410                 415 agt gaa cta gaa gta aag aac ctt caa aga cta agt ggt gcc atg gat       1296
Ser Glu Leu Glu Val Lys Asn Leu Gln Arg Leu Ser Gly Ala Met Asp
            420                 425                 430 gaa ctc cac aac gaa ata ctc gag ctg gat gaa aaa gtg gat gat ctc       1344
Glu Leu His Asn Glu Ile Leu Glu Leu Asp Glu Lys Val Asp Asp Leu
                435                 440                 445 aga gct gac act ata agc tca caa ata gaa ctt gca gtc ttg ctt tcc       1392
Arg Ala Asp Thr Ile Ser Ser Gln Ile Glu Leu Ala Val Leu Leu Ser
450                 455                 460 aac gaa gga ata ata aac agt gaa gac gag cat cta ttg gca ctt gag       1440
Asn Glu Gly Ile Ile Asn Ser Glu Asp Glu His Leu Leu Ala Leu Glu
465                 470                 475                 480 aga aaa cta aag aaa atg ctg ggt ccc tct gct gta gac ata gga aac       1488
Arg Lys Leu Lys Lys Met Leu Gly Pro Ser Ala Val Asp Ile Gly Asn
                485                 490                 495 gga tgc ttc gaa acc aaa cac aaa tgc aac cag acc tgc tta gac agg       1536
Gly Cys Phe Glu Thr Lys His Lys Cys Asn Gln Thr Cys Leu Asp Arg
            500                 505                 510 ata gct gct ggc acc ttt aat gca gga gaa ttt tct ctc ccc act ttt       1584
Ile Ala Ala Gly Thr Phe Asn Ala Gly Glu Phe Ser Leu Pro Thr Phe
                    515                 520                 525 gat tca ttg aac att act gct gca tct tta aat gat gat gga ttg gat       1632
Asp Ser Leu Asn Ile Thr Ala Ala Ser Leu Asn Asp Asp Gly Leu Asp
530                 535                 540 aac cat act ata ctg ctc tat tac tca act gct gct tct agt ttg gct       1680
Asn His Thr Ile Leu Leu Tyr Tyr Ser Thr Ala Ala Ser Ser Leu Ala
545                 550                 555                 560 gta aca tta atg cta gct att ttt att gtt tat atg gtc tcc aga gac       1728
Val Thr Leu Met Leu Ala Ile Phe Ile Val Tyr Met Val Ser Arg Asp
                565                 570                 575 aac gtt tca tgc tcc atc tgt cta taa                                   1755
Asn Val Ser Cys Ser Ile Cys Leu
            580

<210> SEQ ID NO 27
<211> LENGTH: 584
<212> TYPE: PRT
<213> ORGANISM: Influenza B virus
```

<400> SEQUENCE: 27

```
Met Lys Ala Ile Ile Val Leu Leu Met Val Val Thr Ser Asn Ala Asp
1               5                   10                  15

Arg Ile Cys Thr Gly Ile Thr Ser Ser Asn Ser Pro His Val Val Lys
                20                  25                  30

Thr Ala Thr Gln Gly Glu Val Asn Val Thr Gly Val Ile Pro Leu Thr
            35                  40                  45

Thr Thr Pro Thr Lys Ser Tyr Phe Ala Asn Leu Lys Gly Thr Arg Thr
        50                  55                  60

Arg Gly Lys Leu Cys Pro Asp Cys Leu Asn Cys Thr Asp Leu Asp Val
65                  70                  75                  80

Ala Leu Gly Arg Pro Met Cys Val Gly Thr Thr Pro Ser Ala Lys Ala
                85                  90                  95

Ser Ile Leu His Glu Val Arg Pro Val Thr Ser Gly Cys Phe Pro Ile
            100                 105                 110

Met His Asp Arg Thr Lys Ile Arg Gln Leu Pro Asn Leu Leu Arg Gly
        115                 120                 125

Tyr Glu Lys Ile Arg Leu Ser Thr Gln Asn Val Ile Asp Ala Glu Lys
    130                 135                 140

Ala Pro Gly Gly Pro Tyr Arg Leu Gly Thr Ser Gly Ser Cys Pro Asn
145                 150                 155                 160

Ala Thr Ser Lys Ile Gly Phe Phe Ala Thr Met Ala Trp Ala Val Pro
                165                 170                 175

Lys Asp Asn Tyr Lys Asn Ala Thr Asn Pro Gln Thr Val Glu Val Pro
            180                 185                 190

Tyr Ile Cys Thr Glu Gly Glu Asp Gln Ile Thr Val Trp Gly Phe His
        195                 200                 205

Ser Asp Asn Lys Thr Gln Met Lys Ser Leu Tyr Gly Asp Ser Asn Pro
210                 215                 220

Gln Lys Phe Thr Ser Ser Ala Asn Gly Val Thr Thr His Tyr Val Ser
225                 230                 235                 240

Gln Ile Gly Asp Phe Pro Asp Gln Thr Glu Asp Gly Gly Leu Pro Gln
                245                 250                 255

Ser Gly Arg Ile Val Val Asp Tyr Met Met Gln Lys Pro Gly Lys Thr
            260                 265                 270

Gly Thr Ile Val Tyr Gln Arg Gly Val Leu Leu Pro Gln Lys Val Trp
        275                 280                 285

Cys Ala Ser Gly Arg Ser Lys Val Ile Lys Gly Ser Leu Pro Leu Ile
290                 295                 300

Gly Glu Ala Asp Cys Leu His Glu Tyr Gly Gly Leu Asn Lys Ser
305                 310                 315                 320

Lys Pro Tyr Tyr Thr Gly Lys His Ala Lys Ala Ile Gly Asn Cys Pro
                325                 330                 335

Ile Trp Val Lys Thr Pro Leu Lys Leu Ala Asn Gly Thr Lys Tyr Arg
            340                 345                 350

Pro Pro Ala Lys Leu Leu Lys Glu Arg Gly Phe Phe Gly Ala Ile Ala
        355                 360                 365

Gly Phe Leu Glu Gly Gly Trp Glu Gly Met Ile Ala Gly Trp His Gly
    370                 375                 380

Tyr Thr Ser His Gly Ala His Gly Val Ala Val Ala Ala Asp Leu Lys
385                 390                 395                 400

Ser Thr Gln Glu Ala Ile Asn Lys Ile Thr Lys Asn Leu Asn Ser Leu
```

```
                    405                 410                 415
Ser Glu Leu Glu Val Lys Asn Leu Gln Arg Leu Ser Gly Ala Met Asp
            420                 425                 430

Glu Leu His Asn Glu Ile Leu Glu Leu Asp Glu Lys Val Asp Asp Leu
        435                 440                 445

Arg Ala Asp Thr Ile Ser Ser Gln Ile Glu Leu Ala Val Leu Leu Ser
    450                 455                 460

Asn Glu Gly Ile Ile Asn Ser Glu Asp Glu His Leu Leu Ala Leu Glu
465                 470                 475                 480

Arg Lys Leu Lys Lys Met Leu Gly Pro Ser Ala Val Asp Ile Gly Asn
                485                 490                 495

Gly Cys Phe Glu Thr Lys His Lys Cys Asn Gln Thr Cys Leu Asp Arg
            500                 505                 510

Ile Ala Ala Gly Thr Phe Asn Ala Gly Glu Phe Ser Leu Pro Thr Phe
        515                 520                 525

Asp Ser Leu Asn Ile Thr Ala Ala Ser Leu Asn Asp Asp Gly Leu Asp
    530                 535                 540

Asn His Thr Ile Leu Leu Tyr Tyr Ser Thr Ala Ala Ser Ser Leu Ala
545                 550                 555                 560

Val Thr Leu Met Leu Ala Ile Phe Ile Val Tyr Met Val Ser Arg Asp
                565                 570                 575

Asn Val Ser Cys Ser Ile Cys Leu
            580

<210> SEQ ID NO 28
<211> LENGTH: 1408
<212> TYPE: DNA
<213> ORGANISM: Influenza B virus
<220> FEATURE:
<221> NAME/KEY: CDS
<222> LOCATION: (8)..(1408)

<400> SEQUENCE: 28 atgaaca atg cta cct tca act ata caa acg tta acc cta ttt ctc aca        49
        Met Leu Pro Ser Thr Ile Gln Thr Leu Thr Leu Phe Leu Thr
        1               5                   10 tca ggg gga gtg tta tta tca cta tat gtg tca gcc tta ctg tca tac       97
Ser Gly Gly Val Leu Leu Ser Leu Tyr Val Ser Ala Leu Leu Ser Tyr
15              20                  25                  30 tta ctg tat tcg gat ata ttg cta aaa ttt tca cca aca aaa ata att       145
Leu Leu Tyr Ser Asp Ile Leu Leu Lys Phe Ser Pro Thr Lys Ile Ile
                35                  40                  45 gca cca aca atg tca ttg gac tgc gcg aac gca tca aat gtt cag gct       193
Ala Pro Thr Met Ser Leu Asp Cys Ala Asn Ala Ser Asn Val Gln Ala
            50                  55                  60 gcg aac cat tct gca aca aaa gag atg aca ttt ctt ctc cca gaa ccg       241
Ala Asn His Ser Ala Thr Lys Glu Met Thr Phe Leu Leu Pro Glu Pro
        65                  70                  75 gaa tgg aca tac cct cgt tta tct tgc cag ggc tca acc ttt cag aaa       289
Glu Trp Thr Tyr Pro Arg Leu Ser Cys Gln Gly Ser Thr Phe Gln Lys
    80                  85                  90 gca ctc cta att agc cct cat aga ttc gga gaa gcc aaa gga aac tca       337
Ala Leu Leu Ile Ser Pro His Arg Phe Gly Glu Ala Lys Gly Asn Ser
95                  100                 105                 110 gct ccc ttg ata ata agg gaa cct ttt att gct tgt gga cca aag gag       385
Ala Pro Leu Ile Ile Arg Glu Pro Phe Ile Ala Cys Gly Pro Lys Glu
                115                 120                 125 tgc aaa cac ttt gct cta acc cat tat gca gct caa cca ggg gga tac       433
```

```
            Cys Lys His Phe Ala Leu Thr His Tyr Ala Ala Gln Pro Gly Gly Tyr
                        130                 135                 140 tac aat gga aca aga gag gac aga aac aag ctg agg cat ctg att tca        481
Tyr Asn Gly Thr Arg Glu Asp Arg Asn Lys Leu Arg His Leu Ile Ser
            145                 150                 155 gtc aac tta ggc aaa atc cca act gta gaa aac tcc att ttc cac atg        529
Val Asn Leu Gly Lys Ile Pro Thr Val Glu Asn Ser Ile Phe His Met
    160                 165                 170 gca gct tgg agt gga tcc gca tgc cat gat ggt aga gaa tgg aca tat        577
Ala Ala Trp Ser Gly Ser Ala Cys His Asp Gly Arg Glu Trp Thr Tyr
175                 180                 185                 190 atc gga gtt gat ggc cct gac agt aat gca ttg atc aaa ata aaa tat        625
Ile Gly Val Asp Gly Pro Asp Ser Asn Ala Leu Ile Lys Ile Lys Tyr
                195                 200                 205 gga gaa gca tac act gac aca tac cat tcc tat gca aac aac atc cta        673
Gly Glu Ala Tyr Thr Asp Thr Tyr His Ser Tyr Ala Asn Asn Ile Leu
            210                 215                 220 aga aca caa gaa agt gcc tgc aat tgc atc ggg gga gat tgt tat ctt        721
Arg Thr Gln Glu Ser Ala Cys Asn Cys Ile Gly Gly Asp Cys Tyr Leu
        225                 230                 235 atg ata act gat ggc tca gct tca gga att agt aaa tgc aga ttt ctt        769
Met Ile Thr Asp Gly Ser Ala Ser Gly Ile Ser Lys Cys Arg Phe Leu
    240                 245                 250 aag att cga gag ggt cga ata ata aaa gaa ata ttt cca aca gga aga        817
Lys Ile Arg Glu Gly Arg Ile Ile Lys Glu Ile Phe Pro Thr Gly Arg
255                 260                 265                 270 gta gag cat act gaa gaa tgc aca tgc gga ttt gcc agc aat aaa acc        865
Val Glu His Thr Glu Glu Cys Thr Cys Gly Phe Ala Ser Asn Lys Thr
                275                 280                 285 ata gaa tgt gcc tgt aga gat aac agt tac aca gca aaa aga ccc ttt        913
Ile Glu Cys Ala Cys Arg Asp Asn Ser Tyr Thr Ala Lys Arg Pro Phe
            290                 295                 300 gtc aaa tta aat gtg gag act gat aca gct gaa ata aga ttg atg tgc        961
Val Lys Leu Asn Val Glu Thr Asp Thr Ala Glu Ile Arg Leu Met Cys
        305                 310                 315 aca gag act tat ttg gac acc ccc aga cca gat gat gga agc ata aca        1009
Thr Glu Thr Tyr Leu Asp Thr Pro Arg Pro Asp Asp Gly Ser Ile Thr
    320                 325                 330 ggg cct tgc gaa tct aat ggg gaa aaa ggg cgt gga ggt atc aag gga        1057
Gly Pro Cys Glu Ser Asn Gly Glu Lys Gly Arg Gly Gly Ile Lys Gly
335                 340                 345                 350 gga ttt gtc cat caa aga atg gca tcc aag att gga aga tgg tac tcc        1105
Gly Phe Val His Gln Arg Met Ala Ser Lys Ile Gly Arg Trp Tyr Ser
                355                 360                 365 cga acg atg tct aaa act gaa aga atg ggg atg gaa ctg tat gtc aag        1153
Arg Thr Met Ser Lys Thr Glu Arg Met Gly Met Glu Leu Tyr Val Lys
            370                 375                 380 tat gat gga gac cca tgg act gac agt gac gcc ctt gct cct agt gga        1201
Tyr Asp Gly Asp Pro Trp Thr Asp Ser Asp Ala Leu Ala Pro Ser Gly
        385                 390                 395 gta atg gtc tca atg aaa gaa cct ggt tgg tat tct ttc ggc ttc gaa        1249
Val Met Val Ser Met Lys Glu Pro Gly Trp Tyr Ser Phe Gly Phe Glu
    400                 405                 410 ata aaa gat aag aaa tgt gat gtc ccc tgt att ggg ata gag atg gta        1297
Ile Lys Asp Lys Lys Cys Asp Val Pro Cys Ile Gly Ile Glu Met Val
415                 420                 425                 430 cac gat ggt gga aaa aag act tgg cac tca gca gca aca gcc att tac        1345
His Asp Gly Gly Lys Lys Thr Trp His Ser Ala Ala Thr Ala Ile Tyr
                435                 440                 445
```

```
tgt tta atg ggc tca gga cag ttg cta tgg gac act gtc aca ggt gtt    1393
Cys Leu Met Gly Ser Gly Gln Leu Leu Trp Asp Thr Val Thr Gly Val
            450                 455                 460 gat atg gct ttg taa                                                1408
Asp Met Ala Leu
        465
```

<210> SEQ ID NO 29
<211> LENGTH: 466
<212> TYPE: PRT
<213> ORGANISM: Influenza B virus

<400> SEQUENCE: 29

```
Met Leu Pro Ser Thr Ile Gln Thr Leu Thr Leu Phe Leu Thr Ser Gly
1               5                   10                  15

Gly Val Leu Leu Ser Leu Tyr Val Ser Ala Leu Leu Ser Tyr Leu Leu
            20                  25                  30

Tyr Ser Asp Ile Leu Leu Lys Phe Ser Pro Thr Lys Ile Ile Ala Pro
        35                  40                  45

Thr Met Ser Leu Asp Cys Ala Asn Ala Ser Asn Val Gln Ala Ala Asn
    50                  55                  60

His Ser Ala Thr Lys Glu Met Thr Phe Leu Leu Pro Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Ala Lys Gly Asn Ser Ala Pro
            100                 105                 110

Leu Ile Ile Arg Glu Pro Phe Ile Ala Cys Gly Pro Lys Glu Cys Lys
        115                 120                 125

His Phe Ala Leu Thr His Tyr Ala Ala Gln Pro Gly Gly Tyr Tyr Asn
    130                 135                 140

Gly Thr Arg Glu Asp Arg Asn Lys Leu Arg His Leu Ile Ser Val Asn
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Ser Asn Ala Leu Ile Lys Ile Lys Tyr Gly Glu
        195                 200                 205

Ala Tyr Thr Asp Thr Tyr His Ser Tyr Ala Asn Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Phe Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Glu
305                 310                 315                 320

Thr Tyr Leu Asp Thr Pro Arg Pro Asp Asp Gly Ser Ile Thr Gly Pro
                325                 330                 335
```

```
Cys Glu Ser Asn Gly Glu Lys Gly Arg Gly Ile Lys Gly Gly Phe
            340                 345                 350

Val His Gln Arg Met Ala Ser Lys Ile Gly Arg Trp Tyr Ser Arg Thr
        355                 360                 365

Met Ser Lys Thr Glu Arg Met Gly Met Glu Leu Tyr Val Lys Tyr Asp
    370                 375                 380

Gly Asp Pro Trp Thr Asp Ser Asp Ala Leu Ala Pro Ser Gly Val Met
385                 390                 395                 400

Val Ser Met Lys Glu Pro Gly Trp Tyr Ser Phe Gly Phe Glu Ile Lys
                405                 410                 415

Asp Lys Lys Cys Asp Val Pro Cys Ile Gly Ile Glu Met Val His Asp
            420                 425                 430

Gly Gly Lys Lys Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
    450                 455                 460

Ala Leu
465

<210> SEQ ID NO 30
<211> LENGTH: 1557
<212> TYPE: DNA
<213> ORGANISM: Influenza B virus
<220> FEATURE:
<221> NAME/KEY: CDS
<222> LOCATION: (54)..(1454)

<400> SEQUENCE: 30
agcagaagca gagcatattc ttagaactga agtgaacagg ccaaaaatga aca atg         56
                                                            Met
                                                            1 cta cct tca act gta caa aca tta acc cta tta ctc aca tca ggg gga      104
Leu Pro Ser Thr Val Gln Thr Leu Thr Leu Leu Leu Thr Ser Gly Gly
            5                   10                  15 gta tta tta tca cta tat gtg tca gcc tca ttg tca tac tta ttg tat      152
Val Leu Leu Ser Leu Tyr Val Ser Ala Ser Leu Ser Tyr Leu Leu Tyr
        20                  25                  30 tcg gat gta ttg cta aaa ttt tca tca aca aaa aca act gca cca aca      200
Ser Asp Val Leu Leu Lys Phe Ser Ser Thr Lys Thr Thr Ala Pro Thr
    35                  40                  45 atg tca tta gag tgc aca aac gca tca aat gcc cag act gtg aac cat      248
Met Ser Leu Glu Cys Thr Asn Ala Ser Asn Ala Gln Thr Val Asn His
50                  55                  60                  65 tct gca aca aaa gag atg aca ttt cca ccc cca gag ccg gag tgg aca      296
Ser Ala Thr Lys Glu Met Thr Phe Pro Pro Pro Glu Pro Glu Trp Thr
                70                  75                  80 tac cct cgt tta tct tgc cag ggc tca acc ttt cag aag gca ctc cta      344
Tyr Pro Arg Leu Ser Cys Gln Gly Ser Thr Phe Gln Lys Ala Leu Leu
            85                  90                  95 att agc cct cat agg ttc gga gag atc aaa gga aac tca gct ccc ttg      392
Ile Ser Pro His Arg Phe Gly Glu Ile Lys Gly Asn Ser Ala Pro Leu
        100                 105                 110 ata ata aga gaa cct ttt gtt gct tgt gga cca aaa gaa tgc aga cac      440
Ile Ile Arg Glu Pro Phe Val Ala Cys Gly Pro Lys Glu Cys Arg His
    115                 120                 125 ttt gct ctg acc cat tat gca gct cag ccg ggg gga tac tac aat gga      488
Phe Ala Leu Thr His Tyr Ala Ala Gln Pro Gly Gly Tyr Tyr Asn Gly
130                 135                 140                 145 aca aga aag gac aga aac aag ctg agg cat cta gta tca gtc aaa ttg      536
```

-continued

```
                Thr Arg Lys Asp Arg Asn Lys Leu Arg His Leu Val Ser Val Lys Leu
                            150                 155                 160 gga aaa atc cca act gtg gaa aac tcc att ttc cac atg gca gct tgg         584
Gly Lys Ile Pro Thr Val Glu Asn Ser Ile Phe His Met Ala Ala Trp
            165                 170                 175 agc gga tcc gca tgc cat gat ggt aga gaa tgg aca tat atc gga gtt         632
Ser Gly Ser Ala Cys His Asp Gly Arg Glu Trp Thr Tyr Ile Gly Val
            180                 185                 190 gat ggt cct gac aat gat gca ttg gtc aaa ata aaa tat gga gaa gca         680
Asp Gly Pro Asp Asn Asp Ala Leu Val Lys Ile Lys Tyr Gly Glu Ala
    195                 200                 205 tat act gac aca tat cat tcc tat gca cac aac atc cta aga aca caa         728
Tyr Thr Asp Thr Tyr His Ser Tyr Ala His Asn Ile Leu Arg Thr Gln
210                 215                 220                 225 gaa agt gcc tgc aat tgc atc ggg gga gat tgt tat ctt atg ata aca         776
Glu Ser Ala Cys Asn Cys Ile Gly Gly Asp Cys Tyr Leu Met Ile Thr
                230                 235                 240 gac ggc tca gct tca gga att agt aaa tgc aga ttt ctt aaa att aga         824
Asp Gly Ser Ala Ser Gly Ile Ser Lys Cys Arg Phe Leu Lys Ile Arg
            245                 250                 255 gag ggt cga ata ata aaa gaa ata ctt cca aca gga aga gtg gag cac         872
Glu Gly Arg Ile Ile Lys Glu Ile Leu Pro Thr Gly Arg Val Glu His
        260                 265                 270 act gaa gag tgc aca tgc ggg ttc gcc agc aat aaa acc ata gaa tgt         920
Thr Glu Glu Cys Thr Cys Gly Phe Ala Ser Asn Lys Thr Ile Glu Cys
    275                 280                 285 gcc tgt aga gac aac agt tac aca gca aaa aga ccc ttt gtc aaa tta         968
Ala Cys Arg Asp Asn Ser Tyr Thr Ala Lys Arg Pro Phe Val Lys Leu
290                 295                 300                 305 aat gtg gaa act gat aca gct gaa ata aga ttg atg tgc aca aag act        1016
Asn Val Glu Thr Asp Thr Ala Glu Ile Arg Leu Met Cys Thr Lys Thr
                310                 315                 320 tat cta gac act ccc aga ccg gat gat gga agc ata gca ggg cct tgc        1064
Tyr Leu Asp Thr Pro Arg Pro Asp Asp Gly Ser Ile Ala Gly Pro Cys
            325                 330                 335 gaa tct aat gga gac aag tgg ctt gga ggc atc aaa gga gga ttc gtc        1112
Glu Ser Asn Gly Asp Lys Trp Leu Gly Gly Ile Lys Gly Gly Phe Val
        340                 345                 350 cat caa aga atg gca tct aag att gga aga tgg tac tcc cga acg atg        1160
His Gln Arg Met Ala Ser Lys Ile Gly Arg Trp Tyr Ser Arg Thr Met
    355                 360                 365 tct aaa act aac aga atg ggg atg gaa ctg tat gta aag tat gat ggt        1208
Ser Lys Thr Asn Arg Met Gly Met Glu Leu Tyr Val Lys Tyr Asp Gly
370                 375                 380                 385 gac cca tgg act gac agt gat gct ctt act ctt agt gga gta atg gtt        1256
Asp Pro Trp Thr Asp Ser Asp Ala Leu Thr Leu Ser Gly Val Met Val
                390                 395                 400 tcc ata gaa gaa cct ggt tgg tat tct ttt ggc ttc gaa ata aag gac        1304
Ser Ile Glu Glu Pro Gly Trp Tyr Ser Phe Gly Phe Glu Ile Lys Asp
            405                 410                 415 aag aaa tgt gat gtc cct tgt att ggg ata gag atg gta cac gat ggt        1352
Lys Lys Cys Asp Val Pro Cys Ile Gly Ile Glu Met Val His Asp Gly
        420                 425                 430 gga aaa gat act tgg cat tca gct gca aca gcc att tac tgt ttg atg        1400
Gly Lys Asp Thr Trp His Ser Ala Ala Thr Ala Ile Tyr Cys Leu Met
    435                 440                 445 ggc tca gga caa ttg cta tgg gac act gtc aca ggt gtt gat atg gct        1448
Gly Ser Gly Gln Leu Leu Trp Asp Thr Val Thr Gly Val Asp Met Ala
450                 455                 460                 465
```

```
tta taa tagaggaatg gttggatctg ttctaaaccc tttgttccta ttttatttga      1504
Leu acagttgttc ttactagatt taattgtttc tgaaaaatgc tcttgttact act         1557
```

<210> SEQ ID NO 31
<211> LENGTH: 466
<212> TYPE: PRT
<213> ORGANISM: Influenza B virus

<400> SEQUENCE: 31

```
Met Leu Pro Ser Thr Val Gln Thr Leu Thr Leu Leu Leu Thr Ser Gly
1               5                   10                  15

Gly Val Leu Leu Ser Leu Tyr Val Ser Ala Ser Leu Ser Tyr Leu Leu
            20                  25                  30

Tyr Ser Asp Val Leu Leu Lys Phe Ser Ser Thr Lys Thr Thr Ala Pro
        35                  40                  45

Thr Met Ser Leu Glu Cys Thr Asn Ala Ser Asn Ala Gln Thr Val Asn
    50                  55                  60

His Ser Ala Thr Lys Glu Met Thr Phe Pro Pro Glu Pro Glu Trp
65                  70                  75                  80

Thr Tyr Pro Arg Leu Ser Cys Gln Gly Ser Thr Phe Gln Lys Ala Leu
                85                  90                  95

Leu Ile Ser Pro His Arg Phe Gly Glu Ile Lys Gly Asn Ser Ala Pro
            100                 105                 110

Leu Ile Ile Arg Glu Pro Phe Val Ala Cys Gly Pro Lys Glu Cys Arg
        115                 120                 125

His Phe Ala Leu Thr His Tyr Ala Ala Gln Pro Gly Gly Tyr Tyr Asn
    130                 135                 140

Gly Thr Arg Lys Asp Arg Asn Lys Leu Arg His Leu Val Ser Val Lys
145                 150                 155                 160

Leu Gly Lys Ile Pro Thr Val Glu Asn Ser Ile Phe His Met Ala Ala
                165                 170                 175

Trp Ser Gly Ser Ala Cys His Asp Gly Arg Glu Trp Thr Tyr Ile Gly
            180                 185                 190

Val Asp Gly Pro Asp Asn Asp Ala Leu Val Lys Ile Lys Tyr Gly Glu
        195                 200                 205

Ala Tyr Thr Asp Thr Tyr His Ser Tyr Ala His Asn Ile Leu Arg Thr
    210                 215                 220

Gln Glu Ser Ala Cys Asn Cys Ile Gly Gly Asp Cys Tyr Leu Met Ile
225                 230                 235                 240

Thr Asp Gly Ser Ala Ser Gly Ile Ser Lys Cys Arg Phe Leu Lys Ile
                245                 250                 255

Arg Glu Gly Arg Ile Ile Lys Glu Ile Leu Pro Thr Gly Arg Val Glu
            260                 265                 270

His Thr Glu Glu Cys Thr Cys Gly Phe Ala Ser Asn Lys Thr Ile Glu
        275                 280                 285

Cys Ala Cys Arg Asp Asn Ser Tyr Thr Ala Lys Arg Pro Phe Val Lys
    290                 295                 300

Leu Asn Val Glu Thr Asp Thr Ala Glu Ile Arg Leu Met Cys Thr Lys
305                 310                 315                 320

Thr Tyr Leu Asp Thr Pro Arg Pro Asp Asp Gly Ser Ile Ala Gly Pro
                325                 330                 335

Cys Glu Ser Asn Gly Asp Lys Trp Leu Gly Gly Ile Lys Gly Gly Phe
            340                 345                 350
```

| | | | | | | | | | | | | |
|---|---|---|---|---|---|---|---|---|---|---|---|---|
|Val|His|Gln|Arg|Met|Ala|Ser|Lys|Ile|Gly|Arg|Trp|Tyr|Ser|Arg|Thr|
| | |355| | | |360| | | |365| | |

Met Ser Lys Thr Asn Arg Met Gly Met Glu Leu Tyr Val Lys Tyr Asp
        370             375             380

Gly Asp Pro Trp Thr Asp Ser Asp Ala Leu Thr Leu Ser Gly Val Met
385             390             395             400

Val Ser Ile Glu Glu Pro Gly Trp Tyr Ser Phe Gly Phe Glu Ile Lys
            405             410             415

Asp Lys Lys Cys Asp Val Pro Cys Ile Gly Ile Glu Met Val His Asp
            420             425             430

Gly Gly Lys Asp Thr Trp His Ser Ala Ala Thr Ala Ile Tyr Cys Leu
            435             440             445

Met Gly Ser Gly Gln Leu Leu Trp Asp Thr Val Thr Gly Val Asp Met
    450             455             460

Ala Leu
465

<210> SEQ ID NO 32
<211> LENGTH: 1408
<212> TYPE: DNA
<213> ORGANISM: Influenza B virus
<220> FEATURE:
<221> NAME/KEY: CDS
<222> LOCATION: (8)..(1408)

<400> SEQUENCE: 32

```
atgaaca atg cta cct tca act ata caa acg tta acc cta ttt ctc aca       49
        Met Leu Pro Ser Thr Ile Gln Thr Leu Thr Leu Phe Leu Thr
        1               5                   10 tca ggg gga gtg tta tta tca cta tat gtg tca gct tca ctg tca tac       97
Ser Gly Gly Val Leu Leu Ser Leu Tyr Val Ser Ala Ser Leu Ser Tyr
15                  20                  25                  30 tta ctg tat tcg gat ata ttg cta aaa ttt tca cca aca aaa ata act      145
Leu Leu Tyr Ser Asp Ile Leu Leu Lys Phe Ser Pro Thr Lys Ile Thr
                35                  40                  45 gca cca aca atg tca ttg gat tgc gcg aac gta tca aat gtt cag gct      193
Ala Pro Thr Met Ser Leu Asp Cys Ala Asn Val Ser Asn Val Gln Ala
            50                  55                  60 gtg aac cgt tct gca aca aaa gag atg aca ttt ctt ctc cca gag ccg      241
Val Asn Arg Ser Ala Thr Lys Glu Met Thr Phe Leu Leu Pro Glu Pro
65                  70                  75 gag tgg aca tac cct cgt tta tct tgc cag ggc tca acc ttt cag aaa      289
Glu Trp Thr Tyr Pro Arg Leu Ser Cys Gln Gly Ser Thr Phe Gln Lys
        80                  85                  90 gcg ctc cta att agc cct cat agg ttc gga gaa acc aga gga aac tca      337
Ala Leu Leu Ile Ser Pro His Arg Phe Gly Glu Thr Arg Gly Asn Ser
95                  100                 105                 110 gct ccc ttg ata ata agg gaa ccc ttt gtt gct tgt gga cca aag gaa      385
Ala Pro Leu Ile Ile Arg Glu Pro Phe Val Ala Cys Gly Pro Lys Glu
                115                 120                 125 tgc aga cac ttt gct cta acc cat tat gca gct caa cca ggg gga tac      433
Cys Arg His Phe Ala Leu Thr His Tyr Ala Ala Gln Pro Gly Gly Tyr
            130                 135                 140 tac aat gga aca aga aat gac aga aac aag ctg agg cat ctg att tca      481
Tyr Asn Gly Thr Arg Asn Asp Arg Asn Lys Leu Arg His Leu Ile Ser
            145                 150                 155 gtc aaa tta ggc aaa atc cca act gta gaa aac tcc att ttc cac atg      529
Val Lys Leu Gly Lys Ile Pro Thr Val Glu Asn Ser Ile Phe His Met
160                 165                 170
```

```
gca gct tgg agt ggg tcc gca tgc cat gat ggt aga gaa tgg aca tat      577
Ala Ala Trp Ser Gly Ser Ala Cys His Asp Gly Arg Glu Trp Thr Tyr
175             180                 185                 190 atc gga gtt gat ggc cct gac agt aat gca ctg atc aaa ata aaa tat      625
Ile Gly Val Asp Gly Pro Asp Ser Asn Ala Leu Ile Lys Ile Lys Tyr
                195                 200                 205 gga gaa gca tat act gac aca tac cat tcc tat gca aac aac atc cta      673
Gly Glu Ala Tyr Thr Asp Thr Tyr His Ser Tyr Ala Asn Asn Ile Leu
        210                 215                 220 aga aca caa gaa agt gcc tgc aat tgc atc ggg gga gat tgt cat ctt      721
Arg Thr Gln Glu Ser Ala Cys Asn Cys Ile Gly Gly Asp Cys His Leu
    225                 230                 235 atg ata act gat ggt tca gct tca gga att agt aaa tgc aga ttt ctt      769
Met Ile Thr Asp Gly Ser Ala Ser Gly Ile Ser Lys Cys Arg Phe Leu
240                 245                 250 aaa att cga gag ggt cga ata ata aaa gaa ata ttt cca aca gga aga      817
Lys Ile Arg Glu Gly Arg Ile Ile Lys Glu Ile Phe Pro Thr Gly Arg
255                 260                 265                 270 gta gat cat act gaa gaa tgc aca tgc ggg ttc gcc agc aat aaa acc      865
Val Asp His Thr Glu Glu Cys Thr Cys Gly Phe Ala Ser Asn Lys Thr
                275                 280                 285 ata gaa tgt gcc tgt aga gat aac agt tac aca gca aaa aga ccc ttt      913
Ile Glu Cys Ala Cys Arg Asp Asn Ser Tyr Thr Ala Lys Arg Pro Phe
        290                 295                 300 gtc aaa tta aat gtg gag act gat aca gct gaa ata aga ttg atg tgc      961
Val Lys Leu Asn Val Glu Thr Asp Thr Ala Glu Ile Arg Leu Met Cys
    305                 310                 315 aca gaa act tat ttg gac acc ccc aga cca gat gat gga agc ata aca     1009
Thr Glu Thr Tyr Leu Asp Thr Pro Arg Pro Asp Asp Gly Ser Ile Thr
320                 325                 330 ggg cct tgc gaa tca aat ggg gac aaa ggg ctt gga ggc atc aaa gga     1057
Gly Pro Cys Glu Ser Asn Gly Asp Lys Gly Leu Gly Gly Ile Lys Gly
335                 340                 345                 350 gga ttt gtc cat caa aga atg gca tct aag act gga aga tgg tac tcc     1105
Gly Phe Val His Gln Arg Met Ala Ser Lys Thr Gly Arg Trp Tyr Ser
                355                 360                 365 cga acg atg tct aaa act gaa aga atg ggg atg gaa ctg tat gtc agg     1153
Arg Thr Met Ser Lys Thr Glu Arg Met Gly Met Glu Leu Tyr Val Arg
        370                 375                 380 tat gat gga gac cca tgg act gac agt gac gcc ctt act cct agt gga     1201
Tyr Asp Gly Asp Pro Trp Thr Asp Ser Asp Ala Leu Thr Pro Ser Gly
    385                 390                 395 gta atg gtt tca atg aaa gaa cct ggt tgg tat tct ttt ggc ttc gaa     1249
Val Met Val Ser Met Lys Glu Pro Gly Trp Tyr Ser Phe Gly Phe Glu
400                 405                 410 ata aaa gat aag aaa tgt gat gtc ccc tgt att ggg ata gaa atg gta     1297
Ile Lys Asp Lys Lys Cys Asp Val Pro Cys Ile Gly Ile Glu Met Val
415                 420                 425                 430 cac gat ggt gga aaa gag act tgg cac tca gca gca aca gcc att tac     1345
His Asp Gly Gly Lys Glu Thr Trp His Ser Ala Ala Thr Ala Ile Tyr
                435                 440                 445 tgt ttg atg ggc tca gga caa ttg cta tgg gac act gtc aca ggt gtt     1393
Cys Leu Met Gly Ser Gly Gln Leu Leu Trp Asp Thr Val Thr Gly Val
        450                 455                 460 gac atg gct ctg taa                                                  1408
Asp Met Ala Leu
        465

<210> SEQ ID NO 33
<211> LENGTH: 466
```

<212> TYPE: PRT
<213> ORGANISM: Influenza B virus

<400> SEQUENCE: 33

```
Met Leu Pro Ser Thr Ile Gln Thr Leu Th

```
Val Ser Met Lys Glu Pro Gly Trp Tyr Ser Phe Gly Phe Glu Ile Lys
            405                 410                 415

Asp Lys Lys Cys Asp Val Pro Cys Ile Gly Ile Glu Met Val His Asp
        420                 425                 430

Gly Gly Lys Glu Thr Trp His Ser Ala Ala Thr Ala Ile Tyr Cys Leu
        435                 440                 445

Met Gly Ser Gly Gln Leu Leu Trp Asp Thr Val Thr Gly Val Asp Met
        450                 455                 460

Ala Leu
465

<210> SEQ ID NO 34
<211> LENGTH: 1115
<212> TYPE: DNA
<213> ORGANISM: Influenza B virus
<220> FEATURE:
<221> NAME/KEY: CDS
<222> LOCATION: (1)..(747)

<400> SEQUENCE: 34 atg tcg ctg ttt gga gac aca att gcc tac ctg ctt tca ttg aca gaa    48
Met Ser Leu Phe Gly Asp Thr Ile Ala Tyr Leu Leu Ser Leu Thr Glu
1               5                   10                  15 gat gga gaa ggc aaa gca gaa cta gca gaa aaa tta cac tgt tgg ttc    96
Asp Gly Glu Gly Lys Ala Glu Leu Ala Glu Lys Leu His Cys Trp Phe
            20                  25                  30 ggt ggg aaa gaa ttt gac cta gac tct gcc ttg gaa tgg ata aaa aac   144
Gly Gly Lys Glu Phe Asp Leu Asp Ser Ala Leu Glu Trp Ile Lys Asn
        35                  40                  45 aaa aga tgc tta act gat ata caa aaa gca cta att ggt gcc tct atc   192
Lys Arg Cys Leu Thr Asp Ile Gln Lys Ala Leu Ile Gly Ala Ser Ile
    50                  55                  60 tgc ttt tta aaa ccc aaa gac caa gaa aga aaa aga aga ttc atc aca   240
Cys Phe Leu Lys Pro Lys Asp Gln Glu Arg Lys Arg Arg Phe Ile Thr
65                  70                  75                  80 gag ccc cta tca gga atg gga aca aca gca aca aaa aag aaa ggc ctg   288
Glu Pro Leu Ser Gly Met Gly Thr Thr Ala Thr Lys Lys Lys Gly Leu
                85                  90                  95 att cta gct gag aga aaa atg aga aga tgt gtg agc ttt cat gaa gca   336
Ile Leu Ala Glu Arg Lys Met Arg Arg Cys Val Ser Phe His Glu Ala
            100                 105                 110 ttt gaa ata gca gaa ggc cat gaa agc tca gcg cta cta tat tgt ctc   384
Phe Glu Ile Ala Glu Gly His Glu Ser Ser Ala Leu Leu Tyr Cys Leu
        115                 120                 125 atg gtc atg tac ctg aac cct gga aat tat tca atg caa gta aaa cta   432
Met Val Met Tyr Leu Asn Pro Gly Asn Tyr Ser Met Gln Val Lys Leu
    130                 135                 140 gga acg ctc tgt gct ttg tgc gag aaa caa gca tca cat tca cac agg   480
Gly Thr Leu Cys Ala Leu Cys Glu Lys Gln Ala Ser His Ser His Arg
145                 150                 155                 160 gct cat agc aga gca gcg aga tct tca gtg cct gga gtg agg cga gaa   528
Ala His Ser Arg Ala Ala Arg Ser Ser Val Pro Gly Val Arg Arg Glu
                165                 170                 175 atg cag atg gtc tca gct atg aac aca gca aaa aca atg aat gga atg   576
Met Gln Met Val Ser Ala Met Asn Thr Ala Lys Thr Met Asn Gly Met
            180                 185                 190 gga aaa gga gaa gac gtc caa aaa ctg gca gaa gaa ctg caa agc aac   624
Gly Lys Gly Glu Asp Val Gln Lys Leu Ala Glu Glu Leu Gln Ser Asn
        195                 200                 205
```

```
att gga gta ttg aga tct ctt gga gca agt caa aag aat ggg gaa gga    672
Ile Gly Val Leu Arg Ser Leu Gly Ala Ser Gln Lys Asn Gly Glu Gly
    210             215                 220 att gca aag gat gta atg gaa gtg cta aag cag agc tct atg gga aat    720
Ile Ala Lys Asp Val Met Glu Val Leu Lys Gln Ser Ser Met Gly Asn
225             230                 235                 240 tca gct ctt gtg aag aaa tac cta taa tgctcgaacc atttcagatt          767
Ser Ala Leu Val Lys Lys Tyr Leu
                245 ctttcaattt gttctttat cttatcagct ctccatttca tggcttggac aatagggcat    827 ttgagtcaaa taaaagagg agtaaacatg aaaatacgaa taaaggtcc aaataaagag     887 acaataaaca gagaggtatc aattttgaga cacaattacc aaaaagaaat ccaggccaaa   947 gaaacaatga aggaagtact ctctgacaac atggaagtat tgagtgacca catagtgatt  1007 gaggggcttt ctgctgaaga gataataaaa atgggtaaaa cagttttgga ggtagaagaa  1067 ttgcattaaa ttcaattttt actgtatttc ttactatgca tttaagca              1115

<210> SEQ ID NO 35
<211> LENGTH: 248
<212> TYPE: PRT
<213> ORGANISM: Influenza B virus

<400> SEQUENCE: 35

Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
    50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
    130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
    210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245
```

```
<210> SEQ ID NO 36
<211> LENGTH: 1190
<212> TYPE: DNA
<213> ORGANISM: Influenza B virus
<220> FEATURE:
<221> NAME/KEY: CDS
<222> LOCATION: (25)..(771)

<400> SEQUENCE: 36
```

| | | | | | | | | | | | | | | | | | |
|---|---|---|---|---|---|---|---|---|---|---|---|---|---|---|---|---|---|
| agcagaagca cgcactttct taag | atg | tcg | ctg | ttt | gga | gac | aca | att | gcc | | | | | | | 51 |
| | Met | Ser | Leu | Phe | Gly | Asp | Thr | Ile | Ala | | | | | | | |
| | 1 | | | | 5 | | | | | | | | | | | |

| tac | ctg | ctt | tca | ttg | aca | gaa | gat | gga | gaa | ggc | aaa | gca | gaa | cta | gca | 99 |
|---|---|---|---|---|---|---|---|---|---|---|---|---|---|---|---|---|
| Tyr | Leu | Leu | Ser | Leu | Thr | Glu | Asp | Gly | Glu | Gly | Lys | Ala | Glu | Leu | Ala | |
| 10 | | | | | 15 | | | | | 20 | | | | | 25 | |

| gaa | aaa | tta | cac | tgt | tgg | ttc | ggt | ggg | aaa | gaa | ttt | gac | cta | gac | tct | 147 |
|---|---|---|---|---|---|---|---|---|---|---|---|---|---|---|---|---|
| Glu | Lys | Leu | His | Cys | Trp | Phe | Gly | Gly | Lys | Glu | Phe | Asp | Leu | Asp | Ser | |
| | | | | 30 | | | | | 35 | | | | | 40 | | |

| gcc | ttg | gaa | tgg | ata | aaa | aac | aaa | aga | tgc | tta | act | gat | ata | caa | aaa | 195 |
|---|---|---|---|---|---|---|---|---|---|---|---|---|---|---|---|---|
| Ala | Leu | Glu | Trp | Ile | Lys | Asn | Lys | Arg | Cys | Leu | Thr | Asp | Ile | Gln | Lys | |
| | | 45 | | | | | 50 | | | | | 55 | | | | |

| gca | cta | att | ggt | gcc | tct | atc | tgc | ttt | tta | aaa | ccc | aaa | gac | cag | gaa | 243 |
|---|---|---|---|---|---|---|---|---|---|---|---|---|---|---|---|---|
| Ala | Leu | Ile | Gly | Ala | Ser | Ile | Cys | Phe | Leu | Lys | Pro | Lys | Asp | Gln | Glu | |
| | | 60 | | | | | 65 | | | | | 70 | | | | |

| aga | aaa | aga | aga | ttc | atc | aca | gag | ccc | cta | tca | gga | atg | gga | aca | aca | 291 |
|---|---|---|---|---|---|---|---|---|---|---|---|---|---|---|---|---|
| Arg | Lys | Arg | Arg | Phe | Ile | Thr | Glu | Pro | Leu | Ser | Gly | Met | Gly | Thr | Thr | |
| 75 | | | | | 80 | | | | | 85 | | | | | | |

| gca | aca | aaa | aag | aaa | ggc | ctg | att | cta | gct | gag | aga | aaa | atg | aga | aga | 339 |
|---|---|---|---|---|---|---|---|---|---|---|---|---|---|---|---|---|
| Ala | Thr | Lys | Lys | Lys | Gly | Leu | Ile | Leu | Ala | Glu | Arg | Lys | Met | Arg | Arg | |
| 90 | | | | | 95 | | | | | 100 | | | | | 105 | |

| tgt | gtg | agc | ttt | cat | gaa | gca | ttt | gaa | ata | gca | gaa | ggc | cat | gaa | agc | 387 |
|---|---|---|---|---|---|---|---|---|---|---|---|---|---|---|---|---|
| Cys | Val | Ser | Phe | His | Glu | Ala | Phe | Glu | Ile | Ala | Glu | Gly | His | Glu | Ser | |
| | | | | 110 | | | | | 115 | | | | | 120 | | |

| tca | gcg | cta | cta | tat | tgt | ctc | atg | gtc | atg | tac | ctg | aat | cct | gga | aat | 435 |
|---|---|---|---|---|---|---|---|---|---|---|---|---|---|---|---|---|
| Ser | Ala | Leu | Leu | Tyr | Cys | Leu | Met | Val | Met | Tyr | Leu | Asn | Pro | Gly | Asn | |
| | | 125 | | | | | 130 | | | | | 135 | | | | |

| tat | tca | atg | caa | gta | aaa | cta | gga | acg | ctc | tgt | gct | ttg | tgc | gag | aaa | 483 |
|---|---|---|---|---|---|---|---|---|---|---|---|---|---|---|---|---|
| Tyr | Ser | Met | Gln | Val | Lys | Leu | Gly | Thr | Leu | Cys | Ala | Leu | Cys | Glu | Lys | |
| | | 140 | | | | | 145 | | | | | 150 | | | | |

| caa | gca | tca | cat | tca | cac | agg | gct | cat | agc | aga | gca | gcg | aga | tct | tca | 531 |
|---|---|---|---|---|---|---|---|---|---|---|---|---|---|---|---|---|
| Gln | Ala | Ser | His | Ser | His | Arg | Ala | His | Ser | Arg | Ala | Ala | Arg | Ser | Ser | |
| | 155 | | | | | 160 | | | | | 165 | | | | | |

| gtg | ccc | gga | gtg | aga | cga | gaa | atg | cag | atg | gtc | tca | gct | atg | aac | aca | 579 |
|---|---|---|---|---|---|---|---|---|---|---|---|---|---|---|---|---|
| Val | Pro | Gly | Val | Arg | Arg | Glu | Met | Gln | Met | Val | Ser | Ala | Met | Asn | Thr | |
| 170 | | | | | 175 | | | | | 180 | | | | | 185 | |

| gca | aaa | aca | atg | aat | gga | atg | gga | aaa | gga | gaa | gac | gtc | caa | aaa | ctg | 627 |
|---|---|---|---|---|---|---|---|---|---|---|---|---|---|---|---|---|
| Ala | Lys | Thr | Met | Asn | Gly | Met | Gly | Lys | Gly | Glu | Asp | Val | Gln | Lys | Leu | |
| | | | | 190 | | | | | 195 | | | | | 200 | | |

| gca | gaa | gag | ctg | caa | agc | aac | att | gga | gtg | ctg | aga | tct | ctt | ggg | gca | 675 |
|---|---|---|---|---|---|---|---|---|---|---|---|---|---|---|---|---|
| Ala | Glu | Glu | Leu | Gln | Ser | Asn | Ile | Gly | Val | Leu | Arg | Ser | Leu | Gly | Ala | |
| | | | 205 | | | | | 210 | | | | | 215 | | | |

| agt | caa | aag | aat | ggg | gaa | gga | att | gca | aag | gat | gta | atg | gaa | gtg | cta | 723 |
|---|---|---|---|---|---|---|---|---|---|---|---|---|---|---|---|---|
| Ser | Gln | Lys | Asn | Gly | Glu | Gly | Ile | Ala | Lys | Asp | Val | Met | Glu | Val | Leu | |
| | | 220 | | | | | 225 | | | | | 230 | | | | |

| aag | cag | agc | tct | atg | gga | aat | tca | gct | ctt | gtg | aag | aaa | tat | ctg | taa | 771 |
|---|---|---|---|---|---|---|---|---|---|---|---|---|---|---|---|---|
| Lys | Gln | Ser | Ser | Met | Gly | Asn | Ser | Ala | Leu | Val | Lys | Lys | Tyr | Leu | | |
| | 235 | | | | | 240 | | | | | 245 | | | | | |

```
tgctcgaacc atttcagatt ctttcaattt gttcttttat cttatcagct ctccatttca      831
tggcttggac aatagggcat ttgaatcaaa taaaagagg agtaaacatg aaaatacgaa       891
```

```
taaaaagtcc aaacaaagag acaataaaca gagaggtatc aatttttgaga cacagttacc      951 aaaaagaaat ccaggccaaa gaaacaatga aggaagtact ctctgacaac atggaggtat     1011
tgagtgatca catagtaatt gagggggcttt ctgccgaaga gataataaaa atgggtgaaa     1071 cagtttttgga gatagaagaa ttgcattaaa ttcaattttt actgtatttc ttactatgca     1131
tttaagcaaa ttgtaatcaa tgtcagcaaa taaactggaa aaagtgcgtt gtttctact        1190
```

<210> SEQ ID NO 37
<211> LENGTH: 248
<212> TYPE: PRT
<213> ORGANISM: Influenza B virus

<400> SEQUENCE: 37

```
Met Ser Leu Phe Gly Asp Thr Ile Ala Tyr Leu Leu Ser Leu Thr Glu
1               5                   10                  15

Asp Gly Glu Gly Lys Ala Glu Leu Ala Glu Lys Leu His Cys Trp Phe
            20                  25                  30

Gly Gly Lys Glu Phe Asp Leu Asp Ser Ala Leu Glu Trp Ile Lys Asn
        35                  40                  45

Lys Arg Cys Leu Thr Asp Ile Gln Lys Ala Leu Ile Gly Ala Ser Ile
50                  55                  60

Cys Phe Leu Lys Pro Lys Asp Gln Glu Arg Lys Arg Arg Phe Ile Thr
65                  70                  75                  80

Glu Pro Leu Ser Gly Met Gly Thr Thr Ala Thr Lys Lys Lys Gly Leu
                85                  90                  95

Ile Leu Ala Glu Arg Lys Met Arg Arg Cys Val Ser Phe His Glu Ala
            100                 105                 110

Phe Glu Ile Ala Glu Gly His Glu Ser Ser Ala Leu Leu Tyr Cys Leu
        115                 120                 125

Met Val Met Tyr Leu Asn Pro Gly Asn Tyr Ser Met Gln Val Lys Leu
130                 135                 140

Gly Thr Leu Cys Ala Leu Cys Glu Lys Gln Ala Ser His Ser His Arg
145                 150                 155                 160

Ala His Ser Arg Ala Ala Arg Ser Ser Val Pro Gly Val Arg Arg Glu
                165                 170                 175

Met Gln Met Val Ser Ala Met Asn Thr Ala Lys Thr Met Asn Gly Met
            180                 185                 190

Gly Lys Gly Glu Asp Val Gln Lys Leu Ala Glu Glu Leu Gln Ser Asn
        195                 200                 205

Ile Gly Val Leu Arg Ser Leu Gly Ala Ser Gln Lys Asn Gly Glu Gly
        210                 215                 220

Ile Ala Lys Asp Val Met Glu Val Leu Lys Gln Ser Ser Met Gly Asn
225                 230                 235                 240

Ser Ala Leu Val Lys Lys Tyr Leu
                245
```

<210> SEQ ID NO 38
<211> LENGTH: 1076
<212> TYPE: DNA
<213> ORGANISM: Influenza B virus
<220> FEATURE:
<221> NAME/KEY: CDS
<222> LOCATION: (1)..(747)

<400> SEQUENCE: 38

```
atg tcg ctg ttt gga gac aca att gcc tac ctg ctt tca ttg aca gaa      48
```

```
Met Ser Leu Phe Gly Asp Thr Ile Ala Tyr Leu Leu Ser Leu Thr Glu
 1               5                  10                  15 gat gga gaa ggc aaa gca gaa cta gca gaa aaa tta cac tgt tgg ttc    96
Asp Gly Glu Gly Lys Ala Glu Leu Ala Glu Lys Leu His Cys Trp Phe
             20                  25                  30 ggt ggg aaa gaa ttt gac cta gac tct gcc ttg gaa tgg ata aaa aac   144
Gly Gly Lys Glu Phe Asp Leu Asp Ser Ala Leu Glu Trp Ile Lys Asn
         35                  40                  45 aaa aga tgc tta act gat ata caa aaa gca cta att ggt gcc tct atc   192
Lys Arg Cys Leu Thr Asp Ile Gln Lys Ala Leu Ile Gly Ala Ser Ile
     50                  55                  60 tgc ttt tta aaa ccc aaa gac cag gaa aga aaa aga aga ttc atc aca   240
Cys Phe Leu Lys Pro Lys Asp Gln Glu Arg Lys Arg Arg Phe Ile Thr
 65                  70                  75                  80 gaa ccc cta tca gga atg gga aca aca gca aca aaa aag aaa ggc ctg   288
Glu Pro Leu Ser Gly Met Gly Thr Thr Ala Thr Lys Lys Lys Gly Leu
                 85                  90                  95 att cta gct gag aga aag atg aga aga tgt gtg agc ttt cat gaa gca   336
Ile Leu Ala Glu Arg Lys Met Arg Arg Cys Val Ser Phe His Glu Ala
             100                 105                 110 ttt gaa ata gca gaa ggc cat gaa agc tca gcg cta cta tat tgt ctc   384
Phe Glu Ile Ala Glu Gly His Glu Ser Ser Ala Leu Leu Tyr Cys Leu
         115                 120                 125 atg gtc atg tac cta aat cct gga aat tat tca atg caa gta aaa cta   432
Met Val Met Tyr Leu Asn Pro Gly Asn Tyr Ser Met Gln Val Lys Leu
     130                 135                 140 gga acg ctc tgt gct ttg tgc gag aaa caa gca tca cat tca cac agg   480
Gly Thr Leu Cys Ala Leu Cys Glu Lys Gln Ala Ser His Ser His Arg
145                 150                 155                 160 gct cat agc aga gca gcg aga tct tca gta ccc gga gtg aga cga gaa   528
Ala His Ser Arg Ala Ala Arg Ser Ser Val Pro Gly Val Arg Arg Glu
                 165                 170                 175 atg cag atg gtc tca gct atg aac aca gca aaa aca atg aat gga atg   576
Met Gln Met Val Ser Ala Met Asn Thr Ala Lys Thr Met Asn Gly Met
             180                 185                 190 gga aaa gga gaa gac gtc caa aaa ctg gca gaa gag ctg caa agc aac   624
Gly Lys Gly Glu Asp Val Gln Lys Leu Ala Glu Glu Leu Gln Ser Asn
         195                 200                 205 att gga gtg ctg aga tcc ctt ggg gca agt caa aag aat gga gaa gga   672
Ile Gly Val Leu Arg Ser Leu Gly Ala Ser Gln Lys Asn Gly Glu Gly
     210                 215                 220 att gca aag gat gta atg gaa gtg tta aag cag agc tct atg gga aat   720
Ile Ala Lys Asp Val Met Glu Val Leu Lys Gln Ser Ser Met Gly Asn
225                 230                 235                 240 tca gct ctt gtg aag aaa tat cta tga tgctagaacc atttcagatt         767
Ser Ala Leu Val Lys Lys Tyr Leu
                 245 ctttcaattt gttctttcat cttatcagct ctccatttca tggcttggac aatagggcat   827 ttgaatcaaa taaaagagg agtaaacatg aaaatacgaa taaaggtcc aaacaaagag     887 acaataaaca gagaggtatc aatttttgaga cacagttacc aaaaagaaat ccaggccaaa   947 gaaacaatga aggaagtact ctctgacaac atggaggtat tgagtgacca catagtaatt   1007 gaggggcttt ctgccgaaga gataataaaa atgggtgaaa cagttttgga gatagaagaa   1067 ttgcattaa                                                           1076

<210> SEQ ID NO 39
<211> LENGTH: 248
<212> TYPE: PRT
```

<213> ORGANISM: Influenza B virus

<400> SEQUENCE: 39

```
Met Ser Leu Phe Gly Asp Thr Ile Ala Tyr Leu Leu Ser the first influenza HA polypeptide comprises influenza A HA subtype H3 and the second influenza HA polypeptide comprises influenza A HA subtype H7;

the first influenza HA polypeptide comprises influenza A HA subtype H1 and the second influenza HA polypeptide comprises influenza A HA subtype H3;

the first influenza HA polypeptide comprises influenza A HA subtype H2 and the second influenza HA polypeptide comprises influenza A HA subtype H7;

the first influenza HA polypeptide comprises influenza A HA subtype H5 and the second influenza HA polypeptide comprises influenza A HA subtype H3; or the first influenza HA polypeptide comprises influenza A HA subtype H1 and the second influenza HA polypeptide comprises influenza A HA subtype H7.

6. The composition of claim 1, wherein the first influenza HA polypeptide comprises an influenza A HA polypeptide and the second influenza HA polypeptide comprises an influenza B HA polypeptide.

7. The composition of claim 6, wherein (i) the first influenza HA polypeptide comprises influenza A HA subtype H1, H3, H5, H7 or H9; and (ii) the second influenza HA polypeptide comprises influenza B Yamagata-like lineage HA or influenza B Victoria-like lineage HA.

8. The composition of claim 1, further comprising:

a first VLP comprising a first influenza neuraminidase (NA) polypeptide.

9. The composition of claim 8, further comprising:

a second VLP comprising a second influenza NA polypeptide, wherein the first and the second NA polypeptide are different subtypes and/or are from different influenza viruses.

10. The composition of claim 9, wherein:

(i) the first influenza HA polypeptide comprises influenza A HA subtype H1;

(ii) the second influenza HA polypeptide comprises influenza A HA subtype H3; and the composition further comprises:

(iii) a third VLP comprising a third influenza A HA HA subtype H5;

(iv) a fourth VLP comprising a fourth influenza A HA HA subtype H7;

(v) a fifth VLP comprising an influenza A N1;

(vi) a sixth VLP comprising an influenza A N2;

(vii) a seventh VLP comprising an influenza B Victoria-like HA or an influenza B Yamagata-like HA; and (viii) optionally an eighth VLP comprising influenza B Victoria-like HA or an influenza B Yamagata-like HA that is different from the seventh VLP.

11. The composition of claim 1, wherein the at least two different influenza VLPs further comprise an influenza matrix polypeptide.

12. The composition of claim 11, wherein the at least two different influenza VLPs further comprise:

(i) influenza A matrix polypeptide M1, M2, or both M1 and M2; or (ii) influenza B matrix polypeptide M1, BM2, or both M1 and BM2.

13. The composition of claim 1, wherein:

the first influenza HA polypeptide comprises influenza A HA subtype H1 and the second influenza A HA polypeptide comprises HA subtype H3;

the composition further comprises a third VLP comprising influenza A HA subtype H5 and a fourth VLP comprising influenza A HA subtype H7; and wherein the first to fourth VLPs further comprise influenza A matrix protein 1 (M1) and matrix protein 2 (M2).

14. The composition of claim 11, wherein:

the first influenza HA polypeptide comprises influenza A HA subtype H1 and the second influenza HA polypeptide comprises influenza A HA subtype H2;

the composition further comprises a third VLP comprising influenza A HA subtype H3, a fourth VLP comprising influenza A HA subtype H5, a fifth VLP comprising influenza A HA subtype H7, a sixth VLP comprising influenza A HA subtype H9, a seventh VLP comprising influenza A N1, and an eighth VLP comprising influenza A N2; and wherein the first to fourth VLPs further comprise influenza A matrix protein 1 (M1) and influenza A matrix protein 2 (M2).

15. The composition of claim 1, further comprising an adjuvant.

16. The composition of claim 15, wherein the adjuvant is lipid A monophosphoryl (MPL).

17. The composition of claim 1, formulated for intranasal administration.

18. The composition of claim 1, wherein the at least two different influenza VLPs are produced by transfecting a host cell with:

(i) a vector encoding the HA polypeptide or a vector encoding the NA polypeptide; and (ii) a vector encoding an influenza matrix polypeptide, under conditions sufficient to allow for expression of the HA polypeptide or NA polypeptide, and matrix polypeptide.

19. A syringe comprising the composition of claim 1.

20. A method of eliciting an immune response to influenza virus in a subject, comprising administering a therapeutically effective amount of the composition of claim 1 to a subject, thereby eliciting an immune response to influenza virus in a subject.

21. A method of immunizing a subject against influenza virus, comprising administering to the subject a therapeutically effective amount of the composition of claim 1 to a subject, thereby immunizing the subject against influenza virus.

22. The method of claim 20, wherein the immune response to influenza virus comprises an immune response to influenza A, influenza B, or both.

23. The method of claim 20, wherein the composition is administered intranasally.

24. The method of claim 20, wherein the subject is administered about 1 to about 25 μg of each of the at least two different VLPs.

25. The method of claim 24, wherein the subject is administered about 15 μg of each of the at least two different VLPs.

26. The method of claim 20, wherein the subject is a mammal or a bird.

27. The method of claim 20, wherein the subject is a human.

28. A kit, comprising:
a first container comprising the composition of claim 1; and
optionally a second container comprising a third VLP comprising a first influenza NA polypeptide, a syringe, a syringe atomizer, or combinations thereof.

29. The kit of claim 28, wherein the composition further comprises an adjuvant.

\* \* \* \* \*